United States Patent [19]
Swaminathan et al.

[11] Patent Number: 5,792,608
[45] Date of Patent: Aug. 11, 1998

[54] NUCLEASE STABLE AND BINDING COMPETENT OLIGOMERS AND METHODS FOR THEIR USE

[75] Inventors: Sundaramoorthi Swaminathan; Mark Matteucci, both of Burlingame; Robert J. Jones, Millbrae; Jeff Pudlo, Burlingame; John Munger, San Francisco, all of Calif.

[73] Assignee: Gilead Sciences, Inc., Foster City, Calif.

[21] Appl. No.: 417,632

[22] Filed: Apr. 6, 1995

Related U.S. Application Data

[60] Division of Ser. No. 990,848, Dec. 11, 1992, abandoned, which is a continuation-in-part of Ser. No. 806,710, Dec. 12, 1991, abandoned.

[51] Int. Cl.[6] .................................................. C12Q 1/68
[52] U.S. Cl. .............................. 435/6; 536/24.5; 436/501
[58] Field of Search .............................. 435/6; 536/24.5; 436/501; 935/77, 78, 81

[56] References Cited

FOREIGN PATENT DOCUMENTS

| | | |
|---|---|---|
| WO 86/05518 | 9/1986 | WIPO . |
| WO 89/05358 | 6/1989 | WIPO . |
| WO 90/15065 | 12/1990 | WIPO . |
| WO 92 05186 | 4/1992 | WIPO . |

OTHER PUBLICATIONS

Chollet et al., "DNA containing the base analogue 2-aminoadenine: preparation use as hybridization probes and cleavage by restriction endonucleases," Nuc Acids Res 16(1):305–317 (1988).

Dagle et al., "Targeted degradation of mRNA in Xenopus oocytes and embryos directed by modified oligonucleotides: studies of An2 and cyclin in embryogenesis," Nuc Acids Res 18(16):4751–4757 (May 22, 1990).

Letsinger et al., "Cationic Oligonucleotides," J Am Chem Soc 110:4470–4471 (1988).

Maniatis et al., "Molecular Cloning –A Laboratory Manual," Molecular Cloning –A Laboratory Manual pp. 324–325 (1982).

Maniatis et al., "Molecular Cloning –A Laboratory Manual," Molecular Cloning –A Laboratory Manual pp. 382–389 (1982).

Quartin et al., "Number and distribution of methylphosphonate linkages in oligodeoxynucleotides affect exo–and endonuclease sensitivity and ability to form RNase H substrates," Nuc Acids Res 17(18):7253–7262 (1989).

Tarkoy et al., "31. Nucleic–Acid Analogues with Constraint Conformational Flexibility in the Sugar–Phosphate Backbone (Bicyclo–DNA')," Helvetica Chimica Acta 76:481–510 (1993).

Wetmur et al., "Kinetics of Renaturation of DNA," J Mol Biol 31:349–370 (1968).

"New nucleotide sequence data on the EMBL File Server," Nuc Acids Res 19(21):6063–6079 (1991).

Adams et al., "Preparation and hybridization properties of oligonucleotides containing 1–alpha–D–arabinofuranosylthymine," Nuc Acids Res 19(13):3647–3651 (1991).

Dewanjee et al., "Development of Sensitive Radioiodinated Anti–Sense Oligonucleotide Probes by Conjugation Technique," Bioconj Chem 2(4):195–200 (191).

Haralambidis et al, "The preparation of polyamide–oligonucleotide probes containing multiple non–radioactive labels," Nuc Acids Res 18(3):501–505 (1990).

(List continued on next page.)

*Primary Examiner*—Scott W. Houtteman
*Attorney, Agent, or Firm*—Daryl D. Muenchau

[57] ABSTRACT

Oligomers are disclosed which have modified internucleotide linkages and can form triplex and duplex structures by binding to complementary nucleic acid sequences. The oligomers of the invention may be incorporated into carriers and may be constructed to have any desired sequence. Compositions of the invention can be used for diagnostic purposes in order to detect viruses or disease conditions.

35 Claims, 38 Drawing Sheets

OTHER PUBLICATIONS

Haralambidis et al., "The synthesis of polyamide –oligonucleotide conjungate molecules," Nuc Acids Res 18(3):493–499 (1990).

Murakami et al., "Highly sensitive detection of DNA using enzyme–linked DNA–probe. 1. Colorimetric and fluorometric detection," Nuc Acids Res 17(4):5587–5595 (1989).

Oren et al., "Isolation and characterization of a species–specific DNA probe for Candida albicans," Nuc Acids Res 19(25):7113–7116 (1991).

Research Genetics, "Advertisement," Nuc Acids Res 19(19) (1991).

Shimidzu et al., "A rapid synthesis of oligoadenylic acid by polycondensation," Nuc Acids Res Symposium Series 10; pp. 177–180 (1981).

Tanimura et al, "Feature of Internucleotidic 2',3'–Cyclic-phosphate Intermediates During Liquid and Solid Phase Synthesis of RNA Fragments and Practical Synthesis of Octaadenylate in the Phosphoramidite Approach," Chemistry Letters, Tokyo JP pp. 1057–1060 (1987).

Van Ness et al, "The use of oligodeoxynucleotide probes in chaotrope–based hybridization solutions," Nuc Acids Res 19(19):5143–5151 (1991).

Wagner et al, "Antisense Gene Inhibition by Oligonucleotides Containing C–5 Propyne Pyrimidines," Science 260:1510–1513 (1993).

Kim, Choung Un, et al., "A New Class of Acyclic Phosphonate Nucleotide Analogues: Phosphonate Isosteres of Acyclovir and Ganciclovir Monophosphates as Antiviral Agents", J. Med. Chem. (1991) 34:2286–2294.

Greene, T.W., et al., editors, *Protective Groups in Organic Synthesis, Second Edition* (published by John Wiley & Sons, Inc., New York). pp. 97 and 105 are provided.

R = CN, CF(CH$_3$)$_2$, CH(CF$_3$)$_2$
R' = Me, Et

R = CN, CF(CH₃)₂, CH(CF₃)₂
R' = Me, Et

1) MeONa/MeOH
2) DMTCl, Pyr
3) PA

N,N-diisopropylamino-β-
cyanoethoxyphosphine

N,N-diisopropylamino-methoxy-
phosphine

N,N-diethylamino-methoxy-
phosphine

N,N-diethylamino-β-cyanoethoxy
phosphine

N-morpholino-β-cyanoethoxy-
phosphine

N-morpholino methoxy-
phosphine

Bis morpholino-phosphine

N,N-dimethylamino-
β-cyanoethylmercapto-
phosphine

N,N-dimethylamino-
2,4-dichlorobenzylmercapto-
phosphine

Bis(N,N-diisopropylamino)-
phosphine 2-chlorophenyl phosphate 4-chlorophenyl phosphate 2,4-dichlorophenyl phosphate 2,4-dibromophenyl phosphate $X = O$ or $S$ $R = H$, $NO_2$ and $CF_3$ N,N-diisopropylamino-methyl-phosphine N,N-diethylamino-methyl-phosphine X = O or S $X^2$ = CO, CS or $SO_2$ $X^3$ = O, S, $CH_2$, $CF_2$, CFH, NH, $NCH_3$ 1) MeO Na/MeOH
2) TBAF / THF
3) MeO−C(=O)−CF₃
4) DMT Cl / Pyr
5) PA 1) MeO Na/MeOH
2) DMT Cl / Pyr
3) TBAF / THF
4) PA

NUCLEASE STABLE AND BINDING COMPETENT OLIGOMERS AND METHODS FOR THEIR USE

This is a divisional of application Ser. No. 07/990,848 filed on Dec. 11, 1992, now abandoned, which is a continuation-in-part of U.S. Ser. No. 07/806,710, filed Dec. 12, 1991, now abandoned.

TECHNICAL FIELD

The invention relates generally to novel oligonucleotide analogs, nucleoside analogs and their use in diagnosis by binding of the oligonucleotide analogs to single or double stranded nucleic acid target sequences. More specifically, the invention concerns oligomers containing riboacetal and related substitute linkages and the novel nucleoside analogs used to synthesize such oligomers.

BACKGROUND ART

The application of oligonucleotides and oligonucleotide analogs (oligomers) for therapeutic uses represents a relatively new development in drug design and discovery. Several fundamental therapeutic approaches that utilize oligomers have been proposed.

One approach is based largely on interfering with gene expression through oligomer binding to a complementary RNA sequence. This application is known as "antisense" therapy because the oligomer base sequence is identical to the antisense strand of the gene that gave rise to the RNA (Uhlmann, E., et al., *Chem Reviews* (1990) 90:543–584). Another approach, referred to herein as "triple helix" therapy, utilizes oligomers that bind to duplex DNA as detailed below. Binding to a target DNA is sequence specific but involves different base pairing rules.

Both antisense and triple helix therapies exert therapeutic effects via binding to complementary nucleic acid sequences that are responsible for disease conditions or sequences that are found in the genome of pathogenic organisms such as bacteria, protozoa, fungi or viruses. By modulating the expression of a gene important for establishment, maintenance or elimination of a disease condition, the corresponding condition may be cured, prevented or ameliorated.

Another therapeutic approach that is based on the use of oligomers includes generation of "aptamers" and is disclosed and claimed in commonly owned application Ser. Nos. 745,215, 659,980 and 658,849. This approach utilizes oligomers that specifically bind to proteins thereby interfering with their function. The use of oligomers that mimic the structure of certain RNA molecules that are bound by intracellular proteins has also been adduced as a therapeutic approach as described in international application no. PCT/US91/01822.

Modifications of binding competent oligomers that enhance their affinity for target sequences will generally improve the therapeutic potential for oligomers used as therapeutic agents and their usefulness in diagnostic assays for oligomers used as diagnostic agents. Previous approaches to improve binding affinity for complementary nucleic acids include (i) covalent linkage of intercalating agents to oligomers (Asseline, U., et al., *Proc. Natl. Acad. Sci.* (1984) 81:3297–3401), (ii) introduction of modified bases to form more stable base pairs (Inoue, H. et al., *Nucl. Acids Res.* (1985) 13:7119) and (iii) altering the charge characteristics of oligomer linkages (Letsinger, R. L. et al., *J Am. Chem. Soc.* (1988) 110:4470). Morpholino-type substitute linkages are described in U.S. Pat. No. 5,034,506 and in some cases give rise to an increased affinity of the oligomer for complementary target sequences.

DNA synthesis via amidite and hydrogen phosphonate chemistries has been described (U.S. Pat. Nos. 4,725,677; 4,415,732; 4,458,066; 4,959,463).

The diagnostic usefulness of oligomers is also generally enhanced by modifications that increase oligomer uptake by cells or reduce the rate of metabolism by cells or serum. Such modifications include (i) increased stability toward nuclease activity, (ii) reduced oligomer charge and/or (iii) increased lipophilicity of the oligomer. Thus, a need exists for nuclease resistant oligomers that are capable of sequence specific binding. Oligomers having the substitute linkages as described herein exhibit sequence-specific binding to complementary single stranded and duplex target sequences and are resistant to nuclease degradation. Additional properties of the compounds are described in detail below.

SUMMARY OF THE INVENTION

The present invention is directed to oligomers and pharmaceutically acceptable salts thereof, said oligomers comprising at least two nucleomonomers, wherein a first nucleomonomer and a second nucleomonomer are coupled through a substitute linkage, wherein the substitute linkage comprises a 5-, 6- or 7-member ring containing C2' and C3' of the first nucleomonomer covalently linked through a bridging moiety to C4' of the second nucleomonomer. The nucleomonomers are coupled together via a one, two or three atom bridging moiety (bridge) that links the 5-, 6-, or 7-member ring to an adjacent C4'. Preferred embodiments are oligomers wherein the ring is a 5-member ring.

STRUCTURAL FORMULAS

Figure 1:
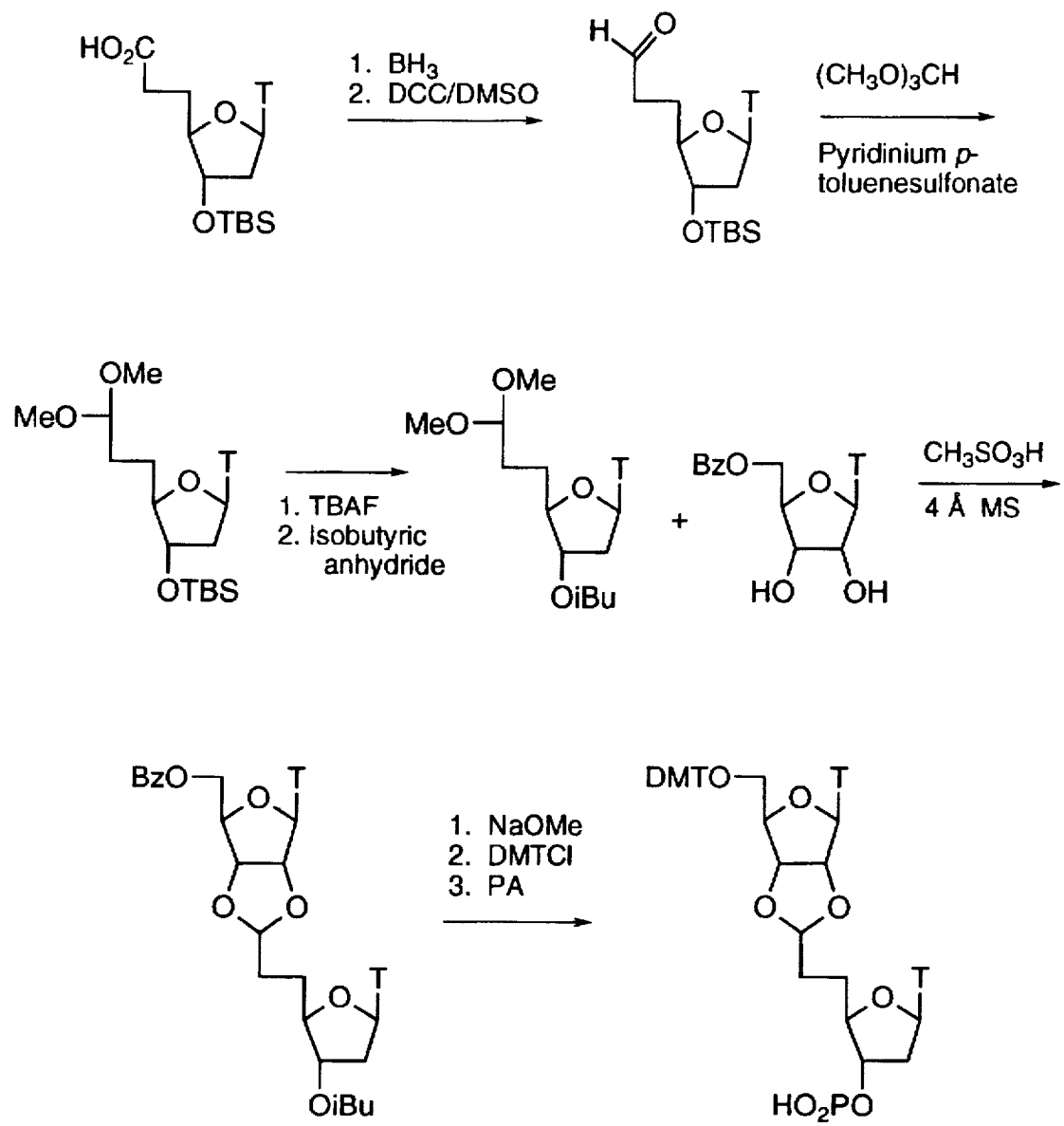
FIG. 1 describes the synthesis of a riboacetal DMT synthon of Example 1.

Structural formulas described herein are designated as roman numerals (I, II, etc) and chemical compounds are designated a numeral (1, 2, etc).

DETAILED DESCRIPTION OF THE INVENTION DEFINITIONS

Nucleomonomer. As used herein, the term "nucleomonomer" means a moiety comprising (1) a base covalently linked to (2) a second moiety. Nucleomonomers include nucleosides and nucleotides. Nucleomonomers can be linked to form oligomers that bind to target or complementary base sequences in nucleic acids in a sequence specific manner.

A "second moiety" as used herein includes a sugar moiety, usually a pentose, and those species which contain modifications of the sugar moiety, for example, wherein one or more of the hydroxyl groups are replaced with a halogen, a heteroatom, an aliphatic groups, or are functionalized as ethers, amines, thiols, and the like. The pentose moiety can be replaced by a hexose or an alternate structure such as a cyclopentane ring, a 6-member morpholino ring and the like. Nucleomonomers as defined herein are also intended to include a base linked to an amino acid and/or an amino acid analog having a free carboxyl group and/or a free amino group and/or protected forms thereof.
Base "Base" as used herein includes those moieties which contain not only the known purine and pyrimidine heterocycles, but also heterocycle analogs and tautomers thereof. Purines include adenine, guanine and xanthine and exemplary purine analogs include 8-oxo-$N^6$-methyladenine and 7-deazaxanthine. Pyrimidines include uracil and cytosine and their analogs such as 5-methylcytosine, 5-(1-propynyluracil), 5-(1-propynylcytosine), 5-methyluracil and 4,4-ethanocytosine.
Nucleoside As used herein, "nucleoside" means a base covalently attached to a sugar or sugar analog and which may contain a phosphite or phosphine. The term nucleoside includes ribonucleosides, deoxyribonucleosides, or any other nucleoside which is an N-glycoside or C-glycoside of a base. The stereochemistry of the sugar carbons can be other than that of D-ribose.

Nucleosides include those species which contain modifications of the sugar moiety, for example, wherein one or more of the hydroxyl groups are replaced with a halogen, a heteroatom, an aliphatic group, or are functionalized as ethers, amines, thiols, and the like. The pentose moiety can be replaced by a hexose or an alternate structure such as a cyclopentane ring, a 6-member morpholino ring and the like.

The term "nucleoside" will include ribonucleosides, deoxyribonucleosides, or to any other nucleoside which is an N-glycoside or C-glycoside of a purine or pyrimidine base, or modified purine or pyrimidine base. The stereochemistry of the sugar carbons can be other than that of D-ribose in one or more residues. The pentose moiety can be replaced by a hexose and incorporated into oligomers as described (Augustyns, K., et al Nucl Acids Res (1992) 18:4711–4716). Also included are analogs where the ribose or deoxyribose moiety is replaced by an alternate structure such as a hexose or such as the 6-member morpholino ring described in U.S. Pat. No. 5,034,506. Nucleosides as defined herein also includes a purine or pyrimidine base linked to an amino acid or amino acid analog having a free carboxyl group and a free amino group or protected forms thereof.
Nucleotide As used herein, "nucleotide" means a nucleoside having a phosphate group or phosphate analog.
Sugar Modification As used herein, "sugar modification" means any pentose or hexose moiety other than 2'-deoxyribose. Modified sugars include D-ribose, 2'-O-alkyl, 2'-amino, 2'-halo functionalized pentoses, hexoses and the like. Sugars having a stereochemistry other than that of a D-ribose are also included.
Linkage As used herein, "linkage" means a phosphodiester moiety (—O—P(O)(O)—O—) that covalently couples adjacent nucleomonomers.
Substitute Linkages As used herein, "substitute linkage" means any analog of the native phosphodiester group or any suitable moiety that covalently couples adjacent nucleomonomers. Substitute linkages include phosphodiester analogs, e.g. such as phosphorothioate and methylphosphonate, and nonphosphorus containing linkages, e.g. such as acetals and amides. Substitute linkages include the nonphosphorous containing linkages of the invention.
Switchback As used herein, "switchback" means an oligomer having at least one region of inverted polarity. Switchback oligomers are able to bind to opposite strands of a duplex to form a triplex on both strands of the duplex. The linker ("switchback linker") joining the regions of inverted polarity is a substitute linkage.
Crosslinking moiety "Crosslinking moiety" includes a group or moiety in an oligomer that forms a covalent bond with a target nucleic acid. Crosslinking moieties include covalent bonding species that covalently link an oligomer to target nucleic acids either spontaneously (e.g. $N^4,N^4$-ethanocytosine) or via photoactivation (e.g. psoralen and the like).

Oligomers

"Oligomers" are defined herein as two or more nucleomonomers covalently coupled to each other by a linkage or substitute linkage moiety. Thus, an oligomer can have as few as two convalently linked nucleomonomers (a dimer). Oligomers can be binding competent and, thus, can base pair with cognate single-stranded or double-stranded nucleic acid sequences. Oligomers (e.g. dimers-hexamers) are also useful as synthons for longer oligomers as described herein. oligomers can also contain abasic sites and pseudonucleosides.

Oligomer includes oligonucleotides, oligonucleosides, polydeoxyribo-nucleotides (containing 2'-deoxy-D-ribose or modified forms thereof), i.e., DNA, polyribonucleotides (containing D-ribose or modified forms thereof), i.e., RNA, and any other type of polynucleotide which is an N-glycoside or C-glycoside of a purine or pyrimidine base, or modified purine or pyrimidine base. Oligomer as used herein is also intended to include compounds where adjacent nucleomonomers are linked via amide linkages as previously described (Nielsen, P. E., et al, *Science* (1991) 254:1497–1500). Elements ordinarily found in oligomers, such as the furanose ring and/or the phosphodiester linkage can be replaced with any suitable functionally equivalent element. "Oligomer" is thus intended to include any structure that serves as a scaffold or support for the bases wherein the scaffold permits binding to target nucleic acids in a sequence-dependent manner. Oligomers that are currently known can be defined into four groups that can be characterized as having (i) phosphodiester and phosphodiester analog (phosphorothioate, methylphosphonate, etc) linkages, (ii) substitute linkages that contain a non-phosphorous isostere (riboacetal, formacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

Blocking Groups

As used herein, "blocking group" refers to a substituent other than H that is conventionally coupled to oligomers or nucleomonomers, either as a protecting group, a coupling group for synthesis, $OPO_3^{-2}$, or other conventional conjugate such as a solid support, label, antibody, monoclonal antibody or fragment thereof and the like. As used herein, "blocking group" is not intended to be construed solely as a protecting group, according to slang terminology, but is meant also to include, for example, coupling groups such as a H-phosphonate or a phosphoramidite.

By "protecting group" is meant is any group capable of protecting the O-atom, S-atom or N-atom to which it is attached from participating in a reaction or bonding. Such protecting groups for N-atoms on a base moiety in a nucleomonomer and their introduction are conventionally known in the art. Non-limiting examples of suitable protecting groups include diisobutylformamidine, benzoyl and the like. Suitable "protecting groups" for O-atoms and S-atoms are, for example, DMT, MMT, FMOC or esters.

Protecting group

"Protecting group" as used herein includes any group capable of preventing the O-atom, S-atom or N-atom to which it is attached from participating in a reaction or bonding. Such protecting groups for O-, S- and N-atoms in nucleomonomers are described and methods for their introduction are conventionally known in the art. Protecting groups also include any group capable of preventing reactions and bonding at carboxylic acids, thiols and the like.

Coupling group

"Coupling group" as used herein means any group suitable for generating a linkage or substitute linkage between nucleomonomers such as a hydrogen phosphonate, a phosphoramidite and an alkyl ether.

Conjugate. "Conjugate" as used herein means any group attached to the oligomer at a terminal end or within the oligomer itself. Conjugates include solid supports, such as silica gel, controlled pore glass and polystyrene; labels, such as fluorescent, chemiluminescent, radioactive atoms or molecules, enzymatic moieties and reporter groups; oligomer transport agents, such as polycations, serum proteins and glycoproteins and polymers and the like.

Synthon

"Synthon" as used herein means a structural unit within a molecule that can be formed and/or assembled by known or conceivable synthetic operations.

Transfection

"Transfection" as used herein refers to any suitable method that for enhanced delivery of oligomers into cells.

Subject

"Subject" as used herein means a plant or an animal, including a mammal, particularly a human.

The present invention is based on the synthesis of oligomers comprising novel substitute linkages between one or more nucleomonomers and methods of their synthesis and use. Oligomers containing these substitute linkages not only bind to complementary target nucleic acid sequences, but also have a reduced negative charge, are stable to nuclease activity and are more lipophilic than oligomers with unmodified phosphodiester linkages. Because of these properties, the oligomers of the invention may be utilized in any oligomer-based diagnostic application, or as a research reagent. The linkages are shown as a series of dimer compounds in the following general structural formulas I through XI. The dimers are useful for incorporation of the substitute linkages into oligomers by solid-phase methods as described below. The structural formulas show the substitute linkages that comprise (i) a 5-, 6- or 7-member ring with the C2' and C3' positions of a modified sugar (usually a ribose or ribose analog) constituting part of the ring and (ii) a one, two or three atom bridge that links the ring to the adjacent nucleomonomer at the C4' position. The C2', C3', C4' and C7" positions are indicated in structural formula I.

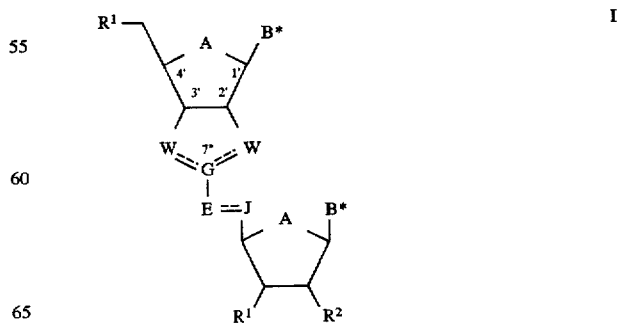

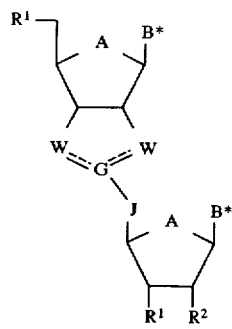
II
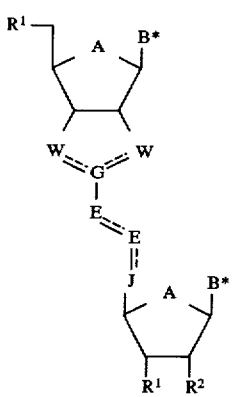
III
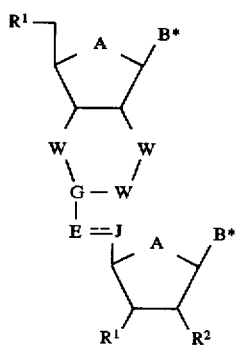
IV
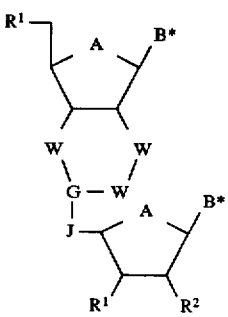
V
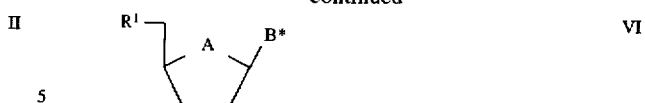
VI
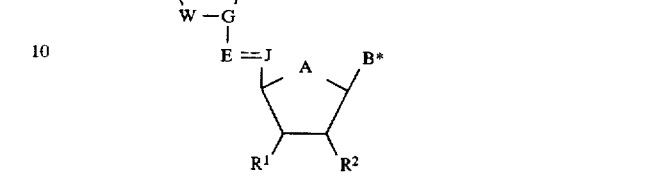
VII
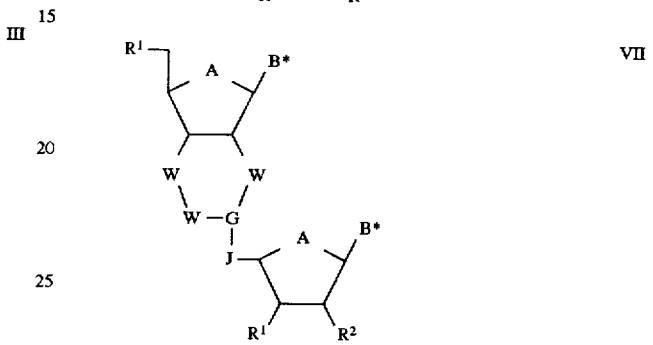
VIII
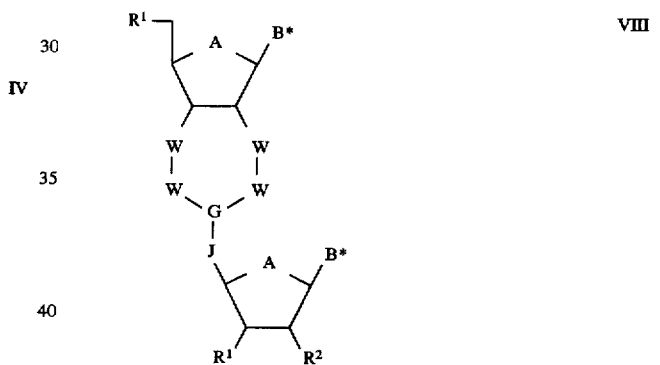
IX
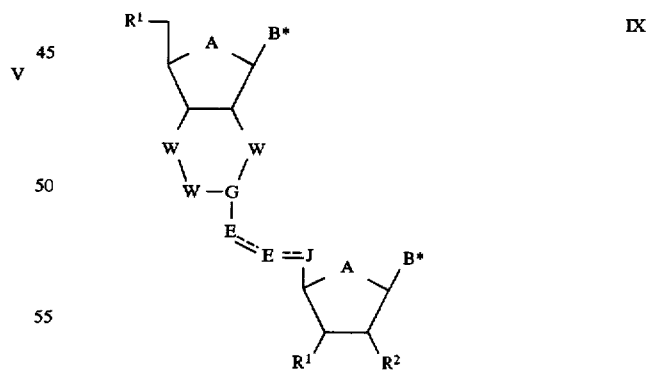

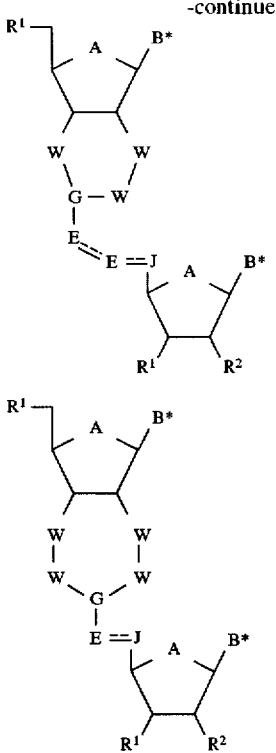

For each structure, $R^1$ is independently OH, $OpO_3^{-2}$, an oligomer, a solid support or a suitable blocking group such as a dimethoxytrityl ether (DMTO) moiety, a monomethoxytrityl ether (MMTO) moiety, an ester moiety, H-phosphonate ($OPO_2H$), methylphosphonate ($OPO_2CH_3$) or a phosphoramidite; $R^2$ is selected from the group consisting of H, OH, F, $NH_2$, $OCH_3$, $OC_2H_5$, $OCH_2CHCH_2$ (O-a2llyl, $OC_3H_5$), $OC_3H_7$ (O-propyl), $SCH_3$, $SC_2H_5$, $SCH_2CHCH_2$ (S-allyl, $SC_3H_5$), and $SC_3H_7$ (S-propyl). Methylphosphoramidite and β-cyanoethylphosphoramidite are preferred phosphoramidite groups.

Alternatively, for $R^1$ at C3' and $R^2$: when $R^2$ is part of an invention substitute linkage that is covalently linked to an adjacent nucleomonomer, $R^1$ and $R^2$ are W (defined below).

W is independently selected from the group consisting of O, S, SO, $SO_2$, $CH_2$, CH, CO, $CF_2$, CS, N, NH and $NR^3$ wherein $R^3$ is alkyl (1–4C, including methyl, ethyl, propyl, isopropyl, butyl or isobutyl) with the proviso that adjacent W (formulae IV–XI) are not —O—O—, —O—S—, —O—$CF_2$—, or —S—$CF_2$—, and provided that, for formula I, only one W is N or CH and when W is N or CH, W is connected to G by a double bond.

A is independently selected from the group consisting of O, S, $CH_2$, $CF_2$ and CFH (O is preferred).

E is selected from the group consisting of O, S, SO, $SO_2$, CH, $CH_2$, CO, $CF_2$, CS, N, NH, and $NR^3$ provided that no adjacent —E—E— are —O—O—, —O—S—, —S—O—, —O—$CF_2$— —$CF_2$—O—, —$CF_2$—S— or —S—$CF_2$—, and provided that when E is CH or N, any adjacent E is CH or N or an adjacent J is CH and they are connected by a double bond.

J is selected from the group consisting of O, S, SO, $SO_2$, CH, $CH_2$, CO, $CF_2$ and CS provided that no adjacent —E—J— are —O—O—, —O—S—, —S—O—, —$CF_2$—O—, —O—$CF_2$—, —$CF_2$—S— or —S—$CF_2$—, and provided that when J is CH, any adjacent E is CH or N and they are connected by a double bond.

G is independently selected from the group consisting of C, CH, N, CF, CCl, CBr, CI, and $CR^4$ wherein $R^4$ is lower alkyl (1–4C) or lower fluoroalkyl (1–4C, 1–6F, including fluoromethyl, difluoromethyl, trifluoromethyl, and hexafluoroisopropyl), 5-tetrazole, hydroxymethyl ($CH_2OH$), $CH_2$-(5-tetrazole), CN, $CO_2H$, $CO_2R^3$, $CONH_2$, $CONHR^3$, $CON(R^3)_2$, $CH_2SR^3$, $CH_2SOR^3$, $CH_2SO_2R^3$, $CH_2CO_2H$, $CH_2CN$, $CH_2CO_2R^3$, $CH_2CONH_2$, $CH_2CONHR^3$ and $CH_2CON(R^3)_2$, wherein $R^3$ is as defined above.

B* is a base. Bases (B*) that are preferred are adenine, thymine, guanine, cytosine, uracil, 8-oxo-$N^6$-methyladenine, $N^4,N^4$-ethanocytosine, 5-methylcytosine, 5-(1-propynyl)uracil, 5-(1-propynyl)cytosine, and 7-deazaxanthine. These base analogs are disclosed in commonly owned pending U.S. application serial no. 787,920, commonly owned International Application Nos. PCT/US91/08811 and PCT/US91/03680, and attorney docket no. 24610-20035.22 filed Nov. 24, 1992 (Froehler, B. C. et al, inventors), International Application Nos. PCT/US91/08811 and PCT/US91/03680, or disclosed in Application No. PCT/US90/03275.

Substitute linkages of the present invention also include 5-, 6-, or 7-member unsaturated rings with the proviso that both termini of the double bond G, are C or N. In addition, double bonds can be utilized in substitute linkages containing two or three atom bridges.

Preferred Embodiments

Oligomers having one or more substitute linkages of the 5-member ring series are preferred embodiments of the present invention. Preferred embodiments include oligomers having one or more substitute linkages of the 5-member ring series as shown in formula III. These embodiments include oligomers containing one or more substitute linkages of formula III where A is O, each W is independently O or S, J is $CH_2$, and G is CH or $CR^4$, and E adjacent to G is $CH_2$, and E adjacent to J is $CH_2$, O, S, SO or $SO_2$.

Oligomers containing one or more substitute linkages of formula I where each W is independently O or S, E is O, S or $CH_2$, J is $CH_2$, G is CH or $CR^4$ are also preferred embodiments. The riboacetal substitute linkage (structure I, where A and W are O, G is CH, and E, and J are $CH_2$) is a particularly preferred embodiment.

Preferred embodiments also include oligomers having one or more substitute linkages of the 5-member ring series as shown in formula II. These embodiments include oligomers containing one or more substitute linkages of formula II where A is O, each W is independently O or S, J is $CH_2$, and G is CH or $CR^4$.

Invention Oligomers

Oligomers containing substitute linkages of the invention are nuclease resistant and are capable of sequence-specific binding in the formation of duplexes or triplexes with single-stranded RNA or DNA or duplex target sequences, respectively.

When substitute linkages are present, additional nucleomonomer modifications can vary widely as discussed hereinafter. Preferably, the additional modification is the inclusion of at least one purine or pyrimidine analog in place of guanine, adenine, cytosine or thymine.

Substitute linkages of the present invention include 3-member rings formed through linking the C2' and C3' position of the modified sugar through (i) N which is linked through the three atom bridge -E-E-J- to the adjacent nucleotide and (ii) G which is linked through the three atom bridge -E-E-J- to the adjacent nucleomonomer.

It has been found that oligomers containing substitute linkages efficiently bind complementary single-stranded and double-stranded nucleic acid sequences. Triple helix structures were formed under physiological salt conditions. Oligomers of the present invention are generally characterized as containing one or more riboacetal or related substitute linkages. The substitute linkages may be utilized in oligomers that contain additional modifications of other nucleomonomers that comprise the oligomer. An exemplary list of such modifications include oligomers where (i) one or more nucleomonomer is modified at the 2' position, (ii) one or more crosslinking moieties have been incorporated, (iii) switchback linkers have been incorporated, (iv) other substitute linkages have been included and (v) bases that facilitate duplex or triplex formation, such as 8-oxo-$N^6$-methyladenine, 5-(1-propynyl)uracil, 5-(1-propynyl)cytosine or 7-deazaxanthine have been included. One or more of such modifications may advantageously be incorporated into a given oligomer depending on target nucleic acid sequences. The oligomers of the invention can be constructed to have any desired sequence and can be incorporated into pharmaceutically acceptable carriers. Compositions of the invention can used for diagnostic purposes in order to detect the presence of neoplastic growth, viruses and a variety of disease conditions.

The invention oligomers can also be utilized as research reagents to analyze the function of individual genes or to probe the function of nucleic acids in cells or cell extracts.

The invention is directed primarily to oligomers capable of duplex and triple-helix formation and, more specifically, to oligomers containing riboacetal, related substitute linkages and the novel nucleomonomers and dimers which serve as intermediates in the synthesis of such oligomers. These oligomers are preferably included in a carrier and can have any desired sequence which will be determined by the target sequence.

In another aspect, the invention is directed to DNA triplexes and a method to form such triplexes. The invention oligomers are suitable for hybridizing with DNA duplex targets via either CT or GT triplex binding motifs. Other aspects of the invention include pharmaceutical and diagnostic compositions which contain the oligomers of the invention and methods to diagnose and treat diseases characterized by various target sequences such as oncogene or virus duplexes using these compositions.

An additional aspect of the invention includes methods of detecting the presence, absence or amount of a particular single-stranded DNA or RNA or a particular target duplex in a sample using the oligomers of the invention. Such sequences can be associated with the presence of neoplastic growth, viruses or other disease conditions. Reagents and kits containing oligomers of the invention represent an aspect of the invention that permits facile use of the oligomers as reagents useful for (1) modulating gene expression in cells in vitro including cells grown in tissue culture, and (2) detecting and/or quantitating target sequences.

An advantage of the present invention is that the oligomers are capable of forming triplexes under physiological ion conditions.

Other advantages of oligomers containing the substitute linkages of the present invention compared to unmodified oligomers is that the substitute linkage may enhance cell permeation or uptake and such substitute linkages are stable to nuclease activity. These compounds are more lipophilic than native DNA. In addition, the substitute linkages disclosed herein eliminate the negative charge associated with phosphodiester linkages which can facilitate cell association or uptake. Nuclease stability is an important functional aspect of oligomers that modulate gene expression via, for example, an antisense mechanism.

An important feature of the oligomers of the present invention is that the substitute linkages are relatively rigid compared to diester linkages in native nucleic acids. This property contributes to the enhanced binding capacity of some of the invention oligomers.

Aspects of the invention include the use of nucleomonomers, two linked nucleomonomers (dimers), three linked nucleomonomers (trimers), four linked nucleomonomers (tetramers), five linked nucleomonomers (pentamers) or six linked nucleomonomers (hexamers) as intermediates in the synthesis of the longer oligomers of the invention. These oligomers are valuable synthons of the invention that are useful in the synthesis of longer oligomers.

An aspect of the invention includes methods for separation of endo and exo isomers at the G position. For invention substitute linkages, other than riboacetal linkages (FIGS. 1 and 15), synthesis of nucleomonomers linked by the substitute linkage usually leads to a mixture containing both isomers at the G position. Methods for separation of the endo and exo isomers are described below. When G is N or C, no stereoisomers are possible at this position. Methods for separation of endo and exo isomers include reverse phase HPLC and normal phase silica gel flash chromatography.

These and other objects, advantages and features of the invention will become apparent to those persons skilled in the art upon reading the details of the oligomers and their synthesis and usage as more fully set forth below, reference being made to the structural formulas and specific examples.
Additional Nucleomonomer Modifications Oligomers that are comprised of nucleomonomers can also contain various modifications in addition to the substitute linkages of the invention. A non-limiting exemplary list of such additional modifications includes oligomers where (i) one or more nucleomonomer residues are modified at the 2' position, (ii) one or more covalent crosslinking moieties are incorporated, (iii) inverted polarity linkers (switchback linkers) are incorporated, (iv) other noninvention substitute linkages are included, (v) other base analogs, such as 8-oxo-$N^6$-methyladenine, are included and (vi) conjugates such as intercalating agents or polylysine that respectively enhance binding affinity to target nucleic acid sequences or that enhance association of the oligomer with cells are included.

The binding competence of the invention oligomers for single-stranded and duplex targets is compatible with further modifications to the oligomer. These further modifications may also confer other useful properties such as stability to nuclease cleavage (e.g. in a domain of an invention oligomer having phosphodiester linkages), or enhance their ability to permeate cell membranes, and the like.

Also included are oligomers containing one or more substitute linkages such as sulfide or sulfone linkages (Benner, S. A., International Publication No. WO 89/12060), sulfamate linkages (International Publication No. WO 91/15500), carbamate or other substitute linkages in morpholino-linked oligomers (Stirchak, E. P. et al *Nucleic Acids Res* (1989) 17:6129–6141; Summerton, J., et al International Publication No. 216 860) and related linkages.

Thus, exemplary embodiments of invention oligomers include oligomers having (1) at least one substitute linkage and a 5-member or 6-member ring that is linked to an adjacent C4' atom through a one, two or three atom bridge, and (2) one or more non-invention substitute linkages selected from the group consisting of phosphorothioate, methylphosphonate and thionomethylphosphonate and/or (3) one or more phosphodiester linkages and/or (4) purine or pyrimidine analogs that enhance binding affinity for complementary target sequences. Other exemplary oligomers would include (1) an oligomer having invention substitute linkages at the 3' and/or 5' ends and phosphorothioate linkages elsewhere in the oligomer; (2) oligomers having invention substitute linkages and standard purine or pyrimidine bases (e.g. adenine, guanine, cytosine, thymine, or uracil); (3) oligomers having invention substitute linkages and one or more bases that enhance binding affinity or permeation competence of the oligomer (e.g. 5-methylcytosine, 5-(1-propynyl)uracil, 5-(1-propynyl) cytosine, and the like); and (4) oligomers having invention substitute linkages and one or more 2'-modified nucleomonomers (e.g. 2'-O-allyl, 2'-fluoro, and the like).

Related linkages such as amide linkages and 2',5' linkages are described in commonly owned pending U.S. application Ser. No. 07/889,736 filed Jan. 28, 1992, 07/892,902 filed Jun. 1, 1992, and 07/894,397 filed Jun. 5, 1992, each cited reference is incorporated herein by reference in its entirety.

Also included are oligomers containing nucleomonomer residues linked via amide bonds. Exemplary linkages have been described (Nielsen, P. E., et al, *Science* (1991) 254:1497–1500; commonly owned copending U.S. application Ser. Nos. 07/889,736, filed Jan. 28, 1992, and 07/894, 397, filed Jun. 5, 1992, both incorporated herein by reference).

Oligomers

The oligomers of the invention can be formed using invention and conventional nucleomonomers and synthesized using standard solid phase (or solution phase) oligomer synthesis techniques, which are now commercially available. In general, the invention oligomers can be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention can be of any length including those of greater than 40, 50 or 100 nucleomonomers. In general, preferred oligomers contain 2–30 nucleomonomers. Lengths of greater than or equal to about 8 to 20 nucleomonomers are useful for diagnostic applications. Short oligomers containing 2, 3, 4 or 5 nucleomonomers are specifically included in the present invention and are useful as synthons.

Oligomers having a randomized sequence and containing about 6, 7 or 8 nucleomonomers are useful for primers that are used in cloning or amplification protocols that use random sequence primers, provided that the oligomer contains about 1 or 2 residues at the 3' end that can serve as a primer for polymerases or reverse transcriptases or that otherwise do not interfere with polymerase activity.

Oligomers can contain conventional phosphodiester linkages or can contain other non-invention substitute linkages such as phosphoramidate linkages in addition to the invention substitute linkages. These substitute linkages include, but are not limited to, embodiments wherein a moiety of the formula —O—P(O)(S)—O—("phosphorothioate"), —O—P (S)(S)—O—("phosphorodithioate"), —O—P(O)(NR'$_2$)— X—, —O—P(O)(R')—O—, —O—P(S)(R')—O— ("thionoalkylphosphonate"), —P(O)(OR$^6$)—X—, —O—C (O)—X—, or —O—C(O)(NR'$_2$)—X—, wherein R' is H (or a salt) or alkyl (1–12C including methyl and ethyl) and R$^6$ is alkyl (1–9C) and the linkage is joined to adjacent nucleomonomers through an —O— or —S— bonded to a carbon of the nucleomonomer. Phosphorothioate and phosphodiester linkages are well known. Particularly preferred substitute linkages for use in the oligomers of the present invention include phosphodiester, phosphorothioate, methylphosphonate and thionomethylphosphonate substitute linkages. Phosphorothioate and methylphosphonate substitute linkages confer added stability to the oligomer in physiological environments. While not all such substitute linkages in the same oligomer need be identical, particularly preferred oligomers of the invention contain one or more phosphorothioate or methylphosphonate substitute linkages.

Acceptable Salts

Any Acceptable salt can be used and such salt forming materials are well known in the art.

Pharmaceutically acceptable salts are preferably metal or ammonium salts of the oligomers of the invention and include alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amides, lower alkylenediamines or lower (hydroxyalkyl or arylalkyl)- alkylammonium bases, e.g. methylamine, diethylamine, triethylamine, dicyclohexylamine, triethanolamine, ethylenediamine, tris-(hydroxymethyl)-aminomethane or benzyltrimethylammonium hydroxide. The oligomers of the invention form acid addition salts, which are preferably such inorganic or organic acids, such as strong mineral acids, for example hydrohalic, e.g., hydrochloric or hydrobromic acid; sulfuric, phosphoric; aliphatic or aromatic carboxylic or sulfonic acids, e.g., formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, methanesulfonic, ethanesulfonic, hydroxyethanesulfonic, benzenesulfonic, sulfanilic or cyclohexylsulfamic acid and the like.

Blocking Groups

1. Coupling Groups.

Figure 2:
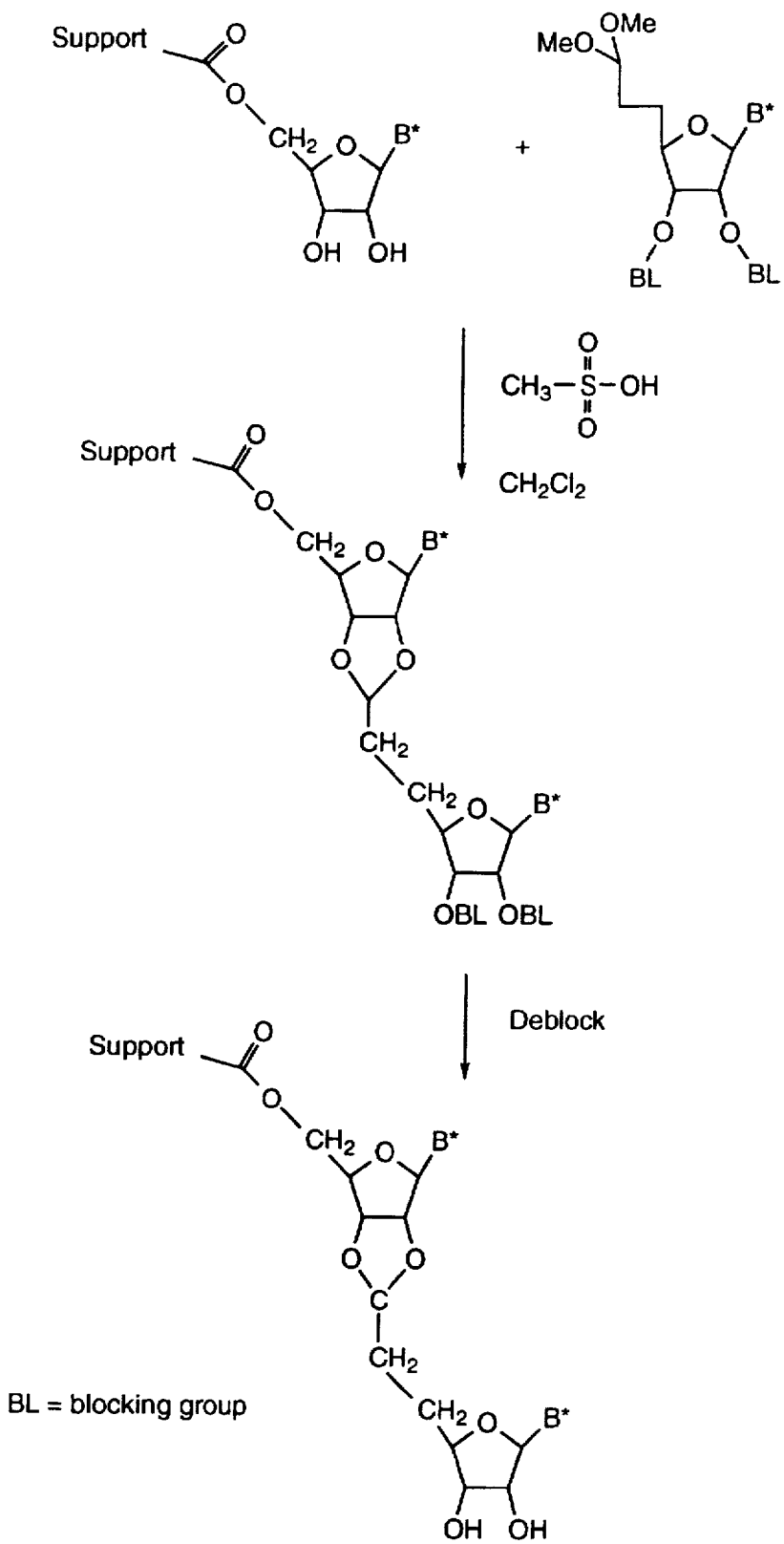
FIG. 2 describes the solid phase generation of a homopolymer of Example 4.

Suitable coupling groups are, for example, H-phosphonate, a methylphosphonamidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 25-1 and 25-2.

Figure 4:
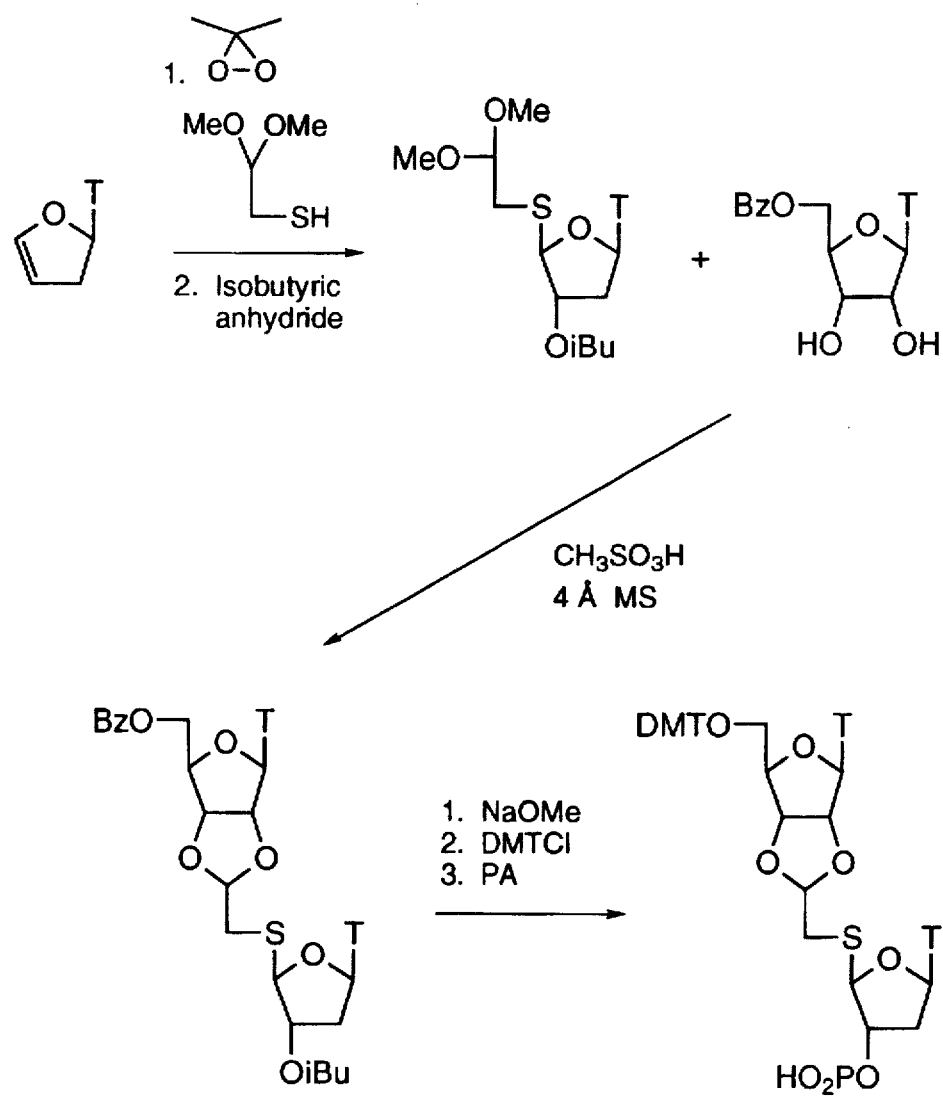
FIG. 4 describes the synthesis of a 5'-DMT thioriboacetal synthon of Example 6.

Suitable "coupling groups" at the 3', 2' or 5' position for oligomer synthesis via phosphoramidite triester chemistry, referred to herein as "amidite" chemistry, include N,N-diisopropylamino-β-cyanoethoxyphosphine, N,N-diisopropylamino-methoxyphosphine, N,N-diethylamino-β-cyanoethoxyphosphine, (N-morpholino)-β-cyanoethoxyphosphine, and (N-morpholino)-methoxyphosphine (Moore, M. F. et al, *J Org Chem* (1985) 50:2019–2025; Uznanski, A. W., et al, *Tet Lett* (1987) 28:3401–3404; Bjergarde, K., et al, *Nucl Acids Res* (1991) 21:5843–5850; Dahl, O. *Sulfur Reports* (1991) 11:167–192). Related coupling groups such as N,N-diisopropylamino-methyl-phosphine or N,N-diethylamino-methyl-phosphine can also be used to prepare methylphosphonates (FIG. 25-4). Methylphosphonate oligomers can be conveniently synthesized using coupling groups such as N,N-diisopropylamino-methylphosphonamidite, and N,N-diethylamino-methylphosphonamidite. Synthesis of nucleomonomer amidites of the invention can be accomplished by conventional methods (for example, Gryaznov, S. M., et al, *Nucl Acids Res* (1992) 20:1879–1882; Vinayak, R., et al, *Nucl*

*Acids Res* (1992) 20:1265–1269; Sinha, N. D., et al, *Nucl Acids Res* (1984) 12:4539–4557; and other references cited herein).

Figure 15:
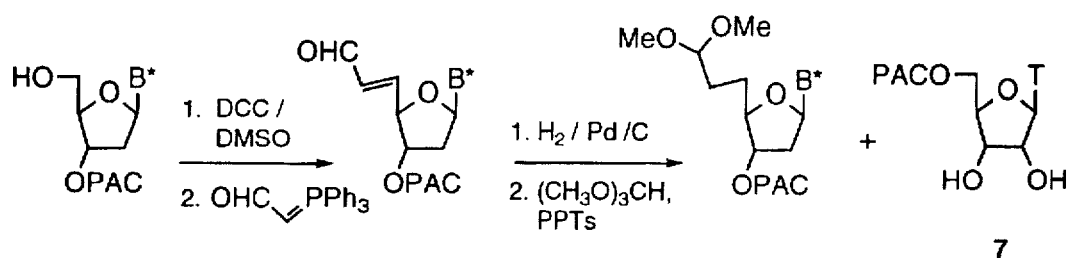
FIG. 15 describes the synthesis of a riboacetal synthon of Example 17.
Figure 15:
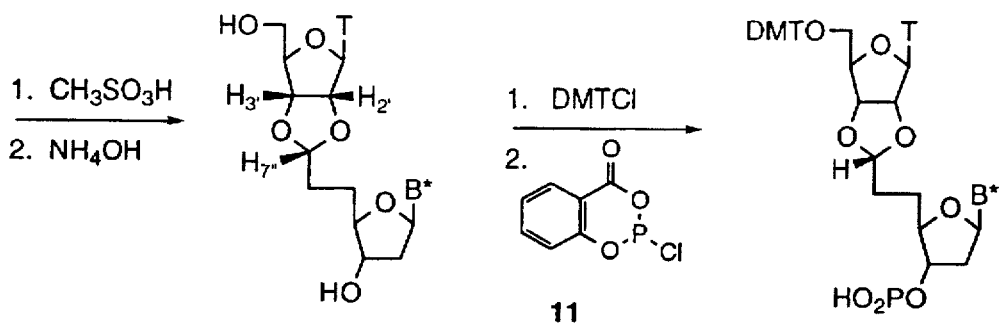
Figure 15:
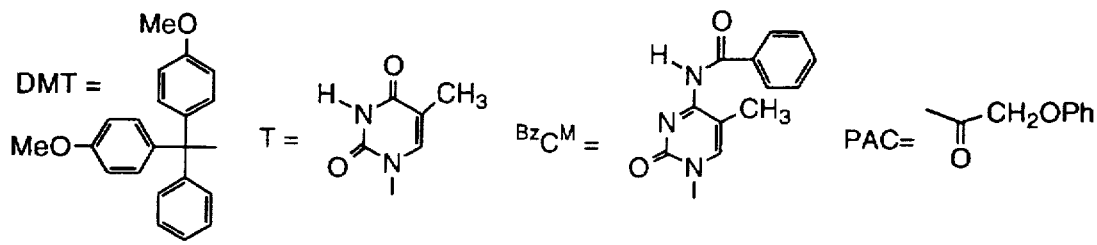

Suitable coupling groups at the 3', 2' (or 5') position for oligomer synthesis via phosphate triester chemistry, referred to herein as "triester" chemistry, include 2-chlorophenyl phosphate, 4-chlorophenyl phosphate, 2,4-dichlorophenyl phosphate and 2,4,-dibromophenyl phosphate nucleotide diester derivatives or, for synthesis of phosphorothioate linkages, the thiono derivatives thereof (Marugg, J. E., et al, *Nucl Acids Res* (1984) 12:9095–9110; Kemal, O., et al, *J Chem Soc Chem Commun* (1983) 591–593; Kamer, P. C. J., et al, *Tet Lett* (1989) 30:6757–6760). Structures of these coupling groups are shown in FIG. 15 where X is O or S and $Z^1$ is H or a suitable benzotriazole.

2. Protecting Groups.

Protecting groups such as diisobutylformamidine, benzoyl, isobutyryl, FMOC, dialkylformamidine, dialkylacetamidine or other groups known in the art can be used to protect the exocyclic nitrogen of the cytosine, adenine or guanine heterocycles. Alternatively, cytidine can be directly incorporated into oligomers without a protecting group at the exocyclic nitrogen using described methods (Gryaznov, S. M. et al, *J Amer Chem Soc* (1991) 113:5876–5877; Gryaznov, S. M., et al, *Nucl Acids Res* (1992) 20:1879–1882; Kung, P. -P., et al, *Tetrahedron Letters* (1992) 40:5869–5872).

Suitable protecting groups are DMT (dimethoxy trityl), Bz (benzoyl), iBu (isobutyryl), phenoxyacetyl, MMT (monomethoxytrityl) or FMOC at the 5' terminus and/or hydrogen phosphonate, methyl phosphoramidite, methyl phosphonamidite, β-cyanoethylphosphoramidite, TBS (t-butyldimethylsilyl) or TBDPS (t-butyldiphenylsilyl) at the 3'-terminus.

Preferred protecting groups are Bz (benzoyl), DMT (dimethoxytrityl), MMT (monomethoxytrityl) or FMOC at the 5' terminus or position and/or TBS, hydrogen phosphonate, methylphosphoramidite, methylphosphonamidite, β-cyanoethylphosphoramidite at the 3'-terminus. However, it is intended that the position of the blocking groups can be reversed as needed (e.g., a phosphoramidite at the 5'-position and DMT at the 3'-position). In general, the nucleomonomers and oligomers of the invention can be derivatized to such "blocking groups" as indicated in the relevant formulas by methods known in the art.

Conjugates

Also included are "conjugates" of oligomers. "Conjugates" of the oligomers include those conventionally recognized in the art. For instance, the oligomers can be covalently linked to various moieties such as, intercalators, and substances which interact specifically with the minor groove of the DNA double helix. Other chosen conjugate moieties, can be labels such as radioactive, fluorescent, enzyme, or moieties which facilitate cell association using cleavable linkers and the like. Suitable radiolabels include $^{32}P$, $^{35}S$, $^3H$ and $^{14}C$; and suitable fluorescent labels include fluorescein, resorufin, rhodamine, BODIPY (Molecular Probes) and texas red; suitable enzymes include alkaline phosphatase and horseradish peroxidase. Other compounds which can be used as covalently linked moieties include biotin, antibodies or antibody fragments, transferrin and the HIV Tat protein can also conveniently be linked to the oligomers of the invention.

These additional moieties can be derivatized through any convenient moiety. For example, intercalators, such as acridine or psoralen can be linked to the oligomers of the invention through any available—OH or —SH, e.g., at the terminal 5'-position of the oligomer, the 2'-positions of RNA, or an OH, NH$_2$, COOH or SH incorporated into the 5-position of pyrimidines. A derivatized form which contains, for example, —CH$_2$CH$_2$NH$_2$, —CH$_2$CH$_2$CH$_2$OH or —CH$_2$CH$_2$CH$_2$SH in the 5-position of pyrimidines is convenient. Conjugates including polylysine or lysine can be synthesized as described and can further enhance the binding affinity of an oligomer to its target nucleic acid sequence (Lemaitre, M. et al., *Proc Natl Acad Sci* (1987) 84:648–652; Lemaitre, M. et al., *Nucleosides and Nucleotides* (1987) 6:311–315).

A wide variety of substituents can be attached, including those bound through linkages or substitute linkages. The -OH moieties in the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'-OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Linkers used for such conjugates can include disulfide linkages that are reduced after the oligomer-transport agent conjugate has entered a cell. Appropriate molecular linkers include for example, —$Y^1$—$X^8CH_2CHR^7$—SS—$CHR^7CH_2X^8$—$Y^1$— wherein each $Y^1$ is independently alkylene (1–9C; including methylene, ethylene and propylene), or CO, each $X^8$ is independently O, S(O)(O), S(O), $NR^7$, $CH_2$, $C(R^7)_2$ or CO; $R^7$ wherein each $R^7$ is independently H, alkyl (1–6C; including methyl, ethyl and propyl), or aryl and which linkers have been previously described (International Publication No. WO 91/14696). Disulfide-containing linkers of this type have a controllable $t_{1/2}$ in vivo, facilitating its use as a /transport component. Such linkers are stable under extracellular conditions relative to intracellular conditions due to the redox potential of the disulfide linkage.

Suitable conjugates also include solid supports for oligomer synthesis and to facilitate detection of nucleic acid sequences. Solid supports include, but are not limited to, silica gel, controlled pore glass, polystyrene, and magnetic glass beads.

Sugar Modifications

Derivatives can be made by substitution on the sugars. Among the preferred derivatives of the oligomers of the invention are the 2'-O-allyl derivatives. The presence of the 2'-O-allyl group appears to enhance permeation ability and stability to nuclease degradation, but does not appear to diminish the affinity of the oligomer for single chain or duplex targets.

Furthermore, as the α anomer binds to duplex DNA or single-stranded RNA in a manner similar to that for the β anomers but with a reversed polarity, oligomers can contain nucleomonomers having this epimer or a domain thereof (Praseuth, D., et al., *Proc Natl Acad Sci* (USA) (1988) 85:1349–1353; Sun, J. S. et al, *Proc Natl Acad Sci* (1991) 88:6023–6027; Debart, F., et al, *Nucl Acids Res* (1992) 20:1193–1200). α-Anomeric oligomers containing the substitute linkages described herein represent a class of modified oligomers included in the present invention.

Noninvention Substitute Linkages

The oligomers of the invention can also contain one or more "substitute linkages", in addition to those disclosed herein, which are generally understood in the art. These "substitute linkages" include phosphorothioate, methylphosphonate, thionomethylphosphonate, phosphorodithioate, 2',5' linkages, alkylphosphonates, morpholino carbamate, morpholino sulfamate, morpholino sulfamide, boranophosphate (—O—P(OCH$_3$)(BH$_3$)—O—), siloxane (—O—Si(X$^4$)(X$^4$)—O—; X$^4$ is alkyl or phenyl) and phosphoramidate (methoxyethylamine (—O—P(OCH$_2$CH$_2$OCH$_3$)(O)—O—) and the like), and are synthesized as described in the generally available literature including the following references (Sood, A., et al, *J Am Chem Soc* (1990) 112:9000–9001; WO 91/08213; WO 90/15065; WO 91/15500; Stirchak, E. P. et al *Nucleic Acid Res* (1989) 17:6129–6141; U.S. Pat. No. 5,034,506; U.S. Pat. No. 5,142,047; Hewitt, J. M. et al, *Nucleosides and Nucleotides* (1992) 11:1661–1666; Summerton, J., et al International Publication No. 216 860). Substitute linkages that can be used in the oligomers disclosed herein also include the sulfonamide (—O—SO$_2$—NH—), sulfide (—CH$_2$—S—CH$_2$—), sulfonate (—O—SO$_2$—CH$_2$—), carbamate (—O—C(O)—NH—, —NH—C(O)—O—), dimethylhydrazino (—CH$_2$—NCH$_3$—NCH$_3$—), sulfamate (—O—S(O)(O)—N—; —N—S(O)(O)—N—), 3'-thioformacetal (—S—CH$_2$—O—), formacetal (—O—CH$_2$—O—), 3'-amine (—NH—CH$_2$—CH$_2$—), N-methylhydroxylamine (—CH$_2$—NCH$_3$—O—) and 2'5' linkages (such as 2',5' carbamate (2' —N(H)—C(O)—O— 5'), 5',2' carbamate (2' —O—C(O)—N(H)— 5'), 5',2' methylcarbamate (2' —O—C(O)—N(CH$_3$)— 5') and 5',2' thioformacetal (2' —O—CH$_2$—S— 5'). 2',5' linkages are disclosed in pending U.S. application Ser. No. 07/892,902, filed Jun. 1, 1992, incorporated herein by reference). Substitute linkages are disclosed and claimed in commonly owned pending U.S. patent application Ser. No. 690,786, filed Apr. 24, 1991, and 763,130, filed Sep. 20, 1991, incorporated herein by reference in their entirety. Additional substitute linkages that are suitable include amide linkages described by Buchardt, O. et al, (International Publication No. WO 92/20702), and those described by Cook, P. D. et al, (International Publication No. WO 92/20822), and De Mesmaeker, A. et al, (International Publication No. WO 92/20823).

Except where specifically indicated, the substitute linkages, such as a formacetal linkage, —O—CH$_2$—O—, are linked to either the 3' or 2' carbon of a nucleomonomer on the left side and to the 5' carbon of a nucleomonomer on the right side. Thus a formacetal linkage can be indicated as 3' —O—CH$_2$—O— 5' or 2' —O—CH$_2$—O— 5'. The designations of a 3', 2' or 5' carbon can be modified accordingly when a structure other than ribose, deoxyribose or arabinose is linked to an adjacent nucleomonomer. Such structures include a hexose, morpholino ring, carbocyclic ring (e.g. cyclopentane) and the like.

The use of carbamate, carbonate, sulfide, sulfoxide, sulfone, N-methylhydroxylamine and dimethylhydrazino linkages in synthons or oligomers has been described (Vaseur, J.-J. et al, *J Amer Chem Soc* (1992) 114:4006–4007; WO 89/12060; Musicki, B. et al, *J Org Chem* (1990) 55:4231–4233; Reynolds, R. C., et al *J Org Chem* (1992) 57:2983–2985; Mertes, M. P., et al, *J Med Chem* (1969) 12:154–157; Mungall, W. S., et al, *J Org Chem* (1977) 42:703–706; Stirchak, E. P., et al, *J Org Chem* (1987) 52:4202–4206; Wang, H., et al, *Tet Lett* (1991) 50:7385–7388; International Application No. PCT US91/03680). Substitute linkage(s) can be utilized in the oligomers for a number of purposes such as to further facilitate binding with complementary target nucleic acid sequences and/or to increase the stability of the oligomers toward nucleases.

Nucleosides

Exemplary nucleosides suitable for synthesis of amide linked nucleomonomers have been described (Nielsen, P. E. ibid; Buchardt, O. et al, International Publication No. WO 92/20702; commonly owned copending U.S. application Ser. Nos. 07/889,736, filed Jan. 28, 1992, and 07/894,397, filed Jun. 5, 1992, all applications incorporated herein by reference in their entirety).

"Nucleosides" also include those moieties which contain modifications of the sugar, for example, wherein one or more of the hydroxyl groups are replaced with halogen, aliphatic groups, or functionalized as ethers, amines, and the like. Such structures include a hexose, morpholino ring, carbocyclic ring (e.g. cyclopentane) and the like.

Base

Suitable bases for use within the present invention include not only the known purine and pyrimidine bases, but also analogs of these heterocyclic bases and tautomers thereof. Such analogs include alkylated purines or pyrimidines, acylated purines or pyrimidines, or other heterocycles. Such "analogous purines" and "analogous pyrimidines" or purine or pyrimidine analogs are those generally known in the art, some of which are used as chemotherapeutic agents. An exemplary, but not exhaustive, list includes $N^4, N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, inosine, $N^6$-isopentenyl-adenine, 1-methyladenine, 2-methylguanine, 5-methylcytosine, $N^6$-methyladenine, 7-methylguanine, 5-methylaminomethyl uracil, 5-methoxy aminomethyl-2-thiouracil, 5-methoxyuracil, pseudouracil, 5-methyl-2-thiouracil, 2-thiouracil, 4-thiouracil, 5-(1-propynyl)-4-thiouracil, 5-(1-propynyl)-2-thiouracil, 5-(1-propynyl)2-thiocytosine, 2-thiocytosine, and 2,6-diaminopurine. In addition to these base analogs, pyrimidine analogs including 6-azacytosine, 6-azathymidine and 5-trifluoromethyluracil described in Cook, D. P., et al, International Publication No. WO 92/02258 (incorporated herein by reference) can be conveniently incorporated into the invention oligomers.

Incorporation of 4-thiouridine and 2-thiothymidine into oligomers has been described (Nikiforov, T. T., et al, *Tet Lett* (1992) 33:2379–2382; Clivio, P., et al *Tet Lett* (1992) 33:65–68; Nikiforov, T. T., et al, *Tet Lett* (1991) 32:2505–2508; Xu, Y. -Z., et al *Tet Lett* (1991) 32:2817–2820; Clivio, P., et al *Tet Lett* (1992) 33:69–72; Connolly, B. A., et al., *Nucl. Acids Res.* (1989) 17:4957–4974).

Preferred bases include adenine, guanine, thymine, uracil, cytosine, 5-methylcytosine, 5-(1-propynyl)uracil, 5-(1-propynyl)cytosine, 8-oxo-$N^6$-methyladenine, and 7-deazaxanthosine. Synthesis and use of oligomers that bind to duplex DNA sequences via GT binding motif containing 7-deazaxanthosine is described in commonly owned pending U.S. application Ser. No. 07/787,920, filed Nov. 7, 1991, which is incorporated herein by reference in its entirety.

Covalent Bonding Moiety

Included in some of the oligomers of the invention is a moiety which is capable of effecting at least one covalent bond between the oligomer and the duplex. Multiple covalent bonds can also be formed by providing a multiplicity of such crosslinking moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand. Crosslinking moieties are disclosed and claimed in commonly owned pending application Ser. No. 640,654.

In one embodiment of the invention, a switchback oligonucleotide containing crosslinking moieties at either end can be used to bridge the strands of the duplex with at least two covalent bonds. In addition, nucleotide sequences of inverted polarity can be arranged in tandem with a multiplicity of crosslinking moieties to strengthen the complex. Exemplary of crosslinking moieties that are useful in the invention include $N^4,N^4$-ethanocytosine and $N^6,N^6$-ethanoadenine.

It is clear that the heterocycle need not be a purine or pyrimidine; indeed the pseudo-base to which the reactive function is attached need not be a heterocycle at all. Any means of attaching the reactive group is satisfactory so long as the positioning is correct.

Inverted Polarity

In their most general form, inverted polarity oligomers, that can incorporate one or more nucleomonomers described above, contain at least one segment along their length of the formula:

(1)

or

(2)

where —C— symbolizes any method of coupling the nucleomonomer sequences of opposite polarity (Froehler, B. C., et al *Biochemistry* (1992) 31:1603–1609; Horne, D. A., et al *J Am Chem Soc* (1990) 112:2435–2437; Beal, P. A., et al *J Am Chem Soc* (1992) 114:4976–4978).

In these formulas, the symbol 3'----5' indicates a stretch of oligomer in which the linkages are consistently formed between the 5'-hydroxyl of the ribosyl residue of the nucleomonomer to the left with the 3'-(or 2'- for oligomers having 2', 5' linkages) hydroxyl of the ribosyl residue of the nucleomonomer to the right (i.e., a region of uniform polarity), thus leaving the 5'-hydroxyl of the rightmost nucleomonomer ribosyl residue free for additional conjugation. Analogously, 5'----3' indicates a stretch of oligomer in the opposite orientation wherein the linkages are formed between the 3'-hydroxyl of the ribosyl residue of the left nucleomonomer and the 5'-hydroxyl of the ribosyl residue of the nucleomonomer on the right, thus leaving the 3'-hydroxyl of the rightmost nucleomonomer ribosyl residue free for additional conjugation.

The linkage, symbolized by —C—, can be formed so as to link the 5'-hydroxyls of the adjacent ribosyl residues in formula (1) or the 3' hydroxyls of the adjacent ribosyl residues in formula (2), or the "—C—" linkage can conjugate other portions of the adjacent nucleomonomers so as to link the inverted polarity strands. "—C—" can represent a linker moiety, or simply a covalent bond.

It should be noted that if the linkage between strands of inverted polarity involves a sugar residue, either the 3'- or 2'-position can be involved in the linkage, and either of these positions can be in either R or S configuration. The choice of configuration will in part determine the geometry of the oligomer in the vicinity of the linkage. Thus, for example, if adjacent 3'-positions are used to effect a covalent linkage, less severe deformation of the oligomer chain will generally occur if both 3'-hydroxyls involved in the linkage are in the conventional R configuration. If they are both in the S configuration, this will result in a favorable "kink" in the chain.

In addition to the use of standard oligonucleotide synthesis techniques or other couplings to effect the 5'—5' or 3'—3' linkage between ribosyl moieties, alternative approaches to joining the two strands of inverted polarity can be employed. For example, the two appended bases of the opposing termini of the inverted polarity oligomer sequences can be linked directly or through a linker, or the base of one can be linked to the sugar moiety of the other. Any suitable method of effecting the linkage can be employed. The characterizing aspect of the switchback oligomers of the invention is that they comprise tandem regions of inverted polarity, so that a region of 3'→5' polarity is followed by one of 5'→3' polarity, or vice versa, or both.

Depending on the manner of coupling the segments with inverted polarity, this coupling can be effected by insertion of a dimer wherein the appropriate 3'-positions of each member of the dimer or the 5'-positions of each member of the dimer are activated for inclusion of the dimer in the growing chain, or the conventional synthesis can be continued using the condensing nucleomonomer which is blocked in the inverse manner to that which would be employed if the polarity of the chain were to remain the same. This additional nucleomonomer can also contain a linker moiety which can be included before or after condensation to extend the chain.

The synthesis of oligomers having inverted polarity can be accomplished utilizing standard solid phase synthesis methods.

In general, there are two commonly used solid phase-based approaches to the synthesis of oligomers containing conventional 3'→5' or 5'→3' linkages, one involving intermediate phosphoramidites and the other involving intermediate phosphonate linkages.

In the phosphoramidite based synthesis, a suitably protected nucleomonomer having a cyanoethylphosphoramidite at the position to be coupled is reacted with the free hydroxyl of a growing nucleomonomer chain derivatized to a solid support. The reaction yields a cyanoethylphosphite, which linkage must be oxidized to the cyanoethylphosphate at each intermediate step, since the reduced form is unstable to acid.

The H-phosphonate-based synthesis is conducted by the reaction of a suitably protected nucleomonomer containing an H-phosphonate moiety at a position to be coupled with a solid phase-derivatized nucleomonomer chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligomer or after synthesis of the oligomer is complete. The H-phosphonates can also be converted to phosphoramidate derivatives by reaction with a primary or secondary amine in the presence of carbon tetrachloride. To indicate the two approaches generically, the incoming nucleomonomer is regarded as having a "coupling phosphite/phosphate" group.

Variations in the type of substitute linkage are achieved by, for example, using the methyl phosphonate precursors rather than the H-phosphonates per se, using thiol derivatives of the nucleomonomer moieties and generally by methods known in the art. Nonphosphorous based linkages such as the formacetal 3'-thioformacetal, 3'-amino and 5'-ether type linkages described above can also be used.

Thus, to obtain an oligomer segment which has a 3'→5' polarity, a nucleomonomer protected at the 5'-position and containing a coupling phosphite/phosphate group at the 3'-position is reacted with the hydroxyl at the 5'-position of a nucleomonomer coupled to a solid support through its 3'-hydroxyl. The resulting condensed oligomer is deprotected and the reaction repeated with an additional 5'-protected, 3'-phosphite/phosphate coupling nucleomonomer. Conversely, to obtain an oligomeric segment of 5'→3' polarity, a nucleomonomer protected in the 3'-position and containing a coupling phosphite/phosphate in the 5'-position is reacted with a oligomer or nucleomonomer attached to a solid support through the 5'-position, leaving the 3'-hydroxyl available to react. Similarly, after condensation of the incoming nucleomonomer, the 3'-group is deprotected and reacted with an additional 3'-protected, 5'-coupling nucleomonomer. The sequence is continued until the desired number of nucleomonomers have been added.

This oligomer chain elongation will proceed in conformance with a predetermined sequence in a series of condensations, each one of which results in the addition of another nucleomonomer. Prior to the addition of a nucleomonomer having a coupling phosphite/phosphate, the protecting group on the solid support-bound nucleomonomer is removed. Typically, for example, removal of the commonly-employed dimethoxytrityl (DMT) group is done by treatment with 2.5% v/v dichloroacetic acid/dichloromethane, although 1% w/v trichloroacetic acid/dichloromethane or ZnBr$_2$-saturated nitromethane, are also useful. Other deprotection procedures suitable for other protecting groups will be apparent to those of ordinary skill in the art. The deprotected nucleomonomer or oligomer bound to solid support is then reacted with the suitably protected nucleomonomer containing a coupling phosphite/phosphate. After each cycle the carrier bound nucleomonomer is preferably washed with anhydrous pyridine/acetonitrile (1:1, v/v), again deprotected, and the condensation reaction is completed in as many cycles as are required to form the desired number of congruent polarity internucleoside bonds which will be converted to phosphoramidates, phosphorodithioates, phosphorothioates or phosphodiesters as desired.

In one embodiment, to provide the switchback linker, the incoming coupling, protected nucleomonomer is provided in the opposite polarity to the support-bound oligomers. Thus, for example, where the support-bound oligomer is 3'→5', the deprotected 5'-hydroxyl is reacted with a 3'-protected, 5'-coupling monomer, and the synthesis continued with monomers coupled at the 5'-position and protected at the 3'-position.

In another embodiment, to provide the switchback linker, a dimer synthon containing the linker element having one end which is coupled for condensation (such as a hydrogen phosphonate) to the support-bound oligomer and another end which is a protected hydroxyl group (or protected thio group) is condensed onto the support-bound oligomer. The linked dimer is condensed and deprotected using the same conditions as those used to condense and deprotect the protected nucleomonomer hydrogen phosphonate. Subsequent extension of the oligomer chain then uses nucleomonomer residues which are coupled and protected in the opposite manner from those used to synthesize the previous portion of the chain.

One approach to this synthesis, using a linker already derivatized to two nucleomonomer residues which will be included in each portion of the strand is illustrated as follows. The 5'→3' nucleomonomer portion of the strand is coupled using the 3'-DMT-5'-coupling phosphate nucleomonomers, as conventionally, to solid support. The switchback linker is derivatized to two nucleomonomer residues through their 3'-positions; the remaining 5'-positions are derivatized by the protecting group DMT in one nucleomonomer residue and a phosphonate residue in the other. The derivatized linker is coupled to the solid supported strand under standard reagent conditions and then deprotected conventionally. Further standard nucleomonomer coupling results in extension of the chain in the 3'→5' orientation.

Figure 26:
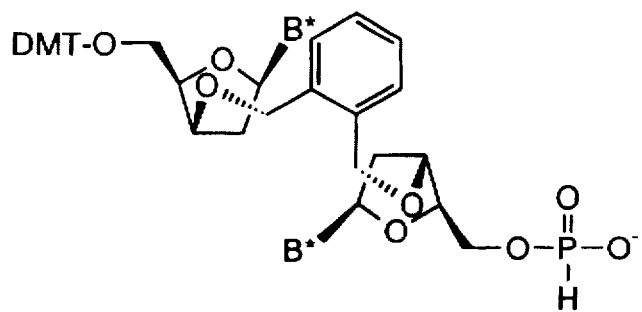
FIG. 26 shows structures of an o-xyloso switchback linker and representative noninvention substitute linkages that may be included in the oligomers of the invention.
Figure 26:
Figure 26:
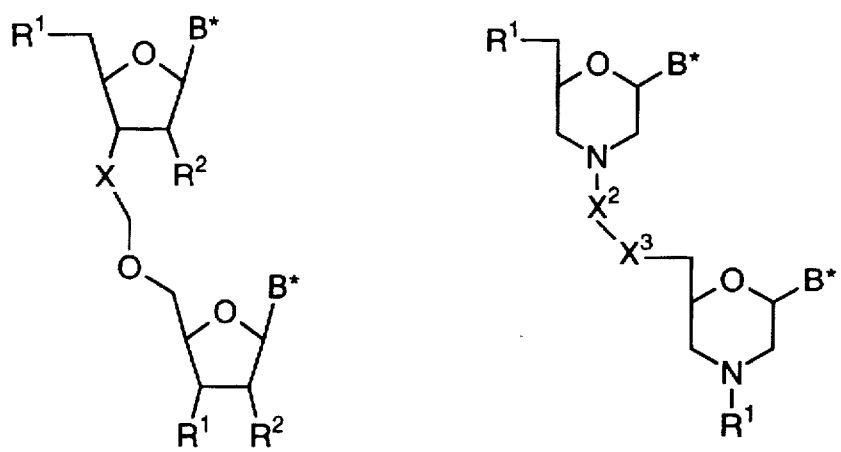
Figure 27A:
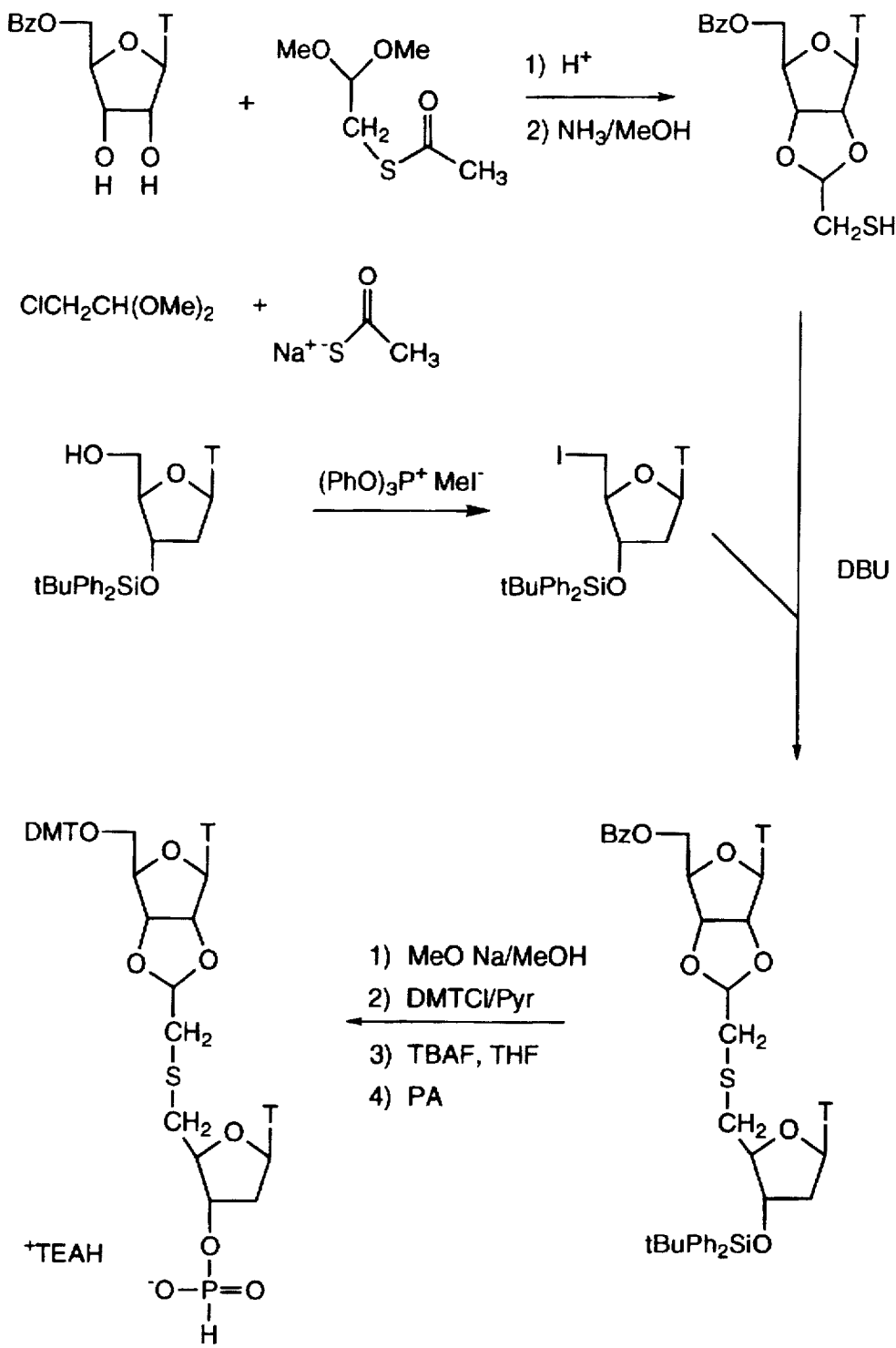
FIGS. 27-A to 27-B show synthesis of a five member ring with a 3 atom bridge.
Figure 27B:
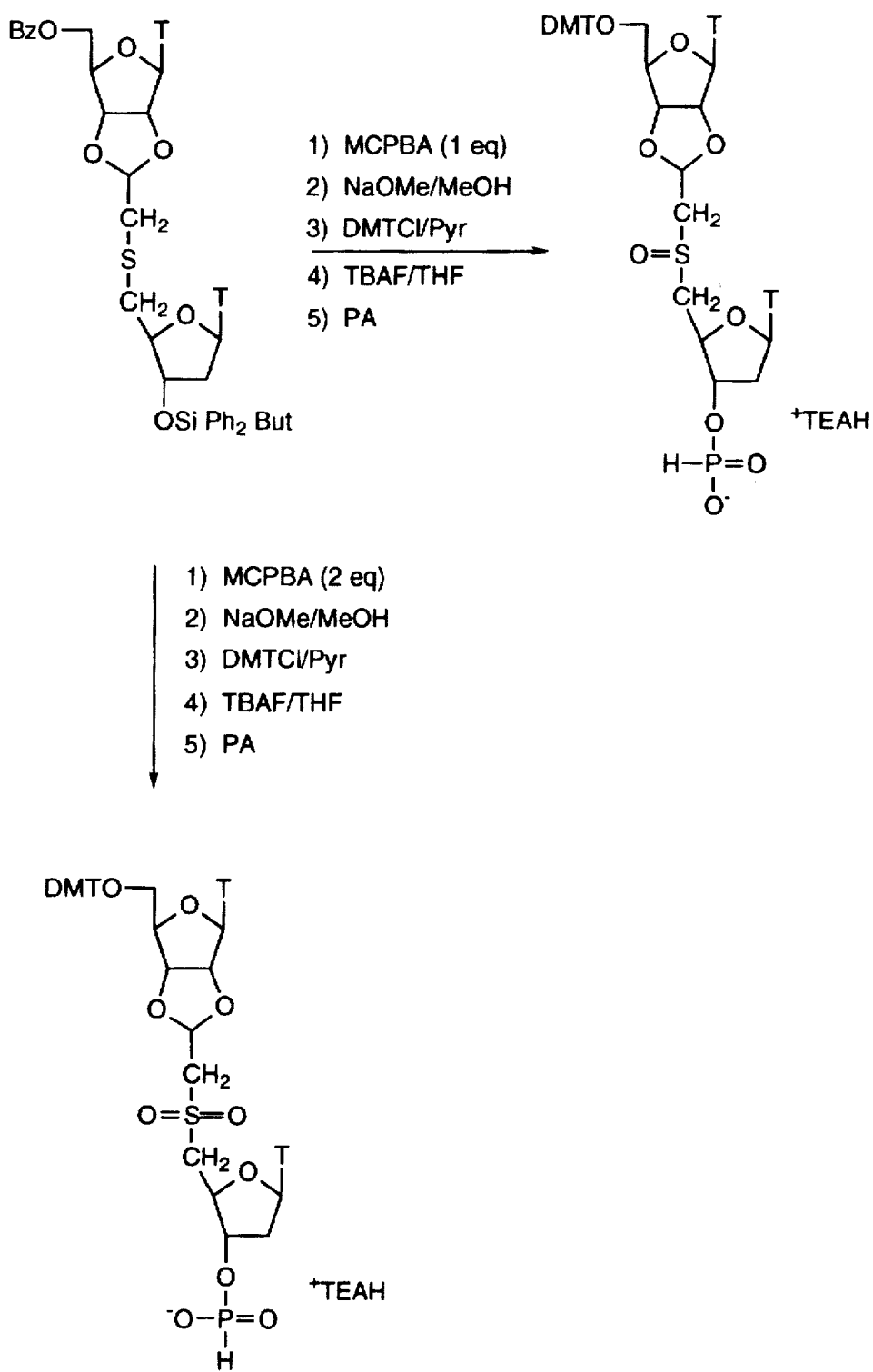
Figure 28:
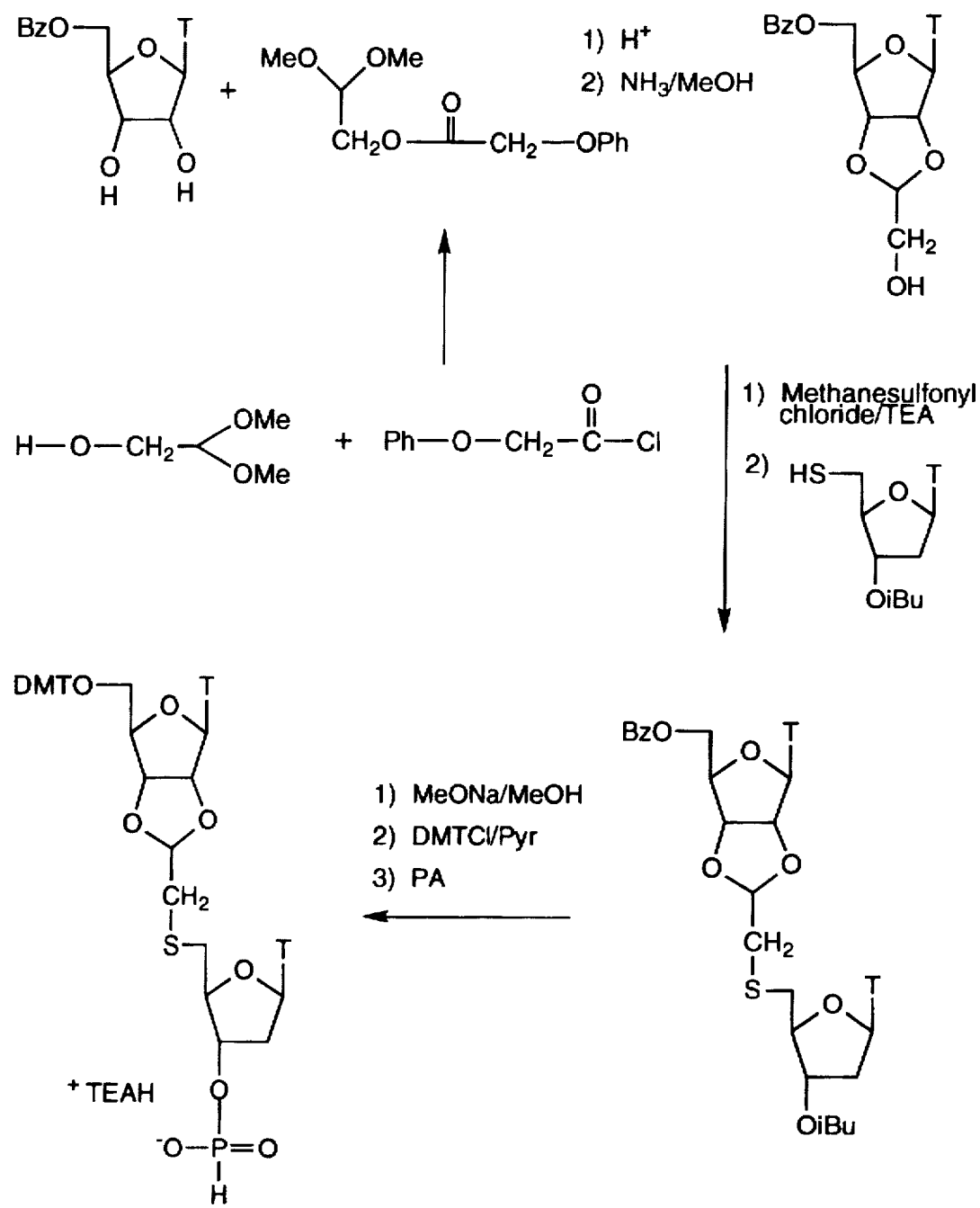
FIG. 28 shows synthesis of a five member ring with a 3 atom bridge.
Figure 29A:
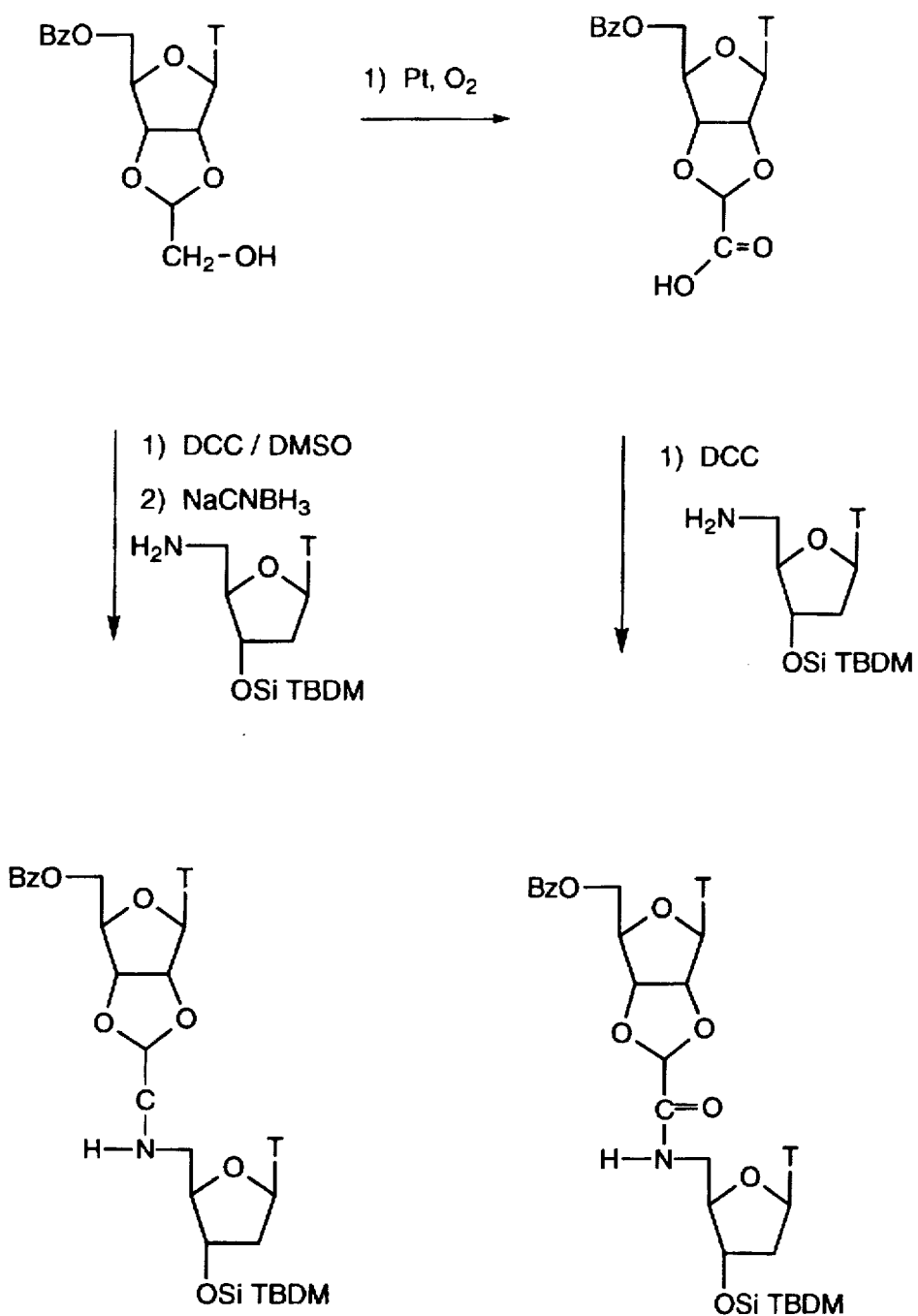
FIGS. 29-A to 29-B show synthesis of a five member ring with a 3 atom bridge.
Figure 29B:
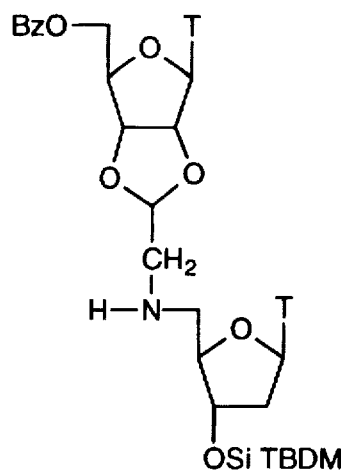
Figure 29B:
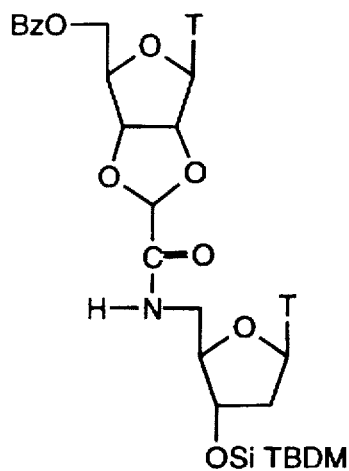
Figure 29B:
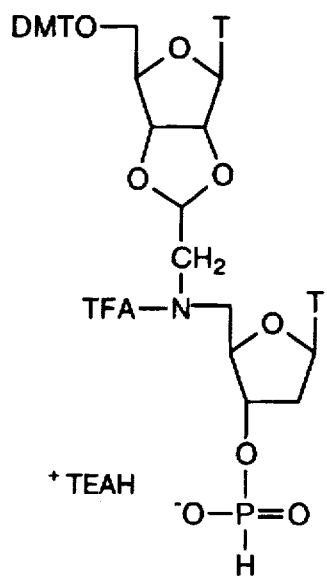
Figure 29B:
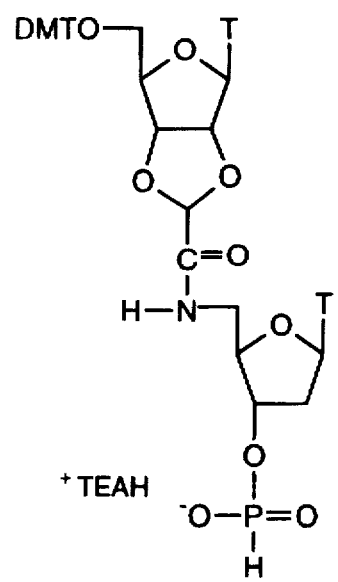
Figure 30:
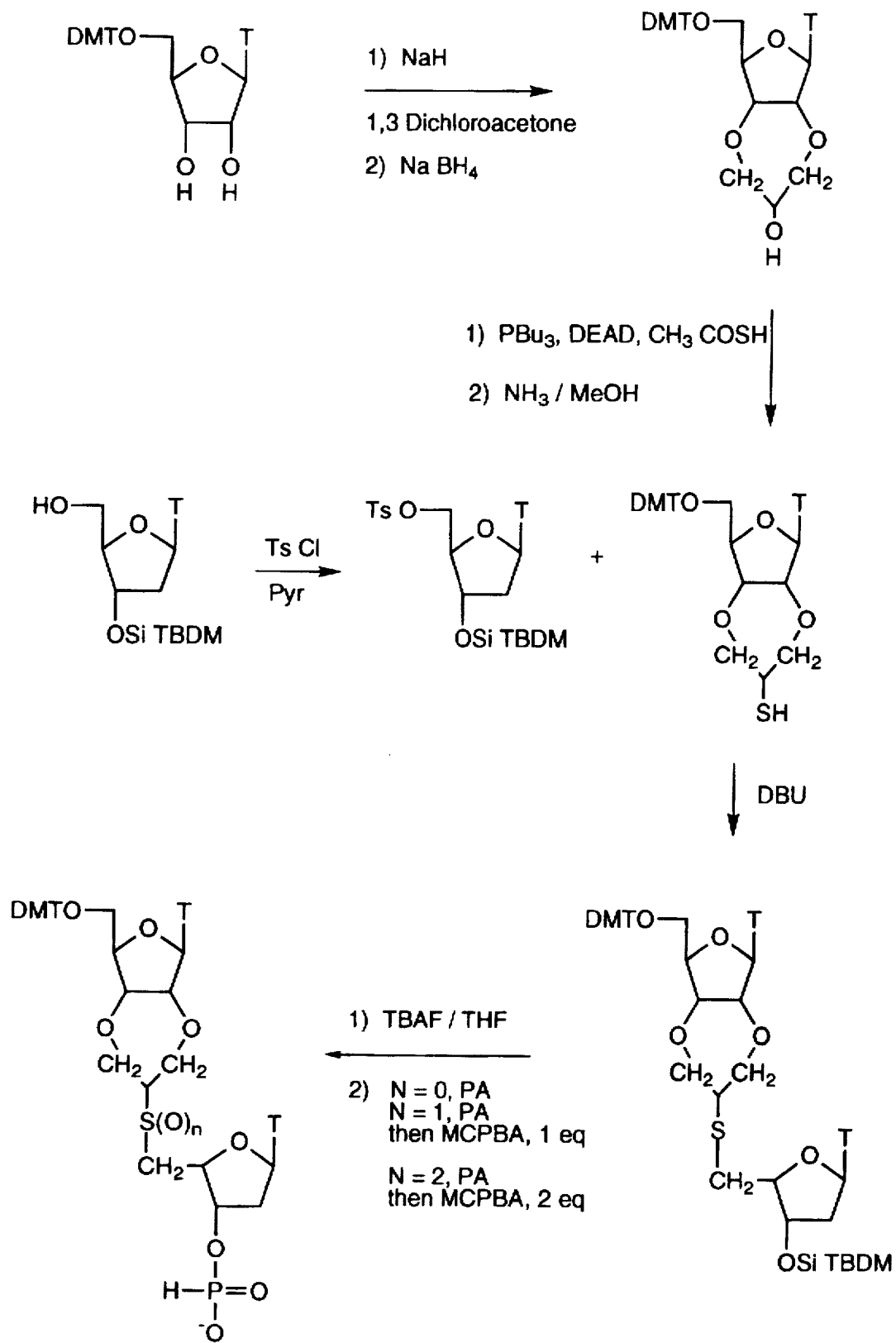
FIG. 30 shows synthesis of a seven member ring with a 2 atom bridge.
Figure 31:
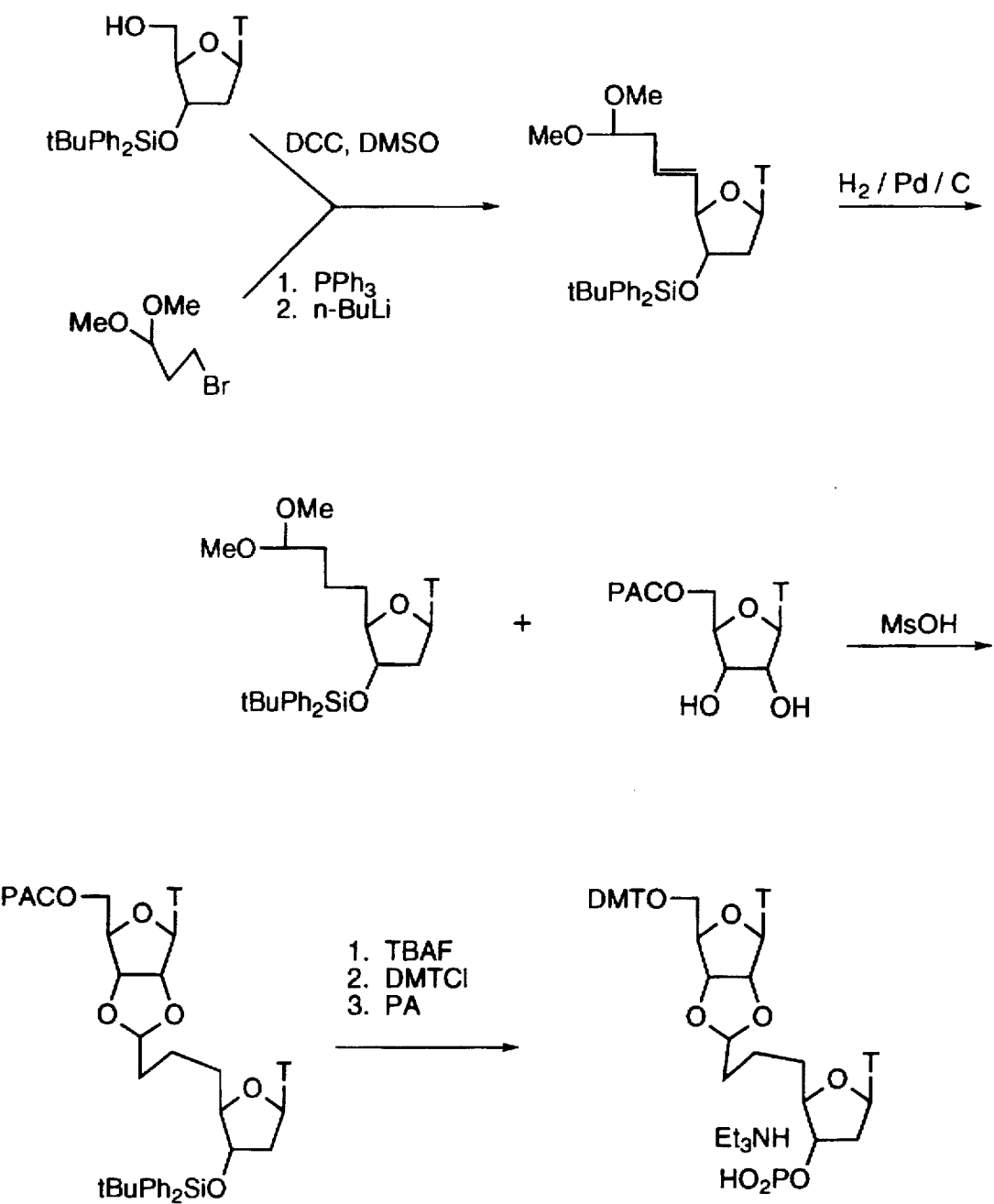
FIG. 31 shows synthesis of a five member ring with a 3 atom bridge.
Figure 32:
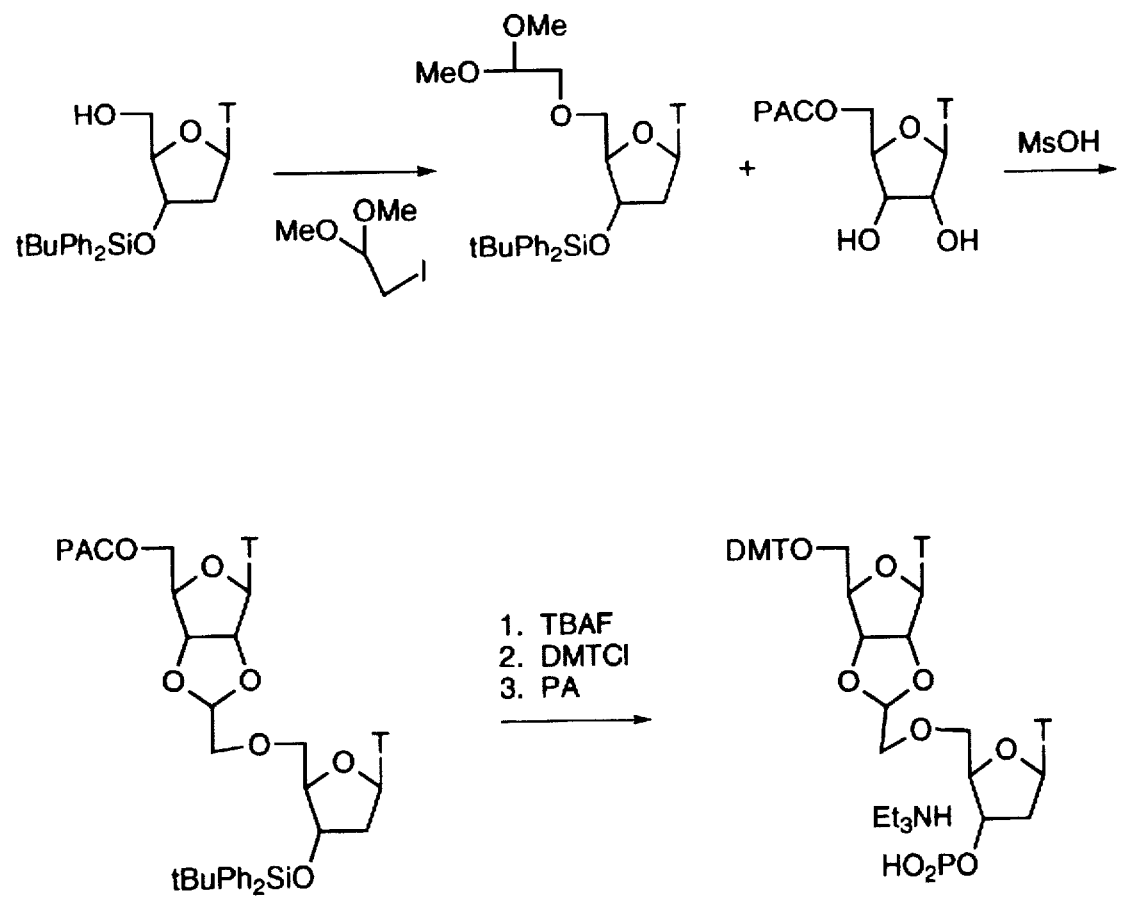
FIG. 32 shows synthesis of a five member ring with a 3 atom bridge.

A particularly preferred dimer synthon used to mediate the switchback in an oligomer is the O-xyloso linker (FIG. 26). The O-xyloso linker consists of two xylose-nucleomonomers linked to each other by O-xylene at the 3'-position of each xylose sugar. The switchback linker synthon was synthesized using α,α'-orthodibromoxylene and 5'-DMT nucleomonomer to give the dimer as shown in FIG. 26. The dimer was converted to the H-phosphonate and was used in solid phase synthesis to generate oligomers. Linkers containing the bases thymine, 5-methylcytosine, 5-(1-propynyl)uracil or cytosine were synthesized as homodimers. However, the switchback linker dimers can also be synthesized as mixed heterodimers that are separated chromatographically.

2' Modified Oligomers

Oligomers within the present invention include nucleomonomers having modifications of the ribose or deoxyribose sugar. 2'-O-methyl-, 2'-O-ethyl- and 2'-O-allyl oligomers have been synthesized and shown to bind to single-stranded complementary nucleic acid sequences (Cotten, M., et al., *Nucleic Acids Res* (1990) 19:2629–2635; Blencowe, B. J., et al., *Cell* (1989) 59:531–539; Sproat, B. S., et al., *Nucleic Acids Res* (1989) 17:3373–3386; Inoue, H., et al., *Nucleic Acids Res* (1987) 15:6131–6148; Morisawa, H., et al., European Patent Ser. No. 0339842; Chavis, C., et al., *J Organic Chem* (1982) 47:202–206; Sproat, B. S., et al, *Nucleic Acids Res* (1991) 19:733–738). The 2'-modified oligomers were reported to be relatively nuclease stable compared to unmodified controls. Synthesis of 2' fluoro nucleomonomers and their incorporation into oligomers has also been described (Codington, J. F., et al, *J Org Chem* (1964) 29:558–564; Fazakerley, G. V., et al, *FEBS Lett* (1985) 182:365–369). Synthesis of oligomer analogs containing the modified bases described herein would be based on methods described. Synthesis of oligomers containing 2'-amino nucleomonomers has been described (Pieken, W. A., et al, *Science* (1991) 253:314–317).

In an additional use of substitute linkages of the invention, 2'-O-allyl modified sugar forms of the nucleomonomers can be included in the oligomer. The 2'-O-allyl nucleomonomers can be prepared using standard methods.

The nucleomonomers derivatized at the 2'-position can be incorporated into oligomers in the same manner as underivatized forms.

Synthesis

Oligomers or the segments thereof are conventionally synthesized. The synthetic methods known in the art and described herein can be used to synthesize oligomers containing substitute linkages of the invention, as well as other linkages or substitute linkages known in the art, using appropriately protected nucleomonomers. Methods for the synthesis of oligomers having phosphorous containing linkages are found, for example, in Froehler, B., et al., *Nucleic Acids Res* (1986) 14:5399–5467; *Nucleic Acids Res* (1988) 16:4831– 4839; *Nucleosides and Nucleotides* (1987) 6:287–291; Froehler, B., *Tetrahedron Letters* (1986) 27:5575–5578; Caruthers, M. H. in *Oligodeoxynucleotides-Antisense Inhibitors of Gene Expression* (1989), J. S. Cohen, editor, CRC Press, Boca Raton, p7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al, International Publication Number WO 92/07864).

Oligomers containing nonphosphorous based substitute linkages that have been previously described in commonly owned pending applications nos. Ser. No. 07/874,334, PCT/US90/06110 and PCT/US91/06855 are preferably synthesized using suitably blocked dimer synthons as a starting material. Oligomers containing linkages of the present invention are also conveniently synthesized by preparation of dimer or trimer compounds by solution phase chemistry followed by conversion of the synthon to a derivative that is incorporated into oligomers by either solid or solution phase chemistry. Typical synthons are 5' DMT or MMT blocked 3' phosphonate or phosphoramidate derivatives which are prepared by standard methods (see: Gait, M. J. ed., *Oligonucleotide Synthesis; A Practical Approach* (1984) IRL Press, Oxford).

Oligomers having phosphorous-containing linkages or segments thereof are conventionally synthesized. Methods known in the art and described herein can be used to synthesize oligomers containing bases of the invention, as well as other bases known in the art, using appropriately protected nucleomonomers (see FIG. 12). Methods for the synthesis of oligomers are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in *Oligodeoxynucleotides-Antisense Inhibitors of Gene Expression* (1989), J. S. Cohen, editor, CRC Press, Boca Raton, p7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al, International Publication Number WO 92/07864).

Synthons that are included in the scope of the present invention include (i) dimers disclosed in general structural formulas I through XI and (ii) dimers, trimers and longer oligomers made by solid or solution phase synthesis. Trimers and longer synthons may contain more than one type of linkage. The synthons may include any purine, pyrimidine or analogs thereof as described above or 2', 3' and 5' groups such as OH, DMTO, MMTO, O-allyl, phosphate, a phosphonate or an amidite as described above.

Although the linkages of the invention are conveniently incorporated into oligomers using dimer or longer synthons, oligomer synthesis may be accomplished most efficiently using solid phase synthesis methods. Solid phase generation of the linkages of the invention is illustrated in FIG. 1.

Utility and Administration

As the oligomers of the invention are capable of significant single-stranded or double-stranded target nucleic acid binding activity to form duplexes, triplexes or other forms of stable association, these oligomers are useful in diagnosis of diseases that are associated with expression of one or more genes such as those associated with pathological conditions. Applications can employ the oligomers to specifically inhibit the expression of genes (or inhibit translation of RNA sequences encoded by those genes) that are associated with either the establishment or the maintenance of a pathological condition. Exemplary genes or RNAs encoded by those genes that can be targeted include those that encode enzymes, hormones, serum proteins, transmembrane proteins, adhesion molecules (LFA-1, GPII$_b$/III$_a$, ELAM-1, VACM-1, ICAM-1, E-selectin, and the like), receptor molecules including cytokine receptors, cytokines (IL-1, IL-2, IL-3, IL-4, IL-6 and the like), oncogenes, growth factors, and interleukins. Target genes or RNAs can be associated with any pathological condition such as those associated with inflammatory conditions, cardiovascular disorders, immune reactions, cancer, viral infections, bacterial infections and the like.

Oligomers of the present invention are suitable for use in both in vivo and ex vivo therapeutic applications. Target genes or RNAs encoded by those genes that can serve as targets include oncogenes, such as ras, k-ras, bcl-2, c-myb, bcr, c-myc, c-abl or overexpressed sequences such as mdm2, oncostatin M, IL-6 (Kaposi's sarcoma), HER-2 and translocations such as bcr/abl. Viral gene sequences or RNAs encoded by those genes such as polymerase or reverse transcriptase genes of herpesviruses such as CMV, HSV-1, HSV-2, retroviruses such as HTLV-1, HIV-1, HIV-2, or other DNA or RNA viruses such as HBV, HPV, VZV, influenza virus, rhinovirus and the like are also suitable targets. Other indications for oligomers of the invention include (1) modulation of inflammatory responses by modulating expression of genes such as IL-1 receptor, IL-1, ICAM-1 or E-Selectin that play a role in mediating inflammation and (2) modulation of cellular proliferation in conditions such as arterial occlusion (restenosis) after angioplasty by modulating the expression of (a) growth or mitogenic factors such as non-muscle myosin, myc, fos, PCNA, PDGF or FGF or their receptors, or (b) cell proliferation factors such as c-myb. Other suitable proliferation factors or signal transduction factors such as TGFα, IL-6, γINF, protein kinase C, tyrosine kinases (such as p210, p190), may be targeted. In addition, EGF receptor, TGFα or MHC alleles may be targeted.

Delivery of oligomers of the invention into cells can be enhanced by any suitable method including calcium phosphate, DMSO, glycerol or dextran transfection, electroporation or by the use of cationic anionic and/or neutral lipid compositions or liposomes by methods described (International Publication Nos. WO 90/14074, WO 91/16024, WO 91/17424, U.S. Pat. No. 4,897,355). The oligomers can be introduced into cells by complexation with cationic lipids such as DOTMA (which may or may not form liposomes) which complex is then contacted with the cells. Suitable cationic lipids include but are not limited to N-(2, 3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 1,2-bis(oleyloxy)-3-(trimethylammonio) propane and its salts.

Enhanced delivery of the invention oligomers can also be mediated by the use of (i) viruses such as Sendai virus (Bartzatt, R., *Biotechnol Appl Biochem* (1989) 11:133–135) or adenovirus (Wagner, E., et al, *Proc Natl Acad Sci* (1992) 89:6099–6013; (ii) polyamine or polycation conjugates using compounds such as polylysine, protamine or N1, N12-bis(ethyl)spermine (Wagner, E., et al, *Proc Natl Acad Sci* (1991) 88:4255–4259; Zenke, M., et al, *Proc Natl Acad Sci* (1990) 87:3655–3659; Chank, B. K., et al, *Biochem Biophys Res Commun* (1988) 157:264–270; U.S. Pat. No. 5,138,045); (iii) lipopolyamine complexes using compounds such as lipospermine (Behr, J.-P., et al, *Proc Natl Acad Sci* (1989) 86:6982–6986; Loeffler, J. P., et al *J Neurochem* (1990) 54:1812–1815); (iv) anionic, neutral or pH sensitive lipids using compounds including anionic phospholipids such as phosphatidyl glycerol, cardiolipin, phosphatidic acid or phosphatidylethanolamine (Lee, K.-D., et al, *Biochim Biophys ACTA* (1992) 1103:185–197; Cheddar, G., et al, *Arch Biochem Biophys* (1992) 294:188–192; Yoshimura, T., et al, *Biochem Int* (1990) 20:697–706); (v) conjugates with compounds such as transferrin or biotin or (vi) conjugates with compounds such as serum proteins (including albumin or antibodies), glycoproteins or polymers (including polyethylene glycol). As used herein, transfection refers to any method that is suitable for delivery of oligomers into cells. Any reagent such as a lipid or any agent such as a virus that can be used in transfection protocols is collectively referred to herein as a "permeation enhancing agent". Delivery of the oligomers into cells can be via cotransfection with other nucleic acids such as (i) expressable DNA fragments encoding a protein(s) or a protein fragment or (ii) translatable RNAs that encode a protein(s) or a protein fragment.

The oligomers can thus be incorporated into any suitable formulation that enhances delivery of the oligomers into cells. Suitable pharmaceutical formulations also include those commonly used in applications where compounds are delivered into cells or tissues. Compounds such as polyethylene glycol, propylene glycol, azone, nonoxonyl-9, oleic acid, DMSO, polyamines or lipopolyamines can be used in topical preparations that contain the oligomers.

The invention oligomers can be conveniently used as reagents for research or production purposes where inhibition of gene expression is desired. There are currently very few reagents available that efficiently and specifically inhibit the expression of a target gene by any mechanism. Oligomers that have been previously reported to inhibit target gene expression frequently have nonspecific effects and/or do not reduce target gene expression to very low levels (less than about 40% of uninhibited levels).

Thus, the oligomers as described herein constitute a reagent that can be used in methods of inhibiting expression of a selected protein or proteins in a subject or in cells wherein the proteins are encoded by DNA sequences and the proteins are translated from RNA sequences, comprising the steps of: introducing an oligomer of the invention into the cells; and permitting the oligomer to form a triplex with the DNA or RNA or a duplex with the DNA or RNA whereby expression of the protein or proteins is inhibited. The methods and oligomers of the present invention are suitable for modulating gene expression in both procaryotic and eucaryotic cells such as bacterial, fungal parasite, yeast and mammalian cells.

RNase H "competent" or RNase H "incompetent" oligomers can be easily designed using the substitute linkages of the invention. RNase H competent oligomers can comprise one or more RNase H competent domains comprised of linked RNase H competent nucleomonomers. Oligomers having modifications such as 2'-substitutions (2'-O-allyl and the like) or certain uncharged linkages (methylphosphonate, phosphoramidate and the like) are usually incompetent as a substrate that is recognized by and/or acted on by RNase H. RNase H competence can facilitate antisense oligomer function by degrading the target RNA in an RNA-oligomer duplex (Dagle, J. M., et al, *Nucl Acids Res* (1990) 18:4751–4757; Walder, J. A. et al, International Publication Number WO 89/05358). The enzyme cleaves RNA in RNA-DNA duplexes.

In order to retain RNase H competence, an oligomer requires a RNase H competent domain of three or more competent contiguous nucleomonomers located within it (Quartin, R. S., et al, *Nucl Acids Res* (1989) 17:7253–7262). Design of oligomers resistant to nuclease digestion will have terminal linkage, sugar and/or base modifications to effect nuclease resistance. Thus, the oligomers can be designed to have modified nucleomonomer residues at either or both the 5'- and/or 3'-ends, while having an internal RNase H competent domain.

Exemplary oligomers that retain RNase H competence would generally have uniform polarity and would comprise about 2 to about 12 nucleomonomers at the 5'-end and at the 3'-end which stabilize the oligomer to nuclease degradation and about three to about 26 nucleomonomers that function as a RNase H competent domain between the RNase H incompetent 3'- and 5'-ends. Variations on such an oligomer would include (1) a shorter RNase H competent domain comprising 1 or 2 RNase H competent linkages or substitute linkages, (2) a longer RNase H incompetent domain comprising up to 15, 20 or more substitute linkages or nucleomonomers, (3) a longer RNase H competent domain comprising up to 30, 40 or more linkages, (4) oligomers with only a single RNase H incompetent domain at the 3' end or at the 5' end, or (5) oligomers having more than one RNase H competent domain. RNase H competence also applies as a consideration to oligomers having one or more regions of inverted polarity, to circular oligomers and to other types of oligomers.

Oligomers containing as few as about 8 nucleomonomers can be used to effect inhibition of target protein(s) expression by formation of duplex or triplex structures with target nucleic acid sequences. However, linear oligomers used to inhibit target protein expression via duplex or triplex formation will preferably have from about 10 to about 20 nucleomonomer residues.

Oligomers containing substitute linkages of the invention can be conveniently circularized as described (International Publication No. WO 92/19732; Kool, E. T. *J Am Chem Soc* (1991) 113:6265–6266; Prakash, G., et al. *J Am Chem Soc* (1992) 114:3523–3527). Such oligomers are suitable for binding to single-stranded or double-stranded nucleic acid targets. Circular oligomers can be of various sizes. Such oligomers in a size range of about 22–50 nucleomonomers can be conveniently prepared. The circular oligomers can have from about three to about six nucleomonomer residues in the loop region that separate binding domains of the oligomer as described (Prakash, G. ibid). Oligomers can be enzymatically circularized through a terminal phosphate by ligase or by chemical means via linkage through the 5'- and 3'-terminal sugars and/or bases.

The oligomers can be utilized to modulate target gene expression by inhibiting the interaction of nucleic acid binding proteins responsible for modulating transcription (Maher, L. J., et al. *Science* (1989) 245:725–730) or translation. The oligomers are thus suitable as sequence-specific agents that compete with nucleic acid binding proteins (including ribosomes, RNA polymerases, DNA polymerases, translational initiation factors, transcription factors that either increase or decrease transcription, protein-hormone transcription factors and the like). Appropriately designed oligomers can thus be used to increase target protein synthesis through mechanisms such as binding to or near a regulatory site that transcription factors use to repress expression or by inhibiting the expression of a selected repressor protein itself.

The invention oligomers, comprising additional modifications that enhance binding affinity can be designed to contain secondary or tertiary structures, such as pseudoknots or pseudo-half-knots (Ecker, D. J., et al. *Science* (1992) 257:958–961). Such structures can have a more stable secondary or tertiary structure than corresponding unmodified oligomers. The enhanced stability of such structures would rely on the increased binding affinity between regions of self complementarity in a single oligomer or regions of complementarity between two or more oligomers that form a given structure. Such structures can be used to mimic structures such as the HIV TAR structure in order to interfere with binding by the HIV Tat protein (a protein that binds to TAR). A similar approach can be utilized with other transcription or translation factors that recognize higher nucleic acid structures such as stems, loops, hairpins, knots and the like. Alternatively, the invention oligomers can be used to (1) disrupt or (2) bind to such structures as a method to (1) interfere with or (2) enhance the binding of proteins to nucleic acid structures.

The oligomers of the invention can also be applied as or diagnostic agents that function by direct displacement of one strand in a duplex nucleic acid. Displacement of a strand in a natural duplex such as chromosomal DNA or duplex viral DNA, RNA or hybrid DNA/RNA is possible for oligomers with a high binding affinity for their complementary target sequences. Types of target nucleic acids include but are not limited to (i) gene sequences including exons, introns, exon/intron junctions, promoter/enhancer regions and 5' or 3' untranslated regions, (ii) regions of nucleic acids that utilize secondary structure in order to function (e.g. the HIV TAR stem-loop element or tRNAs), (iii) nucleic acids that serve structural or other functions such as telomeres, centromeres or replication origins (virus, bacteria and the like) and (iv) any other duplex region. It is clear that oligomers can be synthesized with discrete functional domains wherein one region of an oligomer binds to a target by D-looping while an adjacent region binds a target molecule by say, forming a triple helix or binding as an aptamer to a protein. Alternatively, a D-looping oligomer can bind to each strand in a duplex by switching the strand to which the oligomer binds (i.e. by having one region of the oligomer that binds to one strand and another region that binds to the complementary strand). The controlling elements that dictate the mode of binding (i.e. triple helix or D-loop) are the sequence of the oligomer and the inherent affinity built into the oligomer. Base recognition rules in Watson-Crick duplex binding differ from those in Hoogsteen controlled triplex binding. Because of this, the oligomer base sequence can be used to dictate the type of binding rules an oligomer will utilize.

D-loop structures are formed in nature by enzyme-mediated processes (Harris, L. D. et al., *J Biol Chem* (1987) 262:9285–9292) or are associated with regions where DNA replication occurs (Jacobs, H. T. et al., *Nucl Acids Res* (1989) 17:8949–8966). D-loops that arise from the binding of oligomers can result from a one or two step process. Direct displacement of a target strand will give rise to a D-loop by a single binding event. However, D-looping can also occur by forming a triple helix which facilitates a strand displacement event leading to the D-loop.

Ribozymes containing substitute linkages of the invention can be designed in order to design species with altered characteristics. Ribozymes that cleave single stranded RNA or DNA (Robertson, D. L., et al *Nature* (1990) 344:467–468) have been described. Therapeutic applications for ribozymes have been postulated (Sarver, N. et al, *Science* (1990) 247:1222–1225; International Publication Number WO 91/04319). Secondary or tertiary structure necessary for ribozyme function can be affected by design of appropriate oligomer sequences. For example, ribozymes having nuclease stable targeting domains containing substitute linkages of the invention can have higher affinity, while maintaining base pairing specificity, for target sequences.

Because of the higher affinity and/or nuclease stability of the invention substitute linkages shorter recognition domains in a ribozyme (an advantage in manufacturing) can be designed which can lead to more favorable substrate turnover (an advantage in ribozyme function).

The oligomers of the invention can be used as diagnostic reagents to detect the presence or absence of the target nucleic acid sequences to which they specifically bind. The enhanced binding affinity of the invention oligomers is an advantage for their use as primers and probes. Diagnostic tests cab be conducted by hybridization through either double or triple helix formation which is then detected by conventional means. For example, the oligomers can be labeled using radioactive, fluorescent, or chromogenic labels and the presence of label bound to solid support detected. Alternatively, the presence of a double or triple helix can be detected by antibodies which specifically recognize these forms. Means for conducting assays using such oligomers as probes are generally known.

The use of oligomers containing the invention substitute linkages as diagnostic agents by triple helix formation is advantageous since triple helices form under mild conditions and the assays can thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming, as RNA is extremely sensitive to ubiquitous nucleases.

The oligomer probes can also incorporate additional modifications such as modified sugars and/or substitute linkages that render the oligomer especially nuclease stable, and would thus be useful for assays conducted in the presence of cell or tissue extracts which normally contain nuclease activity. Oligomers containing terminal modifications often retain their capacity to bind to complementary sequences without loss of specificity (Uhlmann et al., *Chemical Reviews* (1990) 90:543–584). As set forth above, the invention probes can also contain linkers that permit specific binding to alternate DNA strands by incorporating a linker that permits such binding (Froehler, B. C., et al, *Biochemistry* (1992) 31:1603–1609); Horne et al., *J Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

Oligomers of the invention are suitable for use in diagnostic assays that employ methods wherein either the oligomer or nucleic acid to be detected are covalently attached to a solid support as described (U.S. Pat. No. 4,775,619). The oligomers are also suitable for use in diagnostic assays that rely on polymerase chain reaction techniques to amplify target sequences according to described methods (European Patent Publication No. 0 393 744). Oligomers of the invention containing a 3' terminus that can serve as a primer are compatible with polymerases used in polymerase chain reaction methods such as the Taq or Vent™ (New England Biolabs) polymerase. Oligomers of the invention can thus be utilized as primers in PCR protocols.

The oligomers are useful as primers that are discrete sequences or as primers with a random sequence. Random sequence primers can be generally about 6, 7, or 8 nucleomonomers in length. Such primers can be used in various nucleic acid amplification protocols (PCR, ligase chain reaction, etc) or in cloning protocols. The substitute linkages of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized to chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinking agents such as 5-(3-iodoacetamidoprop-1-yl)-2'-deoxyuridine or 5-(3-(4-bromobutyramido)prop-1-yl)-2'-deoxyuridine and used in various assay methods or kits as described (International Publication No. WO 90/14353).

In addition to the foregoing uses, the ability of the oligomers to inhibit gene expression can be verified in in vitro systems by measuring the levels of expression in subject cells or in recombinant systems, by any suitable method (Graessmann, M., et al., *Nucleic Acids Res* (1991) 19:53–59).

All references cited herein are incorporated herein by reference in their entirety.

The following examples are intended to illustrate, but not to limit, the invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLE 1

Synthesis of 5' DMT-T-Riboacetal-T-3'-H-Phosphonate Dimer Synthon

A TT riboacetal dimer was synthesized as shown in FIG. 1. The starting material 7'-carboxyl-3't-butyl dimethyl silyl thymidine was obtained as described in pending application Ser. No. 763,130 and converted to the aldehyde as shown. The TT dimer was purified by silica gel chromatography and used in solid phase oligomer synthesis using H-phosphonate chemistry.

EXAMPLE 2

Synthesis of Oligomers Containing Riboacetal Linkages and Their binding to Duplex DNA The dimer of Example 1 was incorporated into oligomer ODN-2 with the following sequence. ODN-1 was the control oligomer with diester linkages.

Base residues designated C corresponded to 5-methylcytosine, T corresponded to thymine and * indicates the location of the riboacetal linkage. The oligomers were hybridized with duplex DNA containing the target sequence 5' AGAGAGAGAGAAAAA 3'. Hybridization was carried out in 140 mM KCl, 5 mM MgCl$_2$, 5 mM Na$_2$HPO$_4$, pH 6.6. The oligomer bound to the target sequence in a parallel triplex binding motif as described in pending application number 643,382. Thermal stability ($T_m$) of the resulting triplex helix formed between each oligomer and the target sequence was determined. All DNAs and oligomers were present at approximately 1 μM. The $T_m$ of ODN-1 was 44.0° C. and 51.4° C. for ODN-2. The $T_m$ value associated with oligomers containing riboacetal linkages was greater than that of the control oligomers.

Additionally, the dimers T*T and T*C bearing the riboacetal substitute linkage were incorporated in ODN 3 having seven riboacetal linkages and the following sequence ODN 3 5' T*CT*CT*CT*CT*CTT*TT*TT 3'. The affinity of ODN 3 for duplex DNA was determined by a footprint assay as described (Matteucci, M. et al *J Am Chem Soc* (1991), 113:7767–7768). The control ODN 1 gave complete binding at 1 μM while ODN 3 gave complete protection at 0.01 μM, demonstrating approximately 100-fold enhancement of affinity relative to the diester control. ODN 3 was also analyzed by thermal melting using the buffer as described above except with 1 mM MgCl$_2$ at pH 6.6 and at pH 7.0. At pH 6.6, ODN 3 had a triple helix transition at 67° C. while control ODN 1 had a transition at 40° C. At pH 7.0, ODN 3 had a transition at 60° C. and ODN 1 had a transition at 34° C. These results again demonstrated the higher binding affinity of oligomers containing riboacetal linkages relative to control oligomers.

EXAMPLE 3

Binding of Oligomer Containing Riboacetal Linkages to Single-Stranded DNA and RNA ODN-1 and ODN-2 were hybridized with the complementary single-stranded sequence through antiparallel Watson-Crick binding to the following oligonucleotide target DNA sequence 5' AAAAAGAGAGAGAGA 3' or RNA sequence 5' AAAAAGAGAGAGAGA 3'. The $T_m$ of the control oligomer ODN-1 was 49.0° C. on DNA while the $T_m$ of ODN-2 was 49.5° C. on DNA. Control oligomer ODN-1 on RNA was 63.5° C. and ODN-2 was 61.5° C. Buffer conditions for both experiments were 140 mM KCl, 5 mM Na$_2$HPO$_4$, 1 mM MgCl$_2$ pH 6.6, and DNA or RNA were present at approximately 1 μM concentration.

EXAMPLE 4

Solid Phase Incorporation of Riboacetal Linkages into Oligomers

Solid phase incorporation of riboacetal linkages into oligomers is shown in FIG. 2. Elongation of the oligomer chain in a 5' to 3' direction is used to obtain a fully or partially substituted oligomer. As shown in the figure, synthesis is initiated by coupling of suitably blocked monomer to a suitable support through the 5' position by reaction between support and protected-ribothymidine. The ester linkage shown may be varied as described. The blocking group (BL) indicated in FIG. 2 may be phenoxyacetyl ester which is deblocked by mild ammonia treatment or the blocking group may be FMOC carbonates which are removed by piperidine treatment as described (Green, T. W. et al *Protective Groups in Organic Synthesis* (1991) second edition, Wiley & Sons, New York). Chain elongation would proceed by repeating the reaction sequence.

EXAMPLE 5

Synthesis of 5' DMT-T-Oxoacetal-T-3'-H-Phosphonate Dimer Synthon

Figure 3:
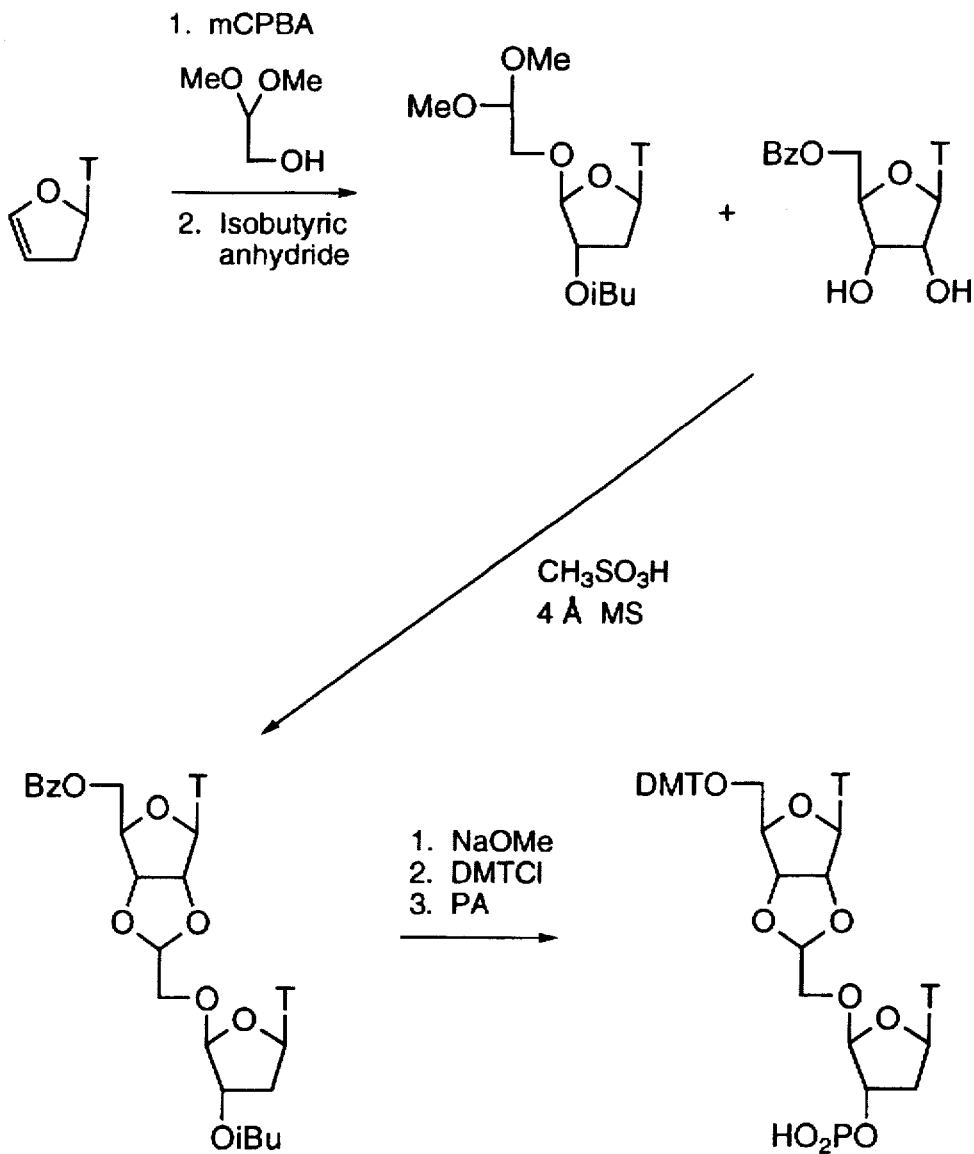
FIG. 3 describes the synthesis of a 5'-DMT oxoriboacetal synthon of Example 5.

A TT oxoacetal dimer was synthesized as shown in FIG. 3. The starting material thymidine enol ether was obtained as described (Zemlica, J. et al., *J Am Chem Soc* (1972) 94:3213–3218). This was treated with the alcohol and MCPBA essentially as described (Kim, C. U. et al., *J Med Chem* (1991) 34:2286–2294).

EXAMPLE 6

Synthesis of 5' DMT-T-Thioriboacetal-T-3'-H-Phosphonate Dimer Synthon

Synthesis of a TT thioriboacetal dimer is shown in FIG. 4. The starting material thymidine enol ether is obtained as described by Zemlica, et al. above and converted as shown.

EXAMPLE 7

Synthesis of 5' DMT-T-Dioxa Azepine-T-3'-H-Phosphonate Dimer

Figure 5:
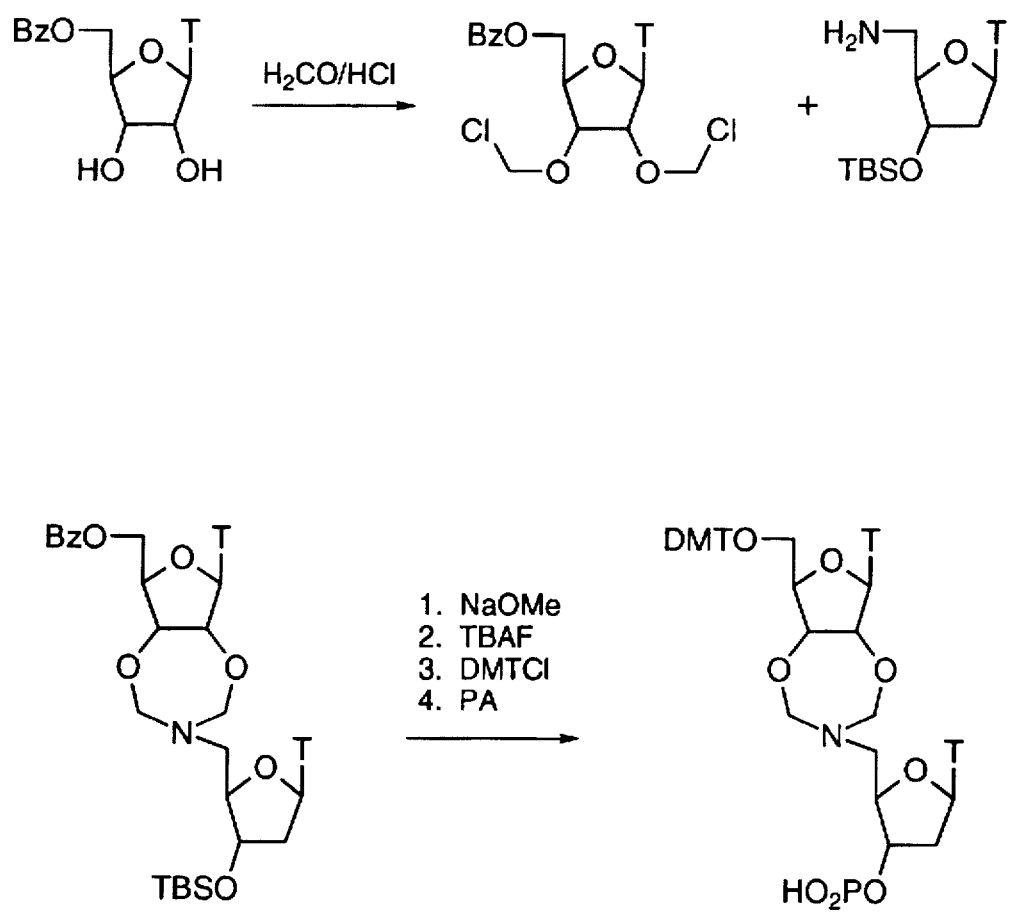
FIG. 5 describes the synthesis of a DMT synthon of a seven member ring system in Example 7.

Synthesis of a TT dioxa azepine dimer containing the 7-member ring structure is shown in FIG. 5. The starting material is obtained from ribothymidine and converted as shown. The 5' amino-T compound was obtained as described in application Ser. No. 763,130.

EXAMPLE 8

Synthesis of 5' DMT-T-Carbamate Aminal-T-3'-H-Phosphonate Dimer

Figure 6:
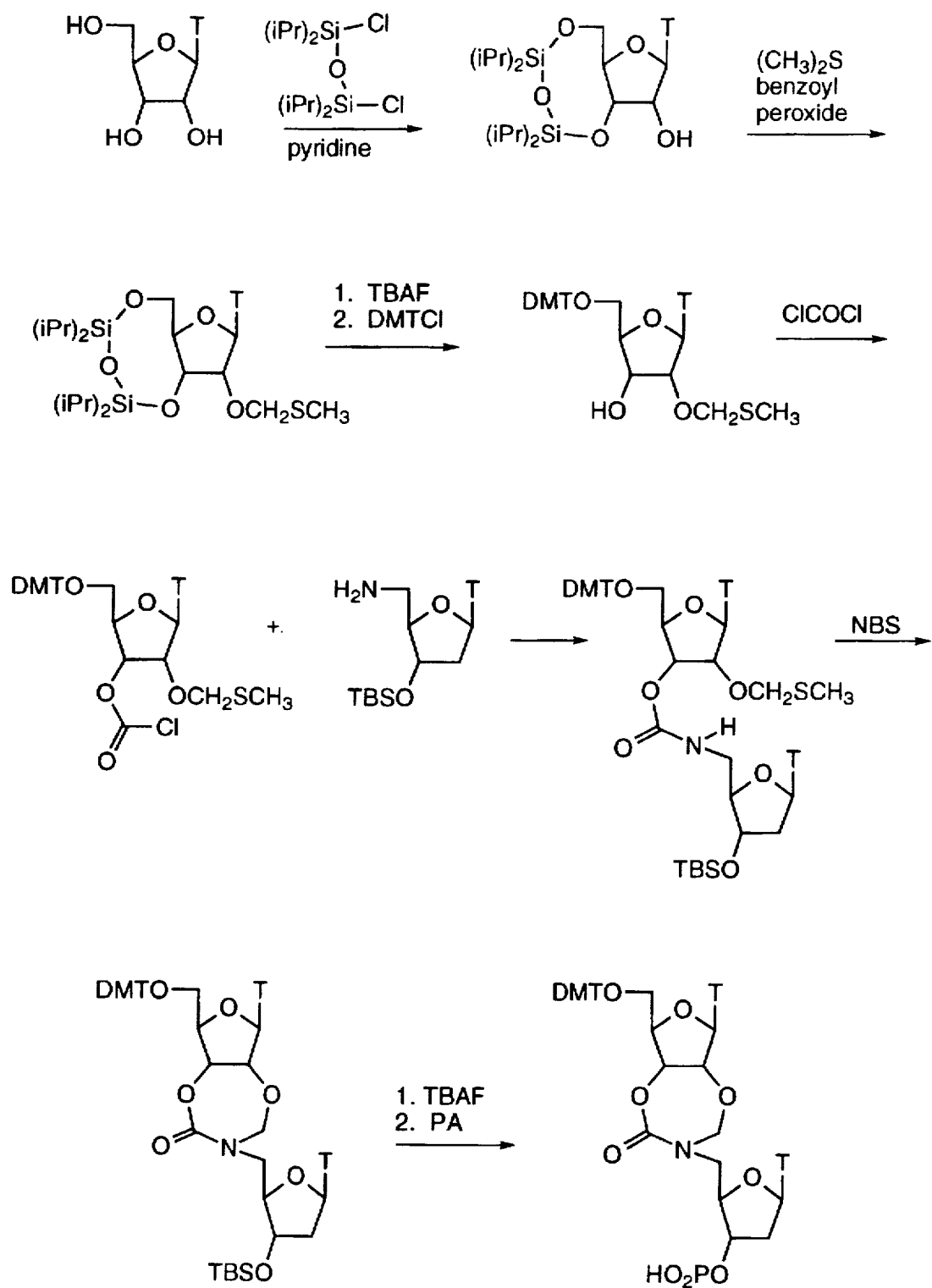
FIG. 6 describes the synthesis of a DMT synthon of a seven member ring system of Example 8.

Synthesis of a TT carbamate aminal dimer containing the 7-member ring structure is shown in FIG. 6. The first step of the reaction has been previously described (Markiewicy, W. T. et al *Nucl Acids Res, Spec Publ* (1978) 4:S185). The starting material is obtained from ribothymidine and converted as shown.

EXAMPLE 9

Synthesis of 5' DMT-T-MethylRiboacetal-T-3'-H-Phosphonate Dimer

Figure 7:
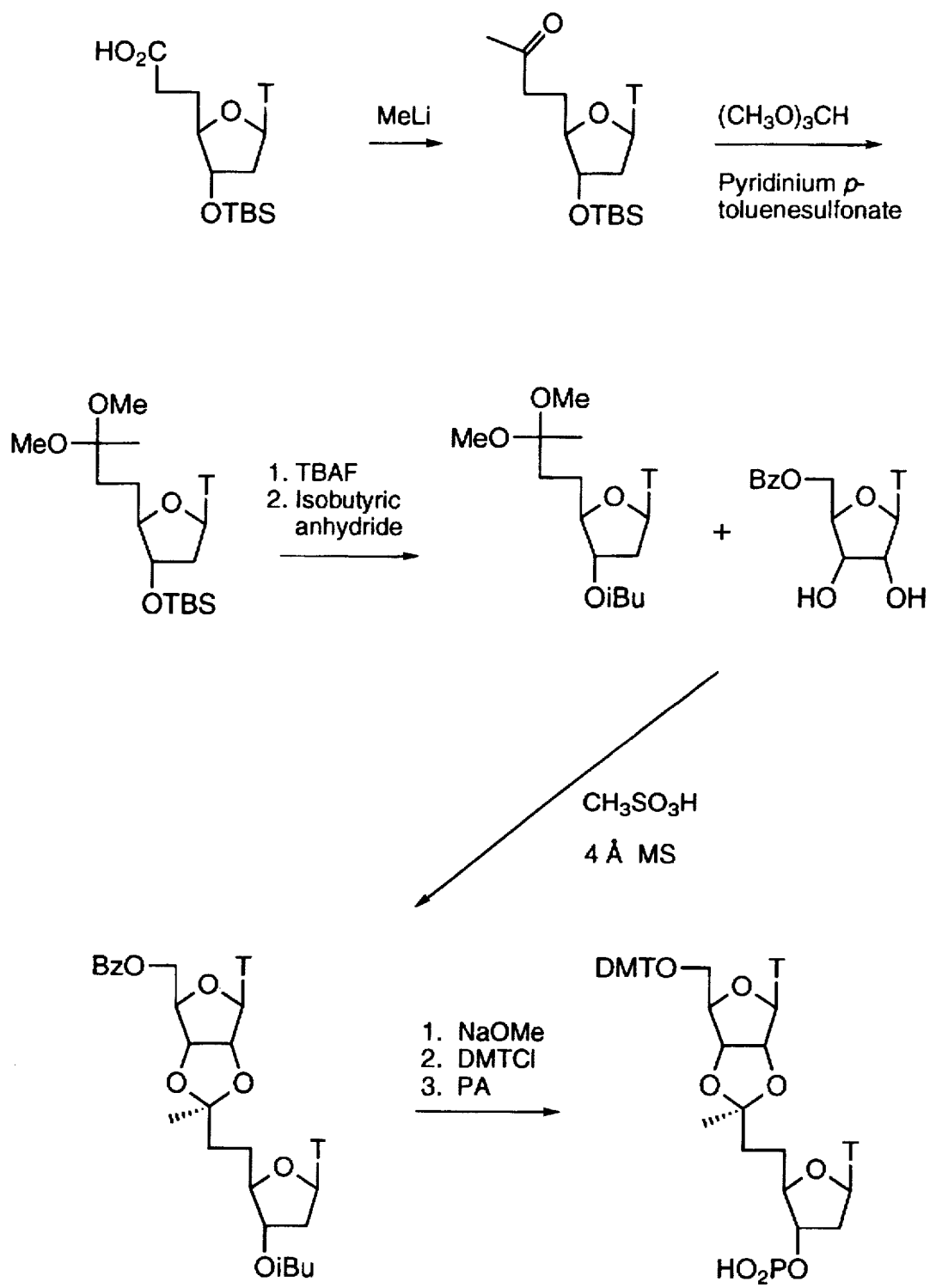
FIG. 7 describes the synthesis of a DMT synthon of the riboacetal of Example 9.

Synthesis of a TT methylriboacetal dimer containing the 5-member ring structure is shown in FIG. 7. The starting material is obtained as described in application Ser. No. 763,130 and converted as shown.

EXAMPLE 10

Synthesis of 5' DMT-T-Oxa Amine-T-3'-H-Phosphonate Dimer

Figure 8:
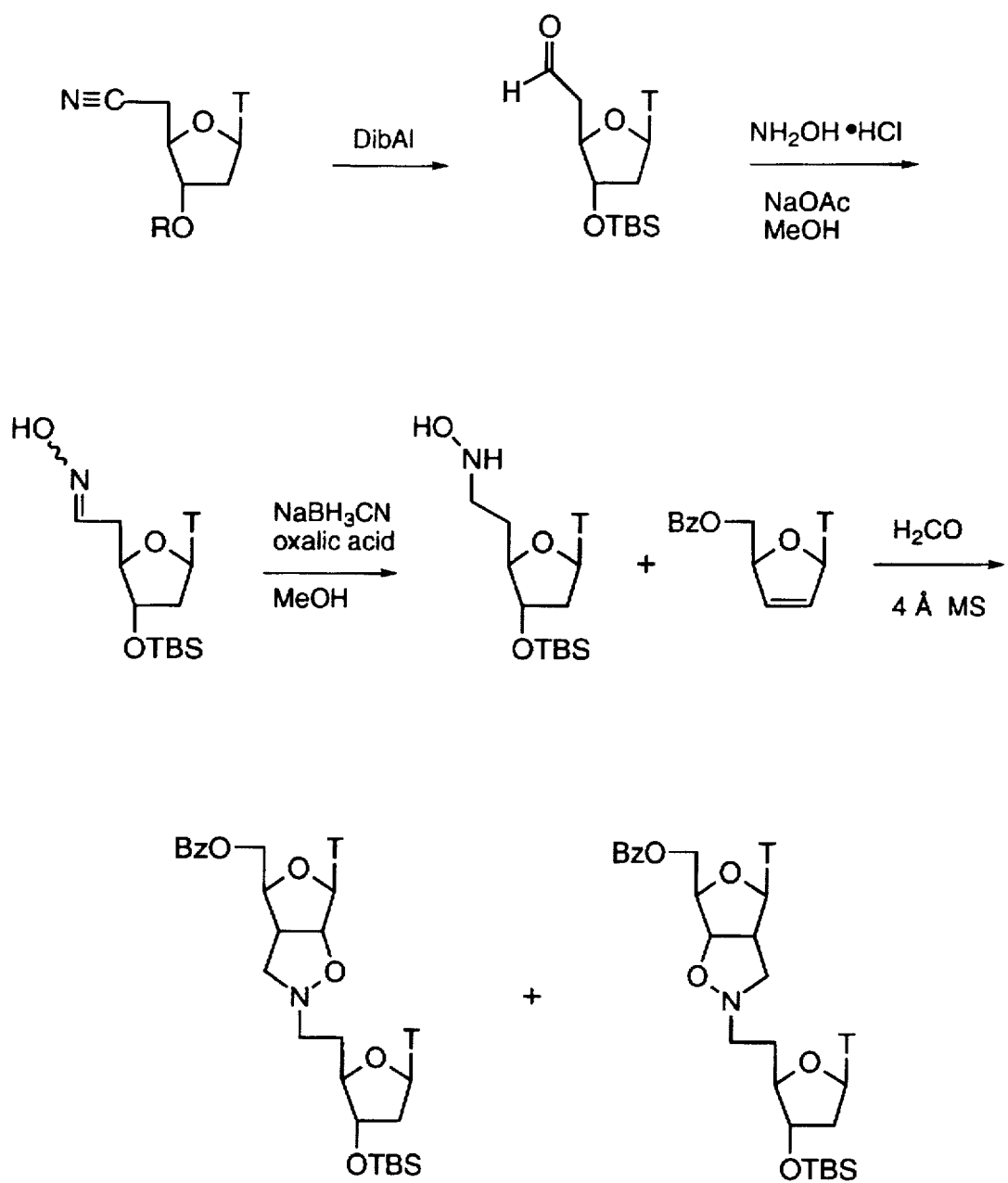
FIG. 8 describes the synthesis of a benzoyl synthon a riboacetal of Example 10.

Synthesis of a TT oxa amine dimer containing the 5-member ring structure is shown in FIG. 8. The starting material is obtained as described in application Ser. No. 763,130 and converted as shown. A mixture of 2 aminal linkage types is obtained. The isomers may be separated by chromatography. The TBS blocked compound is converted to the 5' DMT 3' H-phosphonate by reaction with (i) NaOMe, (ii) DMT/pyridine, (iii) TBAF and (iv) phosphytylation.

EXAMPLE 11

Synthesis of 5' DMT-T-Cyclic Carbamate-T-3'-H-Phosphonate Dimer

Figure 9:
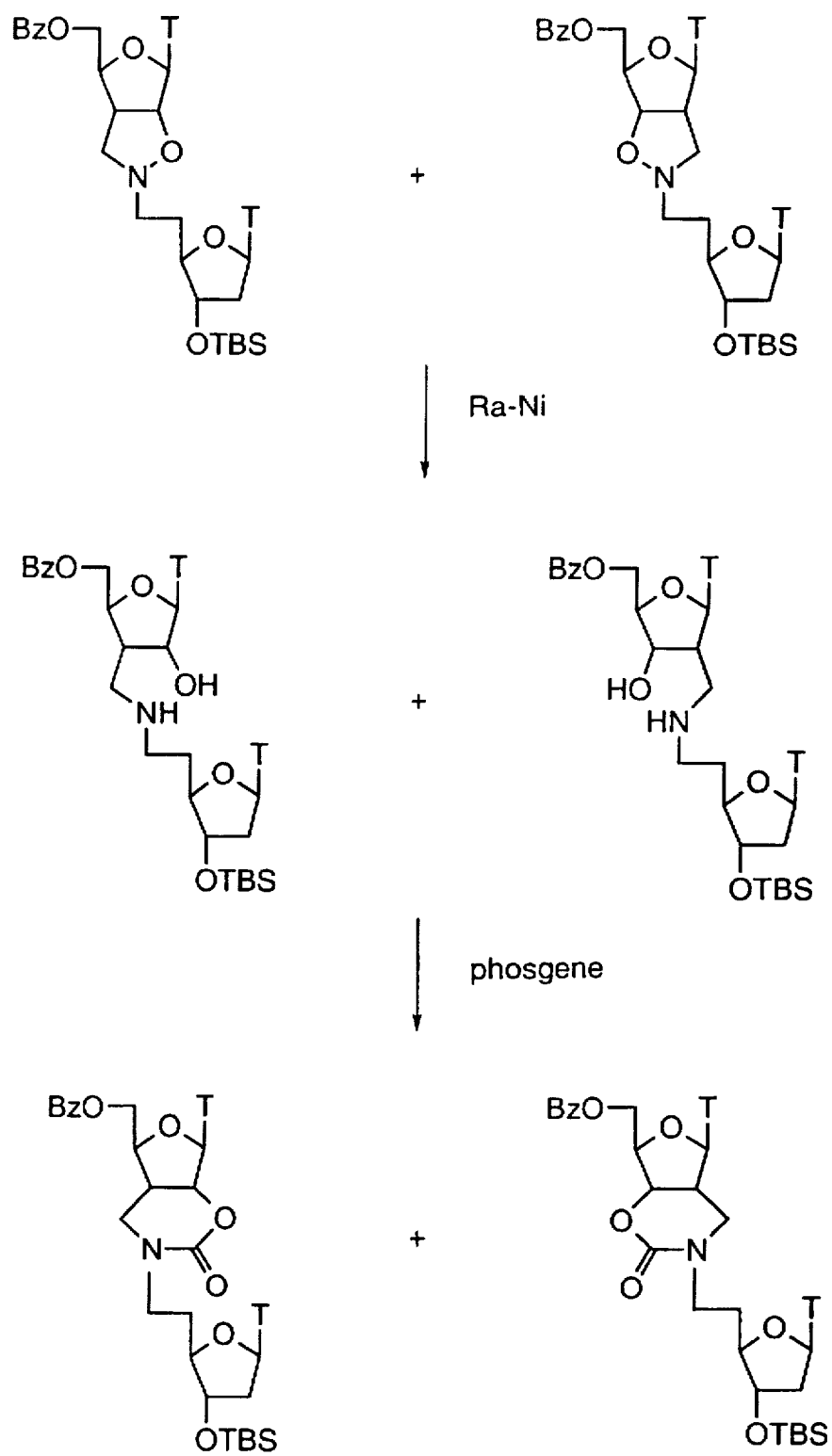
FIG. 9 describes the synthesis of a benzoyl synthon of a six member ring system of Example 11.

Synthesis of a TT cyclic carbamate dimer containing the 6-member ring structure is shown in FIG. 9. The starting material is obtained as described in application Ser. No. 763,130 and converted as shown. The TBS blocked compound is converted to the 5' DMT 3' H-phosphonate by reaction with (i) NaOMe, (ii) DMT/pyridine, (iii) TBAF and (iv) phosphytylation.

EXAMPLE 12

Synthesis of 5' DMT-T-Norcyclic Carbamate-T-3'-H-Phosphonate Dimer

Figure 10:
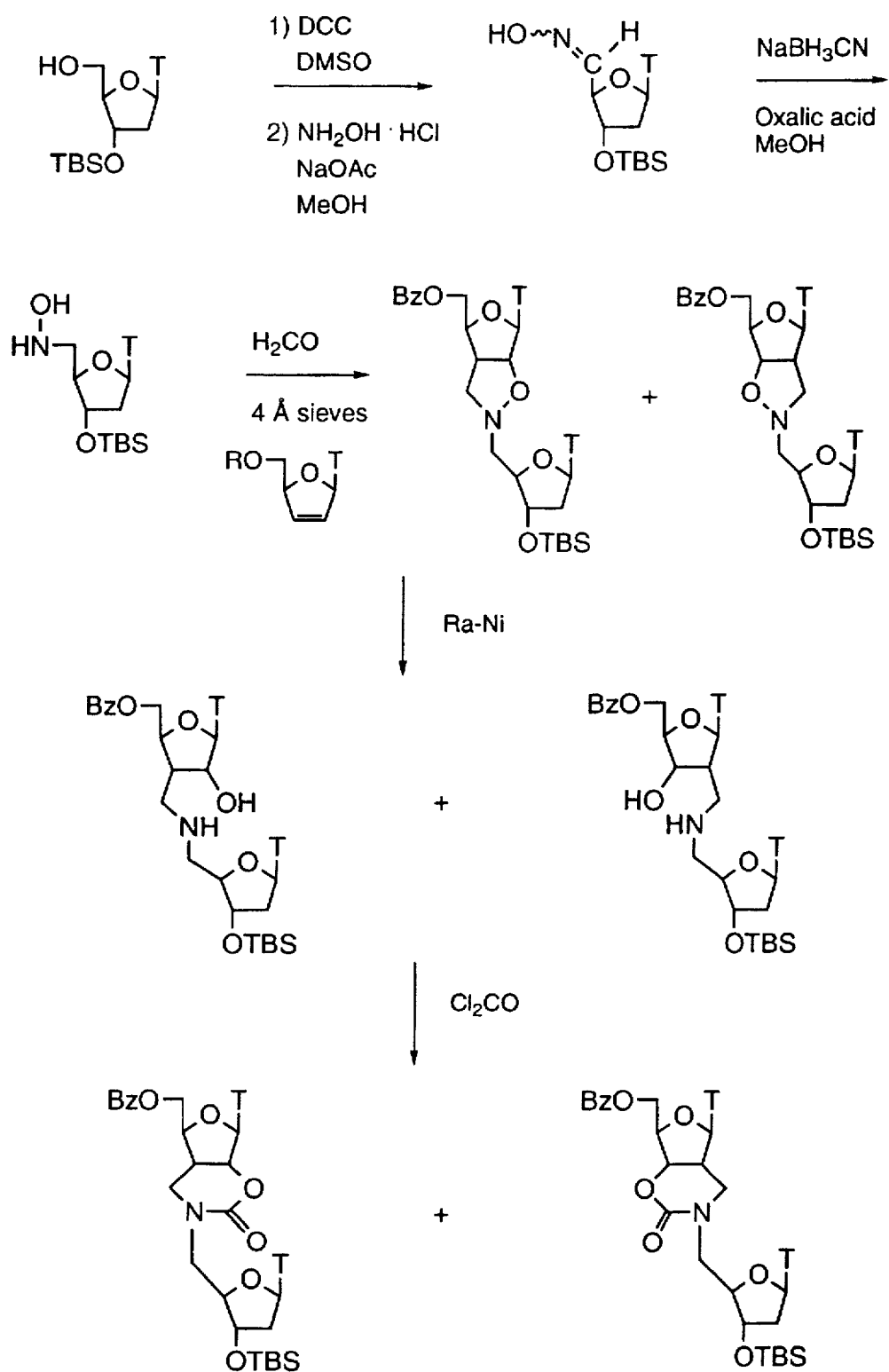
FIG. 10 describes the synthesis of a benzoyl synthon of a six member ring system of Example 12.

Synthesis of a TT norcyclic carbamate dimer containing the 6-member ring structure is shown in FIG. 10. The starting material is obtained as described in application Ser. No. 763,130 and converted as shown. The TBS blocked compound is converted to the 5' DMT 3' H-phosphonate by reaction with (i) NaOMe, (ii) DMT/pyridine, (iii) TBAF and (iv) phosphytylation.

EXAMPLE 13

Synthesis of 5' DMT-T-Ribothioacetal-T-3'-H-Phosphonate Dimer

Figure 11:
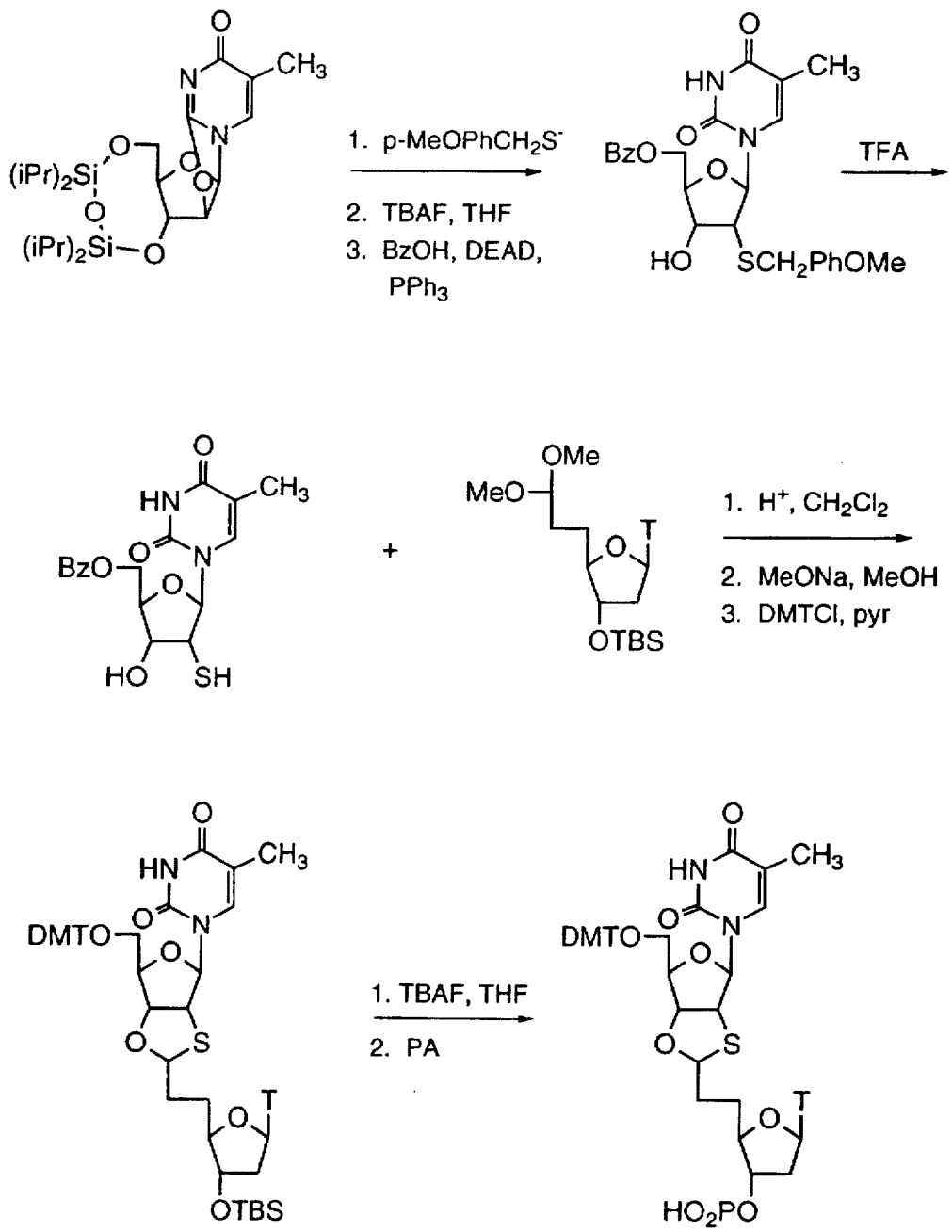
FIG. 11 describes the synthesis of a DMT synthon of 2' thioriboacetal of Example 13.

Synthesis of a TT ribothioacetal dimer containing the 5-member ring structure is shown in FIG. 11. The starting material is obtained from ribothymidine and converted as shown.

EXAMPLE 14

Synthesis of 5' DMT-T-Riboaminal-T-3'-H-Phosphonate Dimer

Figure 12:
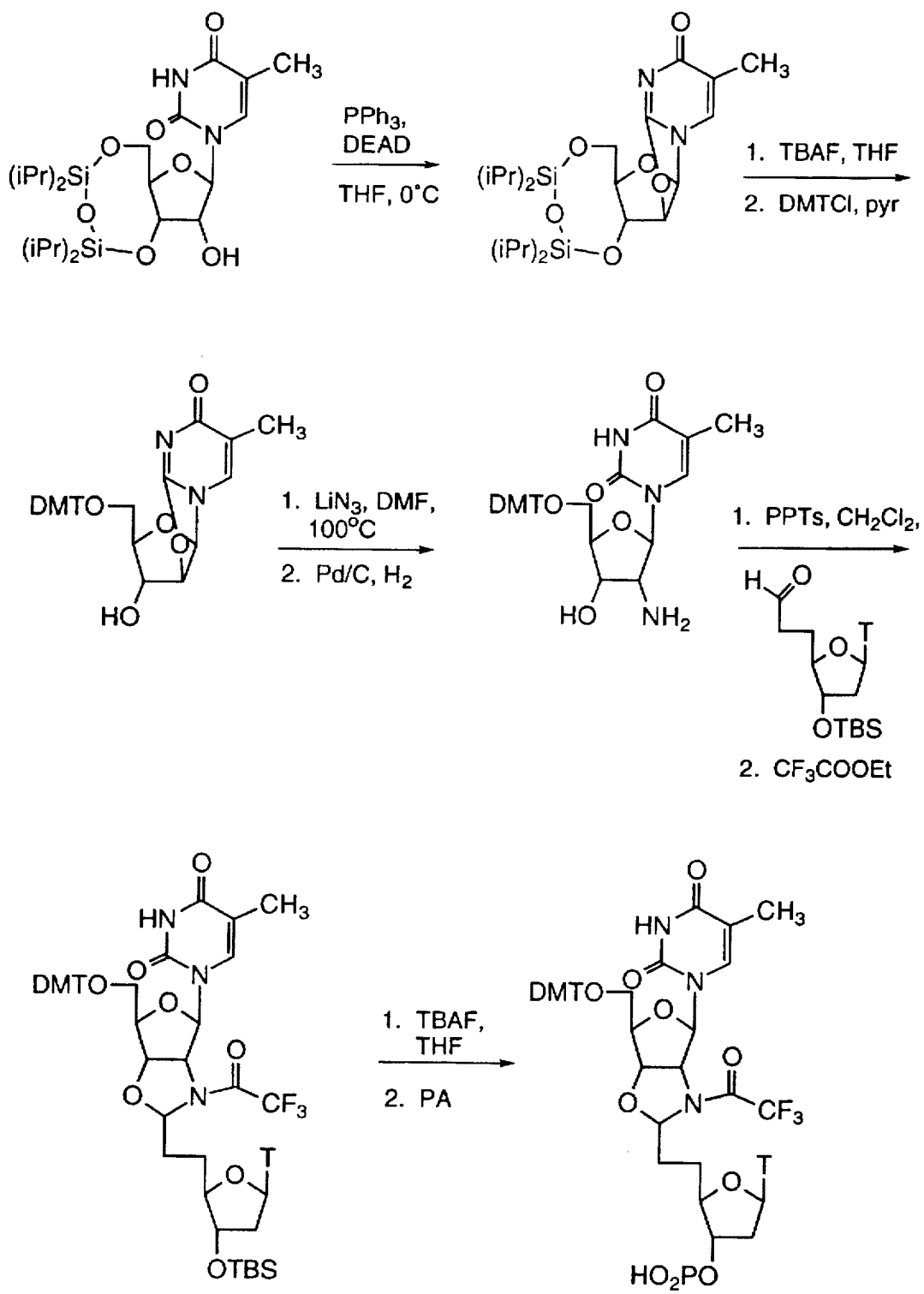
FIG. 12 describes the synthesis of a DMT synthon of 2' riboaminal of Example 14.

Synthesis of a TT riboaminal dimer containing the 5-member ring structure is shown in FIG. 12. The starting material is obtained from ribothymidine and converted as shown.

EXAMPLE 15

Synthesis of 5' DMT-T-Cyclic Aminal-T-3'-H-Phosphonate Dimer

Figure 13:
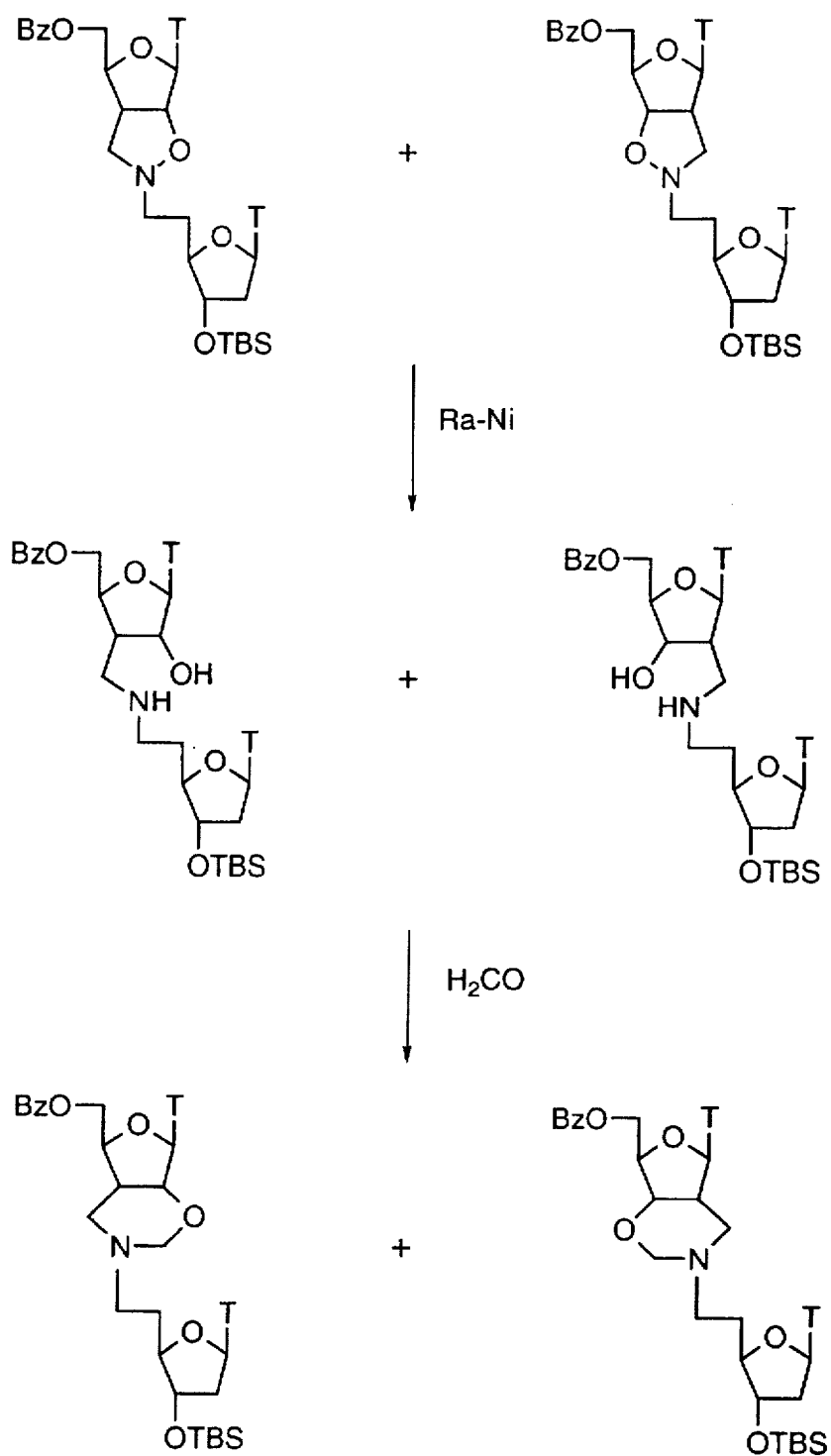
FIG. 13 describes the synthesis of a benzoyl synthon of a six member ring system of Example 15.

Synthesis of a TT cyclic aminal dimer containing the 6-member ring structure is shown in FIG. 13. The starting material is obtained as described in application Ser. No. 763,130 and converted as shown. The TBS blocked compound is converted to the 5' DMT 3' H-phosphonate by reaction with (i) NaOMe, (ii) DMT/pyridine, (iii) TBAF and (iv) phosphytylation.

EXAMPLE 16

Synthesis of 5' DMT-T-Norcyclic Aminal-T-3'-H-Phosphonate Dimer

Figure 14:
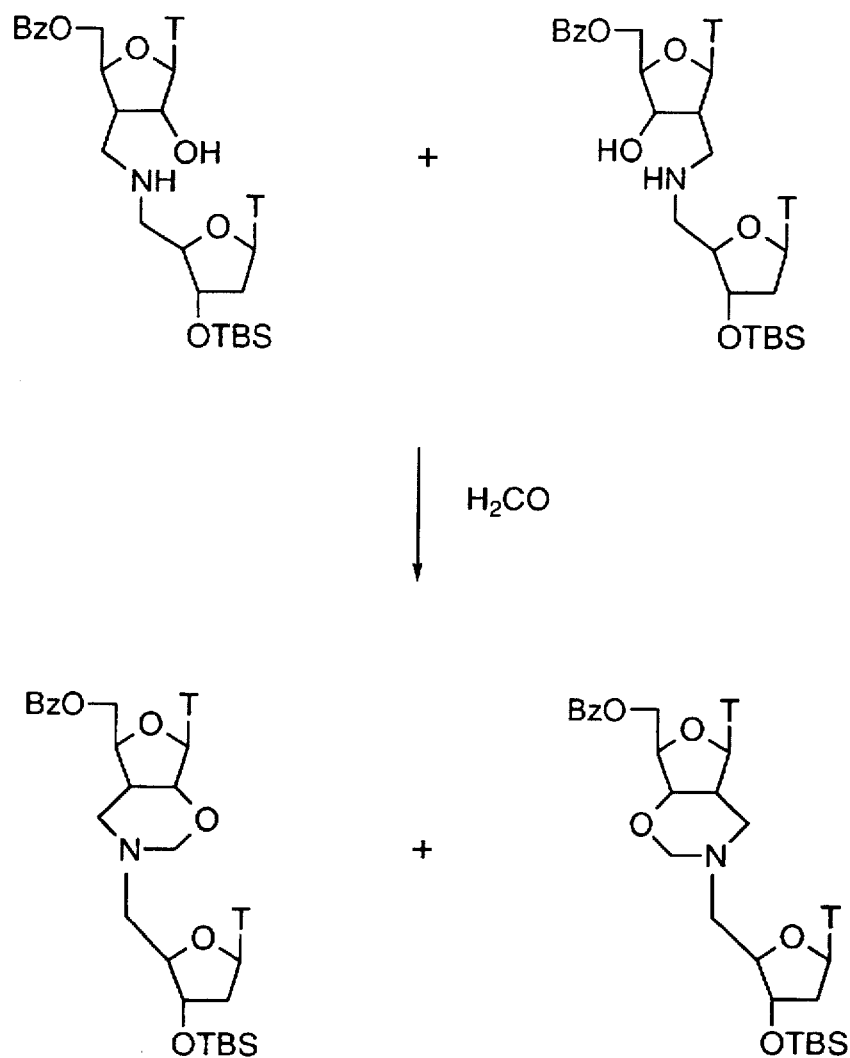
FIG. 14 describes the synthesis of a benzoyl synthon of a six member ring system of Example 16.

Synthesis of a TT norcyclic aminal dimer containing the 6-member ring structure is shown in FIG. 14. The starting material is obtained as described in Example 12 and converted as shown. The TBS blocked compound is converted to the 5' DMT 3' H-phosphonate by reaction with (i) NaOMe, (ii) DMT/pyridine, (iii) TBAF and (iv) phosphytylation.

EXAMPLE 17

Experimentals for FIG. 15

3'-O-Phenoxyacetylthymidine (1). To a solution of 5'-O-dimethoxytritylthymidine (27.23 g, 50.0 mmol) in pyridine (100 mL) at 0° C. was added phenoxyacetyl chloride (8.23 mL, 62.5 mL) dropwise, and the mixture was allowed to warm to ambient temperature over 3 hr. The reaction was quenched with methanol (ME, 25 mL) and concentrated in vacuo. The crude product was extracted with dichloromethane (DCM, 300 mL), washed with saturated aqueous sodium bicarbonate (SASB, 300 mL), dried ($Na_2SO_4$), and concentrated. Toluene (2×100 mL) was added, and the solution was concentrated. The residual oil was dissolved in 10% ME in DCM (275 mL) and treated with methanesulfonic acid (3.24 mL, 50.0 mmol). After 30 min the red solution was quenched with SASB (300 mL), and the organic layer was dried ($Na_2SO_4$) and concentrated. The crude product was dissolved in 1:1 ethyl acetate (EA): hexanes (H) (250 mL) and precipitated by cooling to −10° C. for 18 h. The mixture was filtered, and the precipitate dried under vacuum to afford 1 (11.4 g, 60.6%). $^1$H NMR δ $^{13}$C NMR ($D_6$ DMSO) δ 12.25, 36.41, 61.29, 64.59, 75.57, 83.68, 84.41, 109.75, 114.52, 121.23, 129.48, 135.77, 150.45, 157.54, 163.65, 168.42. HRMS (FAB) calcd. $C_{18}H_{21}N_2O_7$ (MH+) 377.1349; found 377.1355.

N4-benzoyl-5-methyl-2'-deoxy-3'-O-phenoxyacetylcytidine (2). The title compound was prepared in a manner analogous to that described for 1. $^1$H NMR ($CDCl_3$) δ 13.22 (bs, 1H), 8.29 (d, 2H, J=7.0 Hz), 7.70 (s, 1H), 7.52 (t, 1H, J=7.1 Hz), 7.43 (t, 2H, J=7.4 Hz), 7.31 (t, 2H, J=7.8 Hz), 7.01 (t, 1H, J=7.0 Hz), 6.92 (d, 2H, J=7.8 Hz), 6.22 (t, 1H, J=7.1 Hz), 5.50 (M, 1H0, 4.67 (s, 2H), 4.14 (d, 1H, J=2.1 Hz), 3.93 (dq, 2H, J=2.3, 11.9 Hz), 3.00 (bs, 1H), 2.46 (m, 2H), 2.07 (s, 3H). $^{13}$C NMR ($CDCl_3$) δ 168.71, 159.47, 157.44, 148.05, 137.42, 136.85, 132.52, 129.83, 129.60, 128.09, 121.95, 114.53, 112.27, 86.39, 85.11, 75.78, 65.08, 62.32, 37.39, 13.62. HRMS (FAB) for $C_{25}H_{26}N_3O_7$ (MH+) calcd. 480.1771, found 480.1778.

3'-O-phenoxyacetyl-1,2,5,6-tetradeoxy-1-(thymin-1-yl)-β-D-erythro-hept-5-enofuranuronal (3). To a solution of 1 (9.60 g, 25.5 mmol), dimethylsulfoxide (100 mL), and dicyclohexylcarbodiimide (10.5 g, 51.0 mmol) was added dichloroacetic acid (1.05 mL, 12.8 mmol). After stirring for 30 min, brine (100 mL) and ethyl acetate (EA, 200 mL) were added. The mixture was stirred vigorously for 15 min and filtered through a celite pad. To the filtrate was added SASB (100 mL). The layers were separated and the organic layer was dried ($Na_2SO_4$), concentrated, and dried under vacuum. To this aldehyde was added tetrahydrofuran (THF, 100 mL) and formylmethylene triphenylphosphorane (6.99 g, 23.0 mmol) and the solution was stirred for 1 h. SASB (100 mL) and EA (100 mL) were added, and the organic layer was separated, dried ($Na_2SO_4$), and concentrated. Flash chromatography (H:EA 100:0 to 0:100 to ME:EA 2.98) delivered the product (4.82 g, 47%). (Montgomery J. A., Thomas, H. J., *J. Org. Chem.* 1981, 46:594, U.S. Pat. No. 4,882,316).

3'-O-phenoxyacetyl-1,2,5,6-tetradeoxy-1-(N4-benzoyl-5-methylcytidin-1-yl)-β-D-erythro-hept-5-enofuranuronal (4). The title compound was prepared in a manner analogous to that described for 3. $^1$H NMR δ ($CDCl_3$) 2.14 (s, 3H), 2.38 (m, 1H), 2.55 (ddd, 1H, J=2.7, 5.8, 14.4 Hz), 4.70 (m, 1H), 4.74 (s, 2H), 5.32 (m, 1H), 6.29 (dd, 1H, J=5.9, 8.0 Hz), 6.38 (ddd, 1H, J=1.4, 8.0, 15.3 Hz), 6.92 (m, 2H), 6.95 (m, 1H), 7.04 (t, 1H, J=7.3 Hz), 7.23 (s, 1H), 7.33 (m, 2H), 7.45 (t, 2H, J=7.3 Hz), 7.55 (t, 1H, J=7.2 Hz), 8.32 (d, 2H, J=7.4 Hz), 9.64 (d, 1H, J=8.4 Hz), 13.26 (bs, 1H). $^{13}$C NMR δ ($CDCl_3$) HRMS (FAB) for $C_{27}H_{26}N_3O_7$ (MH+) calcd. 504.1771, found 504.1765.

3'-O-Phenoxyacetyl-1,2,5,6-tetradeoxy-1-(thymin-1-yl)-β-D-erythro-heptofuranuronal (3a). A solution of 3 (4.80 g, 12.0 mmol) and EA (200 mL) was purged with nitrogen, and palladium on carbon (10%, 480 mg) was added. The reaction was charged with hydrogen, evacuated and again charged with hydrogen. After stirring for 18 h under hydrogen (balloon), the mixture was filtered through celite, and the solid washed with EA (3×50 mL). The volatiles were removed under vacuum to afford the product 3a (4.62 g, 95.8%).

3+-O-phenoxyacetyl-1,2,5,6-tetradeoxy-1-(thymin-1-yl)-β-D-erythro-heptofuranuronal dimethylacetal (5). A solution of 3 (3.80 g, 9.44 mmol), MC (40 mL), trimethylorthoformate (5 mL), and pyridinium p-toluenesulfonate (50 mg, 0.2 mmol) was stirred for 18 h and concentrated. The residual oil was dissolved in MC (75 mL) and washed with SASB (75 mL). The organic layer was dried ($Na_2SO_4$) and concentrated, and the crude product was purified by flash chromatography (ME:MC 0:100 to 3:97) to provide 5 (3.07 g, 72.4%).

3'-O-phenoxyacetyl-1,2,5,6-tetradeoxy-1-(N4-benzoyl-5-methylcytidin-1-yl)-β-D-erythro-hept-5-enofuranuronal dimethylacetal (6). 6 was prepared essentially as described above for compound 5. $^1$H NMR δ ($CDCl_3$) 1.79 (m, 4H), 2.13 (s, 3H), 2.18 (m, 1H), 2.53 (ddd, 1H, J=1.7, 5.6, 14.2 Hz), 3.33 (m, 1H), 3.34 (s, 3H), 3.35 (s, 3H), 4.05 (m, 1H), 4.41 (m, 1H), 4.68 (s, 2H), 5.17 (m, 1H), 6.22 (dd, 1H, J=5.6, 8.2 Hz), 6.91 (d, 2H, J=8.0 Hz), 7.02 (t, 1H, 7.4 Hz), 7.33 (m, 3H), 7.53 (t, 1H, J=7.9 Hz), 8.31 (d, 2H, J=7.8 Hz), 13.29 (bs, 1H). $^{13}$C NMR δ ($CDCl_3$) HRMS (FAB) for $C_{27}H_{28}N_3O_7$ (MH+) calcd. 506.1927, found 506.1931.

3',5" Bisphenoxyacetyl T-T riboacetal. To a mixture of 7 (2.00 g, 5.09 mmol), 5 (1.77 g, 3.95 mmol) MC (25 mL), acetonitrile 15 mL), 4 Å molecular sieves (2 g) was added methanesulfonic acid (2.56 mL, 39.5 mmol). After 1 h, the mixture was filtered, and the filtrate was washed with SASB (75 mL), dried ($Na_2SO_4$), and concentrated. The crude product was purified by flash chromatography (ME:MC 0:100 to 4:96) to yield the product (2.00 g, 67%).

3',5" bisphenoxyacetyl T-$^{Bz}$C$^M$ riboacetal. $^1$H NMR δ ($CDCl_3$) 1.87 (s, 3H), 1.94 (m, 4H), 2.10 (s, 3H), 2.28 (m, 1H), 2.50 (ddd, 1H, J=1.5, 5.6, 14.0 Hz), 4.07 (m 1H), 4.42 (m, 3H), 4.60 (dd, 1H, J=2.9, 6.6 Hz), 4.66 (s, 3H), 4.68 (s,3H), 4.76 (dd, 1H, J=2.2, 6.5 Hz), 5.08 (m, 1H), 5.19 (m, 1H), 5.66 (d, 1H, J=2.3 Hz), 6.20 (dd, 1H, 5.8, 8.0 Hz), 6.88 (m, 4H), 7.00 (m, 2H), 7.08 (s, 1H), 7.30 (m, 5H), 7.45 (t 2H, J=7.7 Hz), 7.51 (t, 1H, J=7.4 Hz), 8.28 (d, 2H, J=7.3 Hz), 9.55 (bs, 1H), 13.23 (bs, 1H). $^{13}$C NMR δ ($CDCl_3$) 12.19, 13.59, 27.15, 29.10, 36.80, 64.80, 65.12, 65.18, 70.14, 77.26, 81.75, 83.97, 84.17, 84.47, 85.49, 93.32, 93.72, 107.39, 111.34, 112.25, 114.36, 114.46, 114.64, 121.87, 121.96, 128.05, 129.59, 129.85, 132.44, 135.92, 136.95, 137.81, 147.81, 150.25, 157.52, 158.10, 159.35, 163.74, 163.95, 168.50, 172.69, 172.72. HRMS (FAB) calcd. $C_{46}H_{46}N_5O_{14}$ (MH+) 880.3041; found 880.3054.

T-T Riboacetal (8). A solution of 3',5'-bisphenoxyacetyl T-T riboacetal (2.00 g, 2.57 mmol) and dioxane (25 mL) was treated with conc. NH₄OH (25 mL) for 18 h. The solution was evaporated; abs. ethanol was added (2×150 mL), and the solution was again evaporated. Flash chromatography on silica gel (ME:MC 2:98 to 10:90) delivered the product (1.14 g, 87.1%).

T-$^{Bz}C^M$ Riboacetal (9). Treatment of compound 7 as described for compound 8 gave a mixture of compounds 9 and 10 which were separated by silica gel chromatography (ME:MC 1:9 to 2:8). ¹H NMR δ (CD₃OD) 1.85 (s, 3H), 2.00 (m, 4H), 2.10 (s, 3H), 2.30 (m, 2H), 3.75 (m, 2H), 3.91 (m, 1H), 4.19 (m, 1H), 4.24 (m, 1H), 4.77 (m, 1H), 4.81 (m, 1H), 5.21 (m, 1H), 5.90 (d, 1H, J=2.6 Hz), 6.21 (t, 1H, J=6.6 Hz), 7.44 (t, 2H, J=7.4 Hz), 7.54 (t, 1H, J=7.10 Hz), 7.66 (s, 2H), 8.20 (d, 2H, J=7.3 Hz). ¹³C NMR δ (CD₃OD) 12.24, 13.81, 28.52, 31.10, 40.72, 63.15, 75.18, 83.15, 85.84, 87.41, 87.68, 88.04, 93.35, 94.85, 109.05, 111.68, 112.77, 129.24, 129.50, 130.65, 133.63, 139.40, 152.25, 166.31. HRMS (FAB) calcd. C₂₉H₃₃N₅O₁₀ (M+) 612.2306, found 612.2324.

T-$C^M$ Riboacetal (10). 10 was prepared essentially as described for 81, but used deprotected 6 as a starting material. δ 1.86 (s, 3H), 1.91 (m, 4H), 1.96 (s, 3H), 2.31 (m, 1H), 3.75 (m, 2H), 3.86 (m, 1H), 4.14 (M, 1H), 4.24 (q, 1H, J=3.4 Hz), 4.77 (dd, 1H, J=2.9, 6.5 Hz), 4.85 (m, 1H), 5.21 (m, 1H), 5.91 (d, 1H, J=2.9 Hz), 6.23 (t, 1H, J=6.5 Hz), 7.47 (s, 1H), 7.67 (s, 1H). ¹³C NMR δ (CD₃OD) 12.31, 12.37, 13.39, 28.61, 31.12, 41.20, 63.12, 75.28, 83.05, 85.82, 87.01, 87.51, 87.71, 93.33, 104.51, 109.06, 111.66, 139.38, 139.45, 152.22, 158.12, 166.29, 167.17. HRMS (FAB) calcd. C₂₂H₂₉N₅O₉ (MH+) 508.2044; found 508.2041.

5'-O-DMT-T-T Riboacetal (8a). A solution of 8 (600 mg, 1.18 mmol) and pyridine (25 mL) was concentrated and dried under high vacuum. Pyridine (5 mL) was added, followed by dimethoxytritylchloride (600 mg, 1.77 mmol), and the solution was stirred for 1 h. ME (5 mL) was added, and the solution was concentrated. The crude product was extracted with MC (50 mL), washed with SASB (50 mL), dried, and concentrated. Toluene (2×50 mL) was added, and the solution was concentrated. Chromatography on silica gel (ME:MC 0:100 to 4:96) afforded the product (610 mg, 63.8%).

5'-O-DMT-T-$^{Bz}C^M$ Riboacetal (9a). 9a was prepared essentially as described for 8a except that 9 was used as a starting material. ¹H NMR δ (CDCl₃) 1.41 (s, 3H), 1.88 (m, 4H), 2.09 (s, 3H), 2.17 (m, 1H), 2.47 (ddd, 1H, J=4.1, 6.0, 13.6 Hz), 3.37 (dd, 1H, J=2.6, 10.5 Hz), 3.54 (dd, 1H, J=2.1, 10.3 Hz), 3.79 (s, 6H), 3.94 (bs, 1H), 4.02 (m, 1H), 4.29 (m, 1H), 4.44 (s, 1H), 4.81 (m, 2H), 5.33 (m, 1H), 6.12 (d, 1H, J=3.9 Hz), 6.27 (t, 1H, J=6.5 Hz), 6.84 (d, 4H, J=8.7 Hz), 7.22–7.52 (m, 14H), 8.29 (d, 2H, J=7.4 Hz), 9.96 (bs, 1H). ¹³C NMR δ (CDCl₃). HRMS (FAB) calcd. C₅₀H₅₁N₅O₁₂ (M+) 913.3534, found 913.3543.

5'-O-DMT-T-T Riboacetal H-Phosphonate (12). To a solution 11 (1.0M in DCM, 0.40 mL), DCM (5 mL), and pyridine (1.0 mL) at 0° C. was added 8a (0.18 g, 0.20 mmol) in DCM (2 mL). The reaction mixture was stirred at room temperature for 2 h, diluted with DCM (10 mL), and quenched with triethylammonium bicarbonate (TEAB, 1M aqueous solution, 30 mL). The organic phase was dried (Na₂SO₄) and concentrated. Subsequent purification by flash chromatography in TEA/ME/DCM (0.5:2:97.5–0.5:10:89.5) delivered 12 (0.58 g, 94.5%). ¹H NMR δ (D₆ DMSO) 1.16 (t, 9H, J=7.3 Hz), 1.60 (s, 3H), 1.74 (s, 3H), 1.78 (m, 4H), 2.19 (bm, 2H), 3.02 (q, 6H, J=7.2 Hz), 3.40 (m, 2H), 3.72 (s, 6H), 3.84 (m, 1H), 4.20 (m, 1H), 4.47 (m, 1H), 4.71 (dd, 1H, J=3.8, 6.4 Hz), 4.96 (dd, 1H, J=1.8, 6.6 Hz), 5.12 (bs, 1H), 5.67 (s, ½H), 5.86 (d, 1H, J=1.7 Hz), 6.12 (t, 1H, J=7.1 Hz), 6.86 (dd, 4H, J=6.0, 8.5 Hz), 7.18–7.39 (m, 11H), 7.61 (bs, 1.5H), 11.31 (bs, 1H), 11.40 (bs, 1H).

5'-O-DMT-T-$^{Bz}C^M$ Riobacetal H-Phosphonate (13). 13 was prepared essentially as described for compound 12. ¹H NMR δ (D₆ DMSO) 1.18 (t, 9H, J=7.3 Hz), 1.61 (s, 3H), 1.80 m, 4H), 1.99 (s, 3H), 2.33 (m, 2H), 3.04 q, 6H, J=7.3 Hz), 3.50 (m, 2H), 3.72 (s, 6H), 3.92 (m, 1H), 4.23 (m, 1H), 4.51 (m, 1H), 4.73 (dd, 1H, J=3.9, 6.5 Hz), 4.99 (dd 1H, J=2.0, 6.5 Hz), 5.15 (m, 1H), 5.70 (s, ½H), 5.88 (d, 1H, J=1.9 Hz), 6.15 (t, 1H, J=6.7 Hz), 6.86 (dd, 4H, J=5.8, 8.6 Hz), 7.18–7.73 (m, 14.5H), 8.17 (bd, 2H, J=6.4 Hz), 11.41 (bs, 1H). ³¹P NMR δ (D₆ DMSO) 0.38 (dd, J$_{P-H}$=585 Hz, J$_{P-O-C-H}$=9 Hz).

EXAMPLE 18

Figure 16:
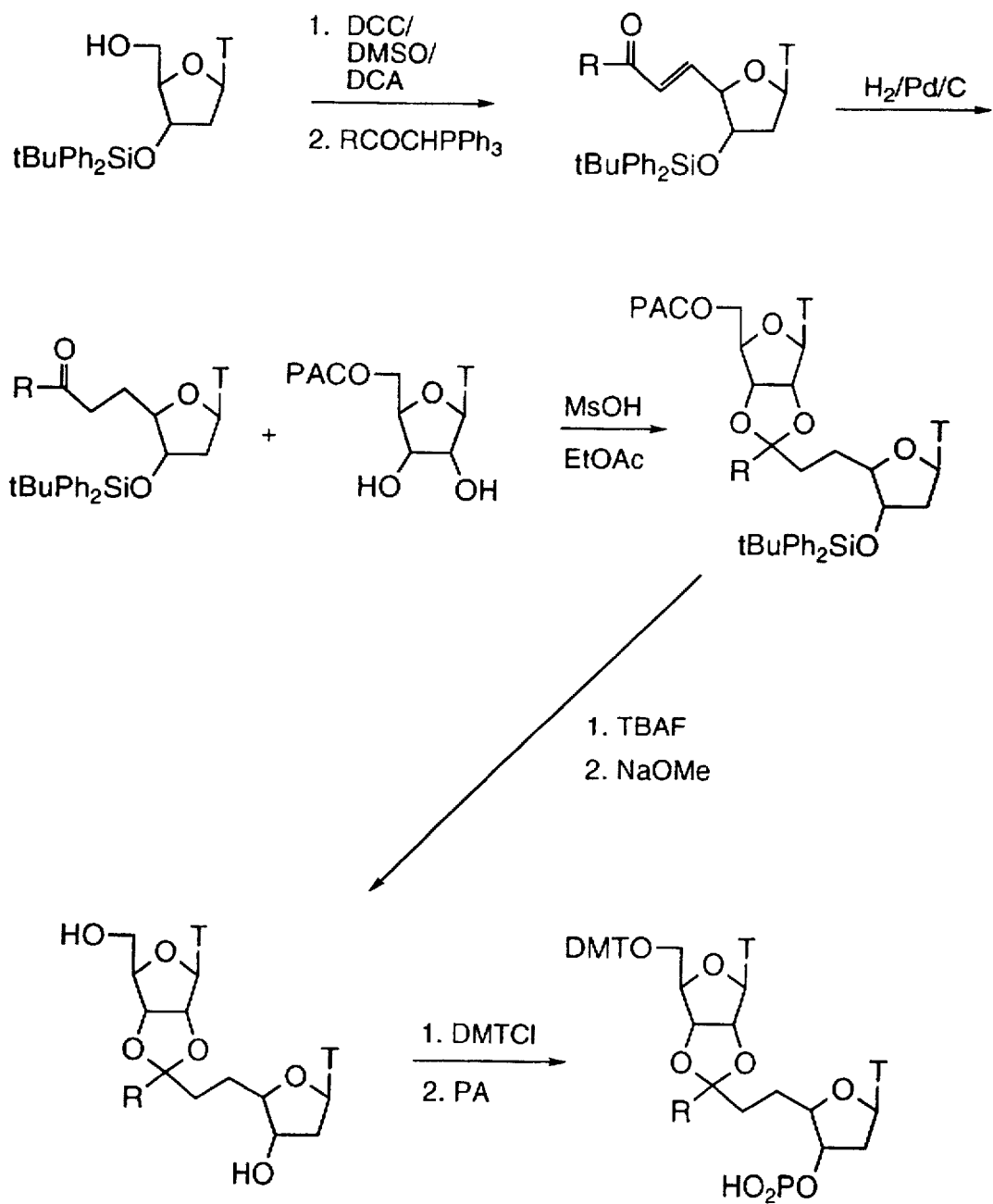
FIG. 16 describes the synthesis of a riboketal synthon.

Experimentals for FIG. 16.

Unsaturated methylketone. To a solution of the alcohol (4.80 g, 10.0 mmol), dimethylsulfoxide (50 mL), and dicyclohexylcarbodiimide (4.11 g, 20.0 mmol) was added dichloroacetic acid (0.41 mL, 5.0 mmol). After stirring for 30 min, pyridine (0.41 mL) was added, followed by acetylmethylene triphenylphosphorane (3.50 g, 11.0 mmol). The solution was stirred for 18 h, and brine (100 mL) and ethyl acetate (EA, 200 mL) were added. The mixture was stirred vigorously for 15 min and filtered through a celite pad. To the filtrate was added SASB (100 mL). The layers were separated and the organic layer was dried (Na₂SO₄), concentrated, and dried under vacuum. Flash chromatography (H: EA 60:40) delivered the product (4.35 g, 83.9%). (Montgomery, J. A., Thomas, H. J. Org. Chem. 1981, 46:594. U.S. Pat. No. 4,882,316).

Methyl Ketone. A solution of unsaturated ketone (4.35 g, 8.38 mmol) and EA (200 mL) was purged with nitrogen, and palladium on carbon (10%, 435 mg) was added. The reaction was charged with hydrogen, evacuated and again charged with hydrogen. After stirring for 18 h under hydrogen (balloon), the mixture was filtered through celite, and the solid washed with EA (3×50 mL). The volatiles were removed under vacuum to afford the product (4.01 g, 91.8%).

5'-PAC-3"-TBDPS-Methylketal dimer. To a solution of the ketone (650 mg, 1.24 mmol), diol (588 mg, 1.50 mmol), EA (25 mL) and 4 Å molecular sieves was added methanesulfonic acid (1 mL). The mixture was stirred for 1 h and filtered. The filtrate was washed with SASB (50 mL), dried (Na₂SO₄), concentrated, and chromatographed on silica gel (1:99 ME:MC to 4:96 ME:MC) to deliver the dimer (805 mg, 72%).

Methylketal dimer. A solution of the protected dimer (300 mg, 0.335 mmol) in THF (25 mL), was treated with TBAF (1.0M in THF, 1.0 mL) and the resulting solution was stirred for 18 h. ME (15 mL) was added, and the solution was concentrated and chromatographed on silica gel (ME:MC 2:98–12:88) to afford the product.

5'-O-DMT T-T Methyl Ketal Dimer. A solution of 8 (600 mg, 1.18 mmol) and pyridine (25 mL) was concentrated and dried under high vacuum. Pyridine (5 mL) was added, followed by dimethoxytritylchloride (600 mg, 1.77 mmol), and the solution was stirred for 1 h. ME (5 mL) was added, and the solution was concentrated. The crude product was extracted with MC (50 mL), washed with SASB (50 mL), dried, and concentrated. Toluene (2×50 mL) was added, and the solution was concentrated. Chromatography on silica gel (ME:MC 0:100 to 4:96) afforded the product (610 mg, 63.8%).

5'-O-DMT T-T Methyl Ketal H-Phosphonate Dimer. The DMT-protected dimers were treated with van Boom's reagent as described before and purified by column chromatography and eluted with $Et_3N/MeOH/CH_2Cl_2$.

EXAMPLE 19

Figure 17:
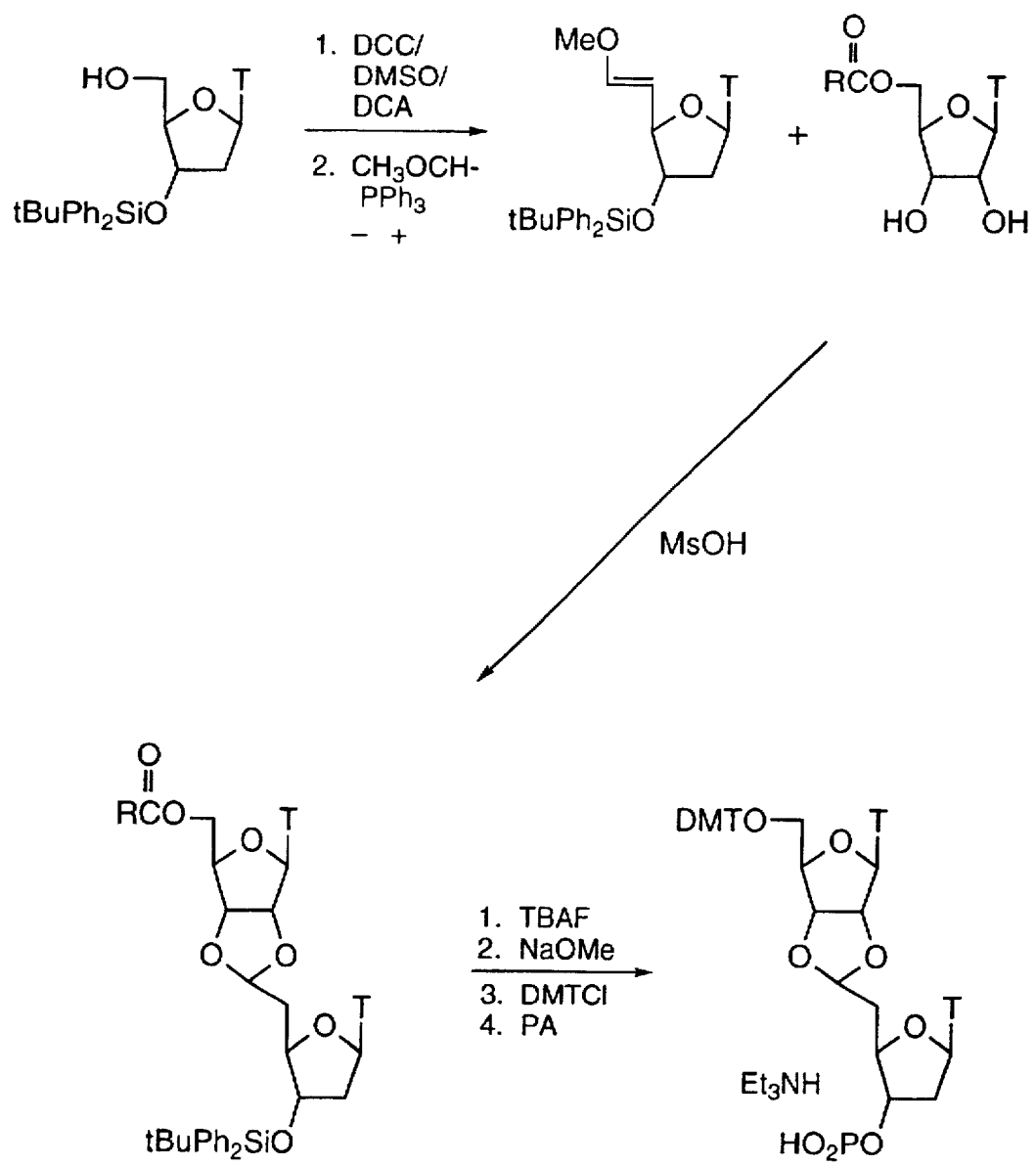
FIG. 17 describes the synthesis of a nor riboacetal synthon.

Experimentals for FIG. 17

Methoxy vinylether. The alcohol was oxidized to the aldehyde as previously described. To a solution of methoxymethyltriphenylphosphonium chloride (5.14 g, 15 mmol) in THF at 0° C. was added n-butyllithium (1.5M, 6.25 mmol) and the solution was stirred for 30 min. The mixture was partitioned between EA (100 mL) and SASB (100 mL), and the crude product was extracted, dried, concentrated, and chromatographed (ME:MC 0:100 to 4:96) to yield the product (1.25 g, 49%).

5'-PAC-3"-TBDPS-nor riboacetal dimer. The dimer was prepared as described for the methyl ketal.

Nor riboacetal dimer. The dimer was prepared as described for the methyl ketal.

5'O-DMT T-T Nor-riboacetal dimer. The dimer was prepared as described for the methyl ketal.

5'O-DMT T-T Nor riboacetal H-phosphonate dimer. The DMT-protected dimers were treated with van Boom's reagent as described before and purified by column chromatography and eluted with $Et_3N/MeOH/CH_2Cl_2$.

EXAMPLE 20

Figure 18:
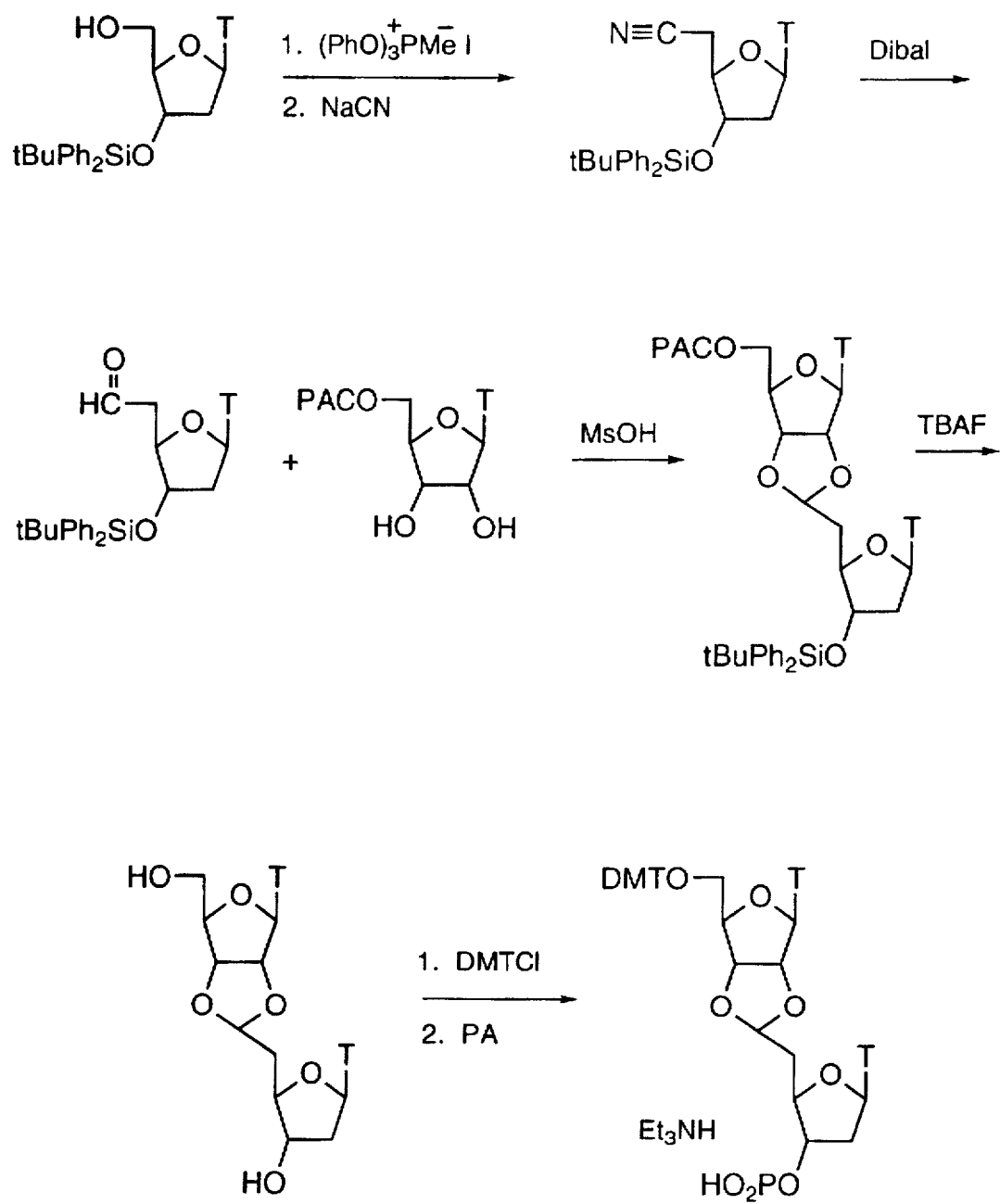
FIG. 18 describes the synthesis of a nor riboacetal synthon.

Experimentals for FIG. 18

Nitrile. To a solution of 3'-silylthymidine (2.33 g, 5.0 mmol) in DMF (25 mL) was added methyltriphenoxyphosphonium iodide (2.92 g, 6.5 mmol) and the solution was stirred for 18 h. Sodium cyanide (490 mg, 100 mmol) was added and the solution was stirred for 18 h. ME was added, and the solution was concentrated. The solution was partitioned between EA (100 mL) and SASB (100 mL) and the crude product was washed with aqueous thiosulfate (100 mL), dried, concentrated, and chromatographed (EA:H 4:6) to deliver the product (1.14 g, 49%).

Aldehyde. To a solution of nitrile (1.14 g, 2.45 mmol) in tuluene at −78° C., was added Dibal (1.5M, 7.5 mL), and the solution was stirred for 30 min. Ethanol (2 mL) was added, followed by sodium fluoride (3.0 g), and water 2 (mL). The mixture was filtered through celite, and the crude product was extracted with EA (100 mL), dried, concentrated, and chromatographed (EA:H 4:6) to yield the product (625 mg).

5'-PAC-3"-TBDPS-nor riboacetal dimer. The dimer was prepared as described for the methyl ketal.

Nor riboacetal dimer. The dimer was prepared as described for the methyl ketal.

5'O-DMT T-T Nor-riboacetal dimer. The dimer was prepared as described for the methyl ketal.

5'O-DMT T-T Nor-riboacetal H-phosphonate dimer. The DMT-protected dimers were treated with van Boom's reagent as described before and purified by column chromatography and eluted with $Et_3N/MeOH/CH_2Cl_2$.

EXAMPLE 21

Figure 19:
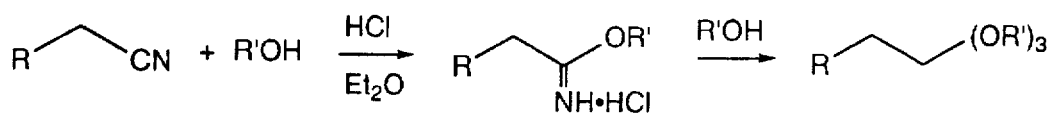
FIG. 19 describes the synthesis of an orthoester synthon.
Figure 19:
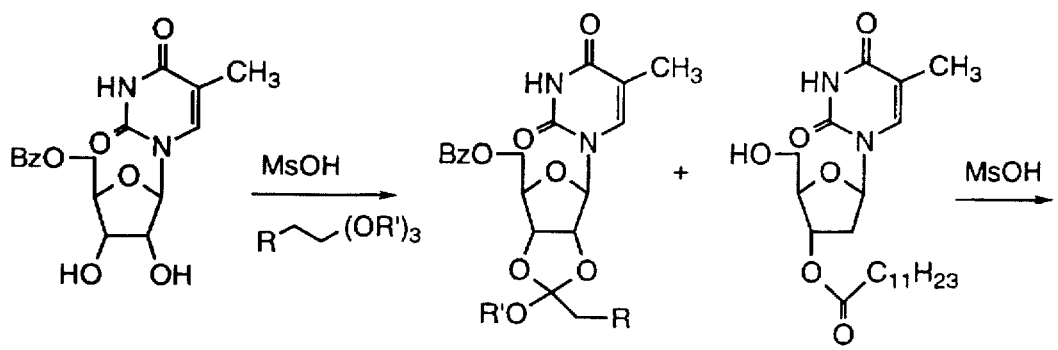
Figure 19:
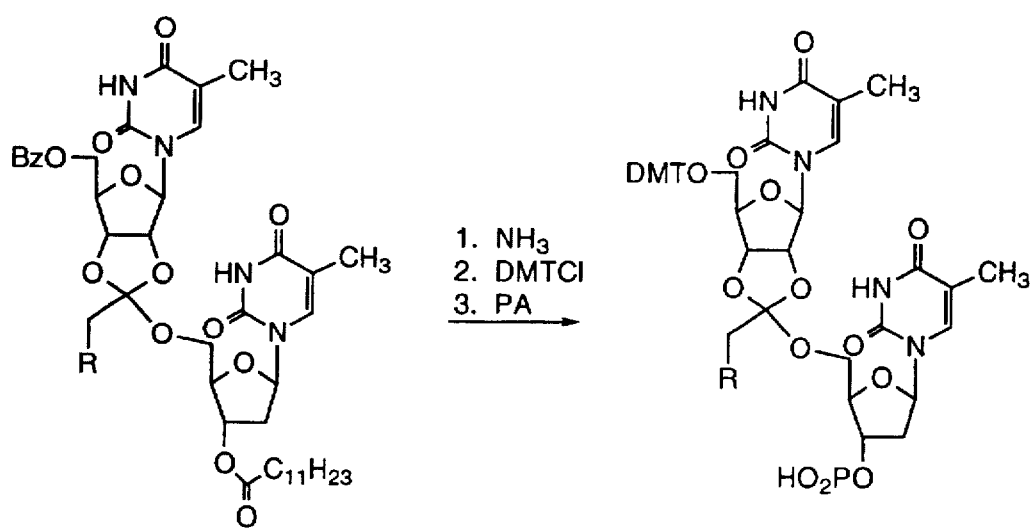
Figure 20:
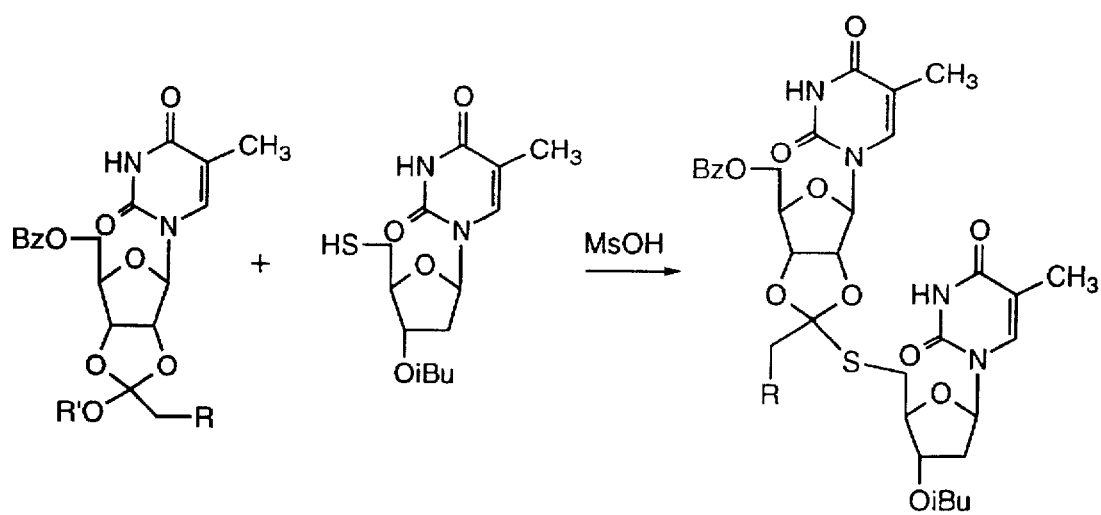
FIG. 20 describes the synthesis of a 5" thioorthoester synthon.
Figure 20:
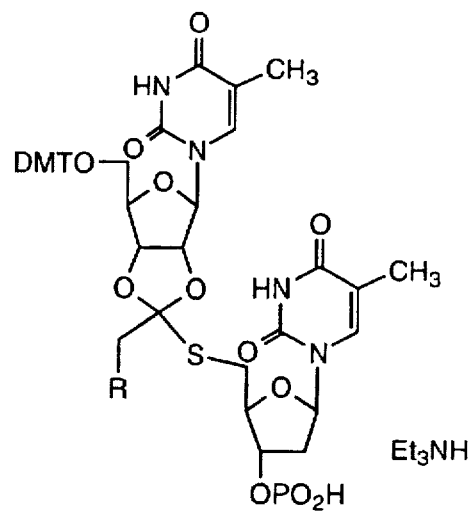

Experimentals for FIG. 19

2-Cyanomethylacetylimidate. Malononitrile (30.0 g, 0.50 mol) was dissolved in $Et_2O$ (anhy, 300 mL) and methanol (anhy, 19 mL) and the solution was cooled to 0° C. HCl (anhy) passed through solution for 10 minutes during which time a white ppt formed. The flask wassealed and stored at 0°–5° C. for 12 hrs. The solid was filtered and washed with $Et_2O$ to yield a white powder.

2-Cyanotrimethylorthoacetate. Methyl imidate ester (9.8 g, 72 mmol) was dissolved in MeOH (anhy, 150 mL) and the solution stirred for 18 hrs at room temperature. The solvent was removed and the residue partially dissolved in $Et_2O$ (50 mL) and the solid filtered and discarded. The filtrate was washed with $NaHCO_3$ (sat) and brine. The organic layer was decanted, dried over $K_2CO_3$, filtered, and reduced to a clear oil that was vacuum distilled (40°–45° C. at approx 0.2 Torr) to yield a clear, colorless oil.

5'-Benzoyl-2',3'-(2-cyanomethyl orthoacetate)-5-methyluridine. 5'-Benzoyl-5-methyluridine (1.46 g, 4.0 mmol) dissolved at $CH_2Cl_2$ (10 mL) and 2-cyanomethyl orthoacetate (1.7 g, 12 mmol) and MsOH (trace) added. The solution was stirred for 3 h after which time TEA (2 mL) was added. The solution was diluted with $CH_2Cl_2$ and washed with $NaHCO_3$ (sat) and brine. The organic layer was decanted, dried, filtered, and reduced to a white foam that was subjected to column chromatography and eluted with 80% EtOAc/hex to yield a white foam.

5'-Benzoyl-2',3'-(2-cyano orthoacetate)-thymidine-5'-thymidine dimer. 5'-Benzoyl-2',3'-orthoester and 3'-laurylthymidine were dissolved in dichloroethane and sieves (4 A) added. MsOH (trace) added and the solution was heated at reflux in a flask that was fitted with a sohxlet extractor charged with CaH. The solution was heated at reflux for 3 h. The solution was cooled and TEA (1 mL) added and solution diluted with $CH_2Cl_2$ and washed with $NaHCO_3$ (sat) and brine. The organic layer was decanted, dried, and reduced to a yellow foam. This foam was subjected to column chromatography and eluted with iso-propanol/$CH_2Cl_2$ (0–4% iPOH) to separate both diastereomers.

5'-Hydroxyl-2',3'-(2-cyano orthoacetate)-thymidine-5'-thymidine dimer. The acylated dimers were deprotected as described before with MeONa/MeOH and purified by column chromatography and eluted with iPOH/$CH_2Cl_2$.

5'-Dimethoxytrityl-2',3'-(2-cyano orthoacetate)-thymidine-5'-thymidine dimer. The deprotected dimers were reacted with DMTCl in pyridine as described before and purified by column chromatography and eluted with iPOH/$CH_2Cl_2$.

5'-Dimethoxytrityl-2',3'-(2-cyano orthoacetate)-thymidine-5'-thymidine dimer H-phosphonate. The DMT-protected dimers were treated with van Boom's reagent as described before and purified by column chromatography and eluted with MeOH/$CH_2Cl_2$.

EXAMPLE 22

Figure 21:
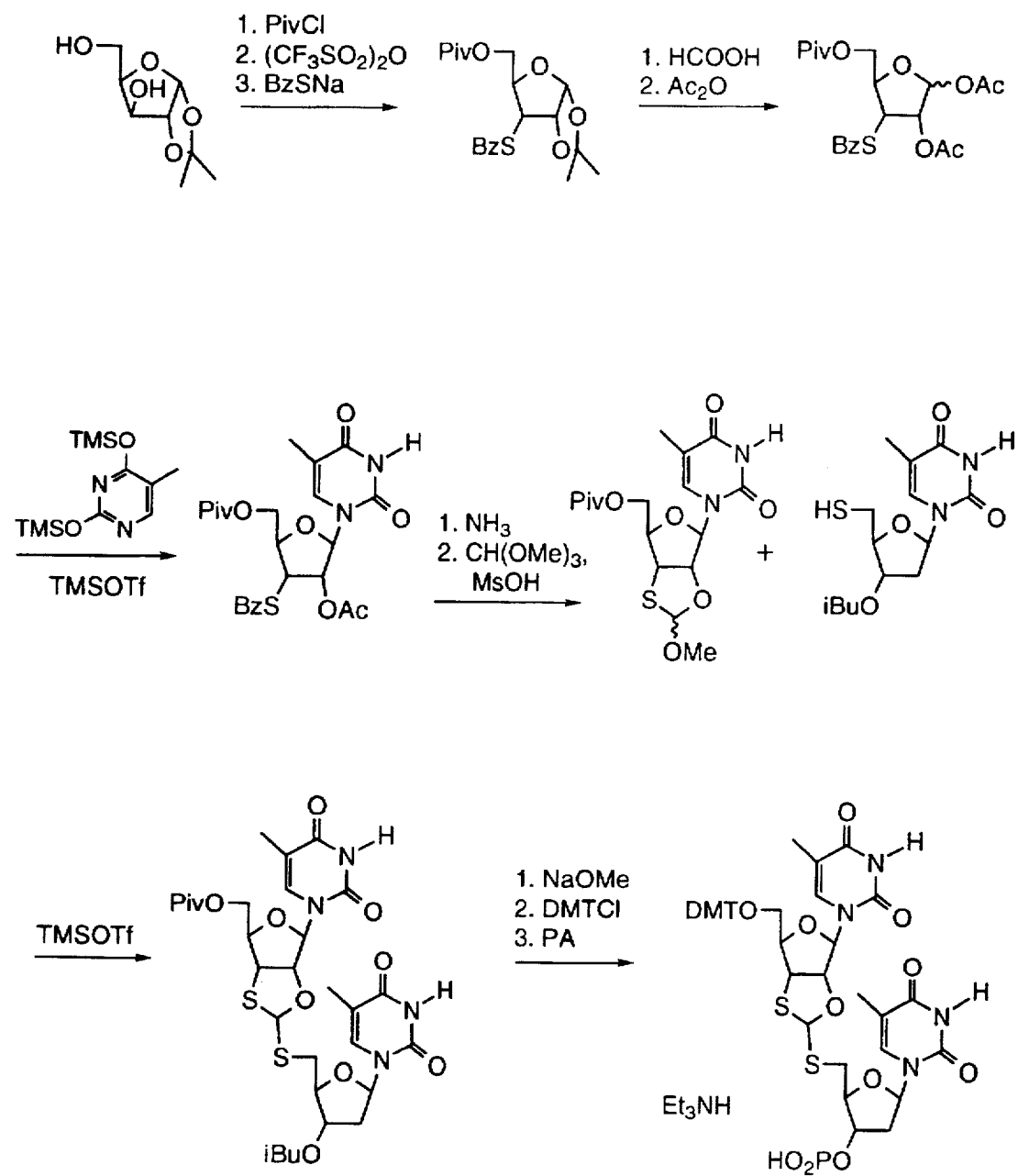
FIG. 21 describes the synthesis of a 3',5" dithioorthoester synthon.
Figure 22A:
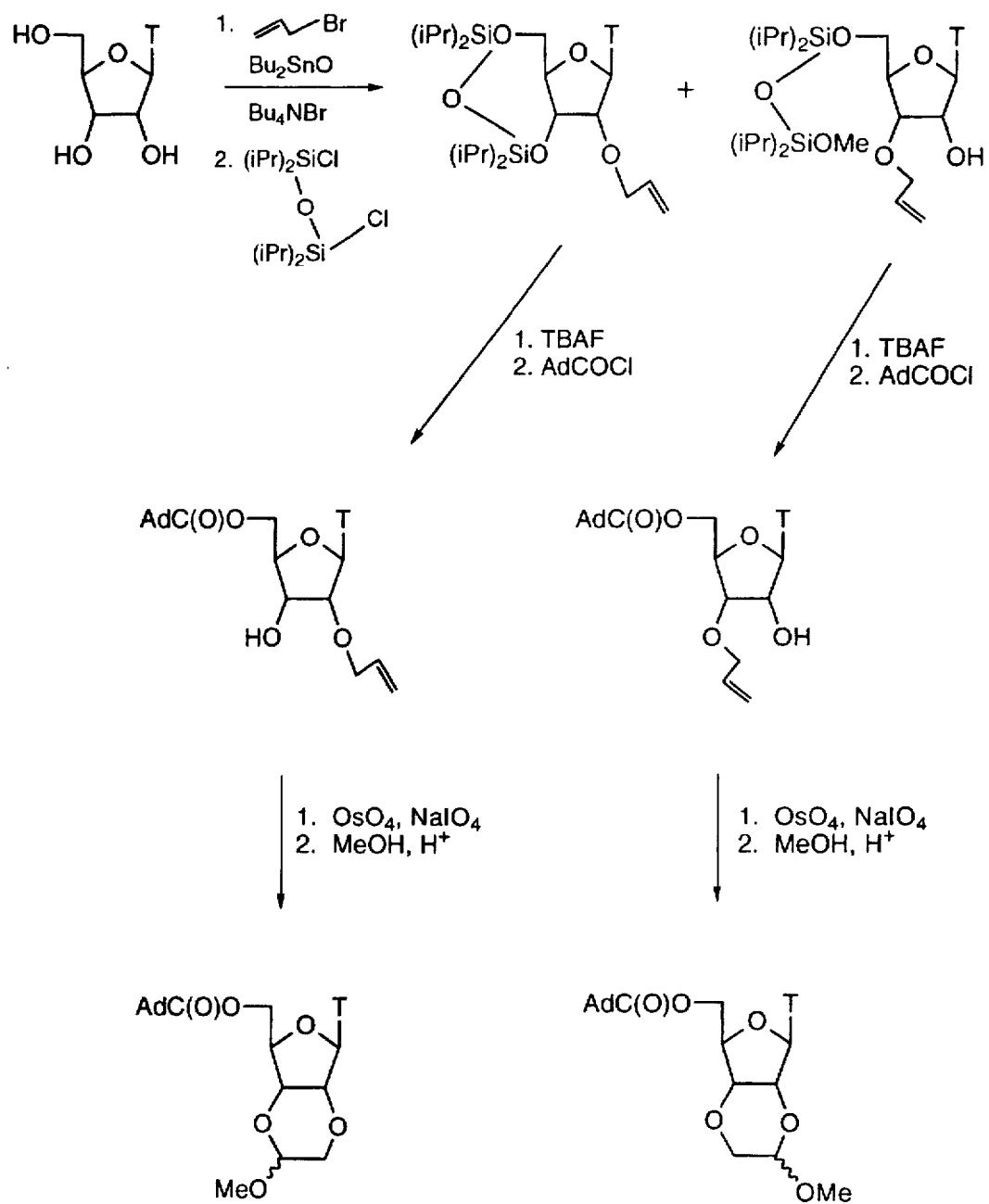
FIG. 22 describes the synthesis of a six member ring system.
Figure 22B:
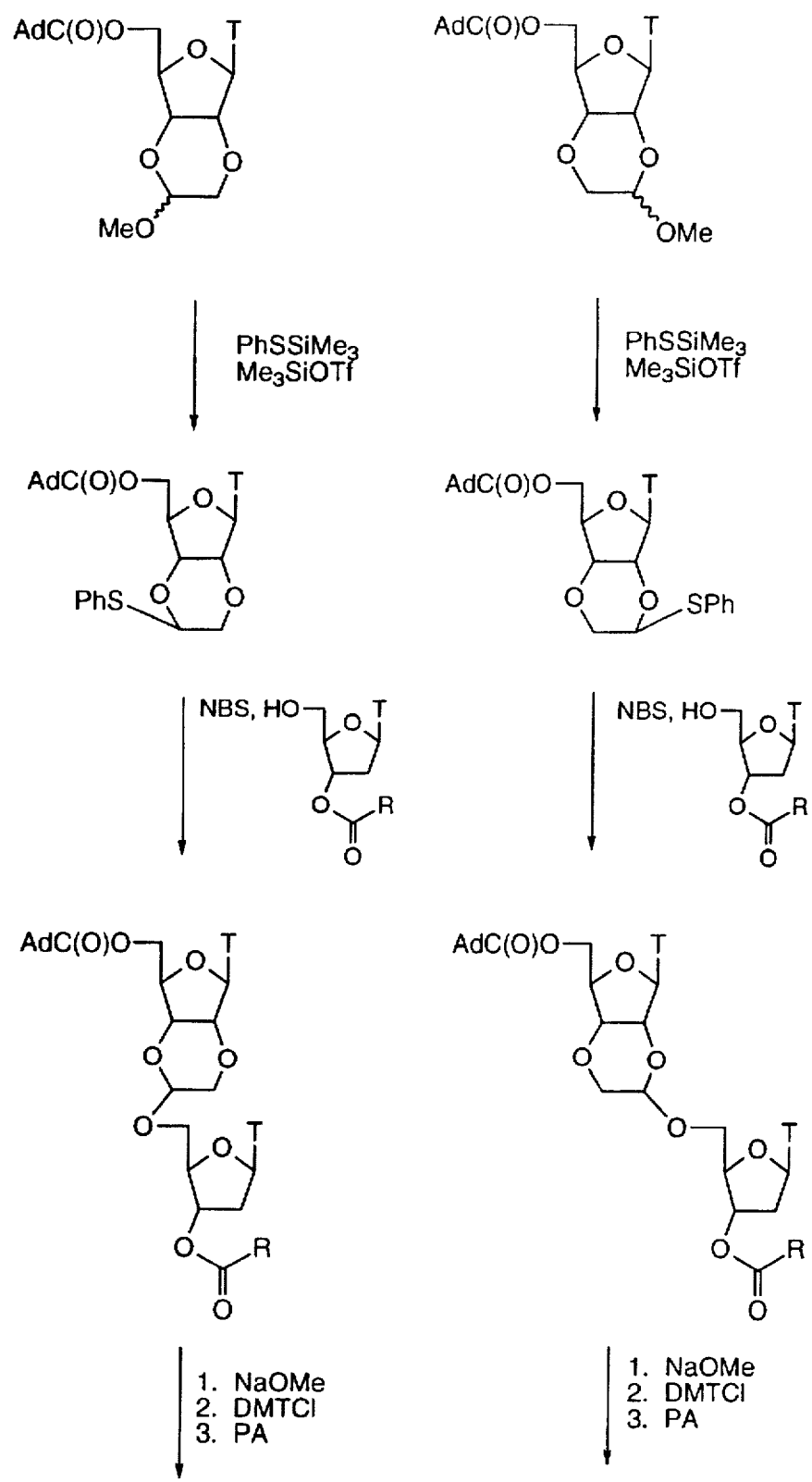

Experimentals for FIG. 21

1,2-Di-O-isopropylidene-5-O-pivaloyl-α-D-xylofuranose. A mixture of 1,2-Di-O-isopropylidene-α-D-xylofuranose (19.0 g, 0.1 mol) and pyridine (20 mL) in 200 mL of DCM was cooled to 0° C. and pivaloyl chloride (13.2 g, 0.11 mol in 20 mL of dry DCM) was added. The mixture was stirred at 0° C. for 15 min and at room temperature for 2 h. The mixture was poured into water and extracted with DCM. The organic layer was washed with water and brine, dried over sodium sulfate, filtered and then concentrated. The compound was then crystallized from hexane (200 mL) to yield white prisms; yield=24.9 g (91%).

3-S-Benzoyl-3-deoxy-1,2-di-O-isopropylidene-5-O-pivaloyl-β-D-xylofuranose. 1,2-di-O-isopropylidene-5-O- pivaloyl-α-D-xylofuranose (5.48 g, 20 mmol) was dissolved in 200 mL dry MC and 10 mL of dry pyridine. The solution was cooled to 0° C. and triflic anhydride (5.64 mL in 10 mL DCM) was added dropwise. After 1 h stirring at 0° C. the reaction mixture was poured into 5% sodium bicarbonate. The organic phase was washed with water and dried over sodium sulfate, filtered and reduced. The residue was dissolved in DMF and added to a solution of sodium thiobenzoate (2.4 g, 60% sodium hydride and 11 g, thiobenzoic acid) in 200 mL of dry DMF. The reaction mixture was stirred at room temperature for 30 min. DMF was then removed and the residue was dissolved in ethyl acetate and washed with water (3×), and dried over sodium sulfate, filtered, and reduced. The residue was purified by column chromtography and eluted with 17% EtOAc/hexane to yield 4.73 g (62%).

3-S-Benzoyl-3-deoxy-1,2-di-O-acetyl-5-O-pivaloyl-D-xylofuranose. 3.82 g (10 mmol) of 3-S-Benzoyl-3-deoxy-1, 2-di-O-isopropylidene-5-O-pivaloyl-β-D-xylofuranose in 100 mL of 80% formic acid in $H_2O$ and heated at 50° C. for 1 h. The solvent was removed under reduced pressure. The residue was co-evaporated with 20 mL of dry butanol, 20 mL of dry toluene, and then dissolved in 40 mL of dry pyridine. Acetic anhydride (5 mL, 53 mmol) was then added to the solution at 0° C. and the mixture was stirred for 1 h. The reaction mixture was then poured into dilute aqueous sodium bicarbonate solution and extracted with ethyl acetate. The organic phase was washed with dilute HCl solution, water (2×), and dried over sodium sulfate, filtered and reduced. This residue was purified by column chromatography and eluted with 17% EtOAc/hexane to yield 3.79 g (89%).

2'-O-Acetyl-3'-S-benzoyl-3'-deoxy-5'-O-pivaloyl-β-D-xylofuranosylthymine. 1.26 g (10 mmol, 1.1 eq.) thymine was silylated with 6.4 g (40 mmol) BSA in 50 mL of dry acetonitrile at 60° C. until a clear solution formed (about 30 min). 3-S-benzoyl-3-deoxy-1,2-di-O-acetyl-5'-O-pivaloyl-D-xylofuranose (3.79 g, 8.9 mmol) was added into the solution. TMSO-triflate (4.4 g, 20 mmol) was added to the solution and after 1 h additional TMSO-triflate (2.2 g, 10 mmol) was added. After 2 h stirring at 60° C. the reaction mixture was cooled and poured into dilute sodium bicarbonate solution and extracted with ethyl acetate. The organic phase was washed with water, dried over sodium sulfate, filtered and reduced. 3.8 g (85%) of desired product was obtained after further purification on a short silica gel column (0–1% MeOH/$CH_2Cl_2$).

Preparation of Methyl 3'-S-cyclic othorester. 0.5 g (1 mmol) of 2'-O-acetyl-3'-S-benzoyl-3'-deoxy-5'-O-pivaloyl-β-D-xylofuranosylthymine was treated with 20 mL of hethanolic ammonia/1,4-dioxane (1:1) at 0° C. for 1 h under nitrogen. The solvent was removed and the residue was dissolved in 20 mL DCM under $N_2$. To this mixture 1 mL of trimethyl orthoformate was added followed by 0.5 mL (5 eq.) of methanesulfonic acid. The reaction mixture was stirred at room temperature for 10 min and quenched with dilute sodium bicarbonate solution. The organic layer was decanted, dried, filtered and reduced. The residue was purified by column chromatography and eluted with MeOH/$CH_2Cl_2$ (0-0.5% MeOH) to yield 0.28 g (70%).

Preparation of T-T diner of dithioorthoester.

5'-S-Benzoyl-5'-deoxy-3'-O-isobutyryl-thymidine (0.43 g, 1 mmol) was treated with $NH_3$ in MeOH under nitrogen for about 2 h. The solvent was removed under reduced pressure under a nitrogen atmosphere and the residue was dissolved in 10 mL of dry DCM. Methyl 3'-S-cyclic othorester (0.4 g, 1 mmol) was added, followed by TMSO-triflate (0.4 mL, 2 eq.). The reaction mixture was stirred for additional 15 min and was quenched with diluted sodium bicarbonate solution. The organic layer was decanted, dried, filtered and reduced and the residue was purified by column chromatography and eluted with MeOH/$CH_2Cl_2$ (0–2% MeOH) to yield 0.40 g (60%).

Totally deprotection of T-T dimer of dithioorthoester. 0.34 g (0.5 mmol) of 5',3"-protected T-T dimer was stirred with 60 mg (2 eq) of NaOMe in 10 mL of MeOH at room temperature for 12 h. 20 mL of water and mL of MeOH were added and the reaction mixture was neutralized with amberlite-200 (strong acid form). The resin was filtered the solvent was removed. The residue was ready for the next step without any further purification.

Dimethoxytritylation of T-T diner of dithioorthoester. The residue obtained was co-evaporated two times with dry pyridine and then dissolved in 10 mL of dry pyridine. 0.2 g (1.2 eq.) of DMTCl was added and the reaction mixture was stirred for 2 h at room temperature. The solution was quenched with dilute sodium bicarbonate aqueous and extracted with DCM. The organic phase was decanted and washed with water and dried over sodium sulfate. The solution was filtered, the solvent was removed and the residue subjected to column chromatography and eluted with MeOH/$CH_2Cl_2$ (0–2% MeOH) to yield 0.27 g (64%).

5'-O-DMT T-T dithiorthoester H-phosphonate dimer. The DMT-protected dimer 0.27 g (0.32 mmol) was treated with van Boom's reagent as described before and purified by column chromatography and eluted with $Et_3N$/MeOH/$CH_2Cl_2$ (0–5% MeOH) followed by $Et_3N$/$CH_3CN$/$H_2O$ (0–5% $H_2O$).

EXAMPLE 22

Figure 23:
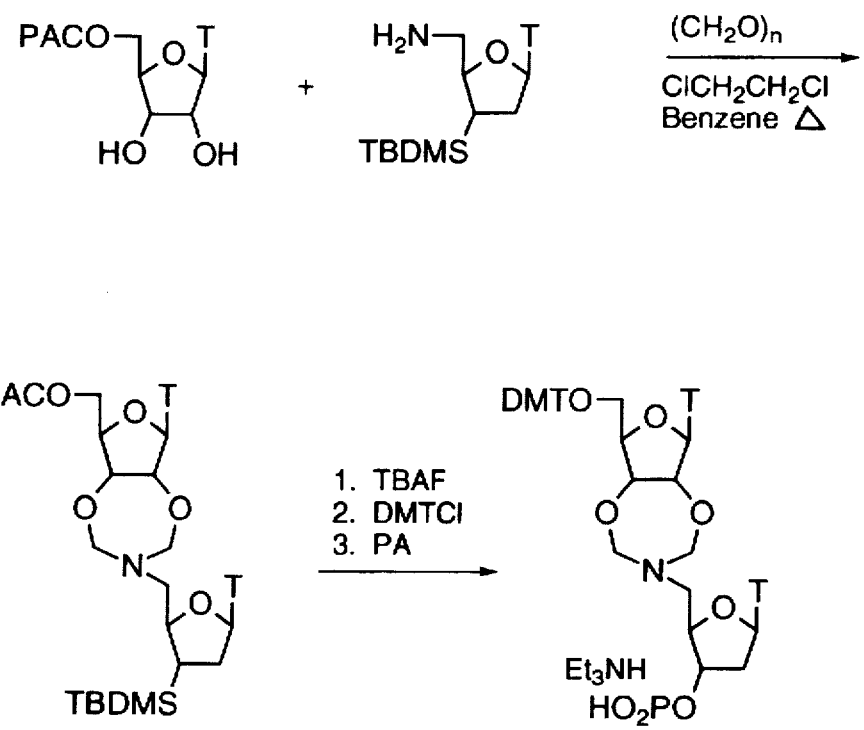
FIG. 23 describes the synthesis of a seven member ring system.
Figure 24:
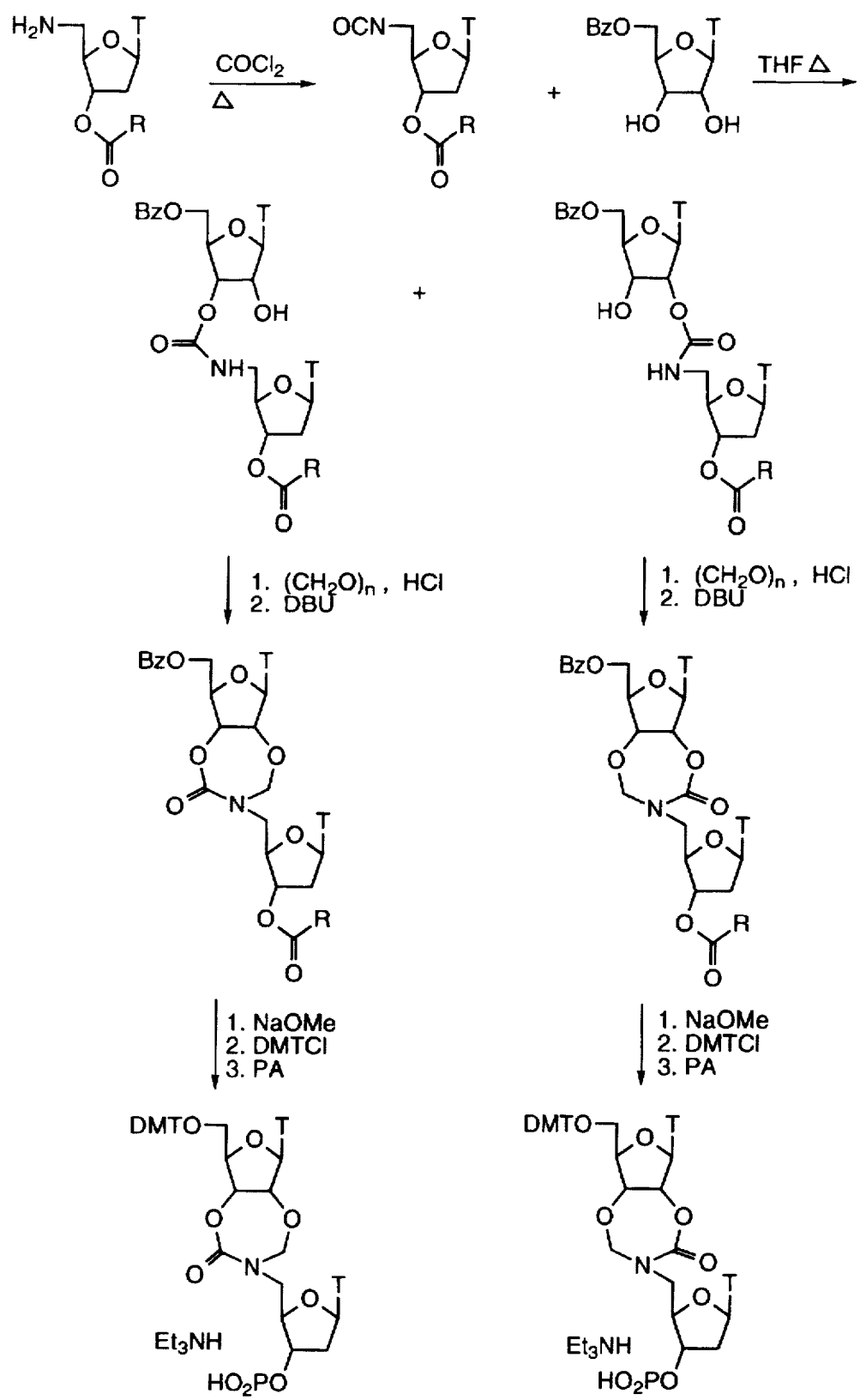
FIG. 24 describes the synthesis of a seven member ring system.
Figure 25A:
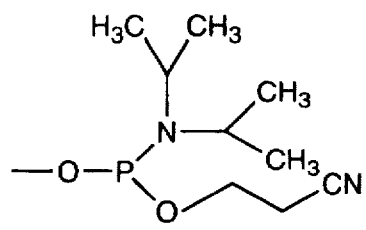
FIGS. 25-A to 25-D show structures used for linkage of nucleomonomers linked via phosphorous containing linkages.
Figure 25A:
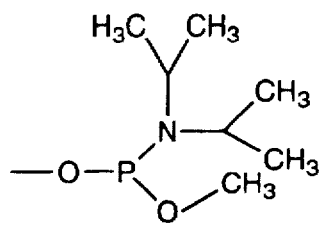
Figure 25A:
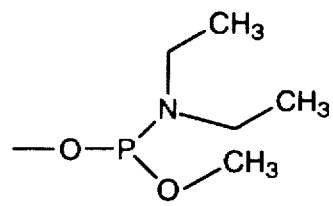
Figure 25A:
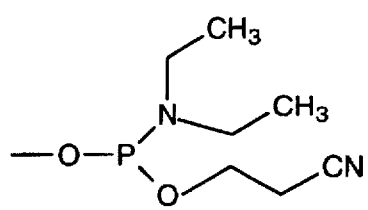
Figure 25A:
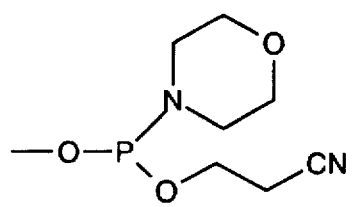
Figure 25A:
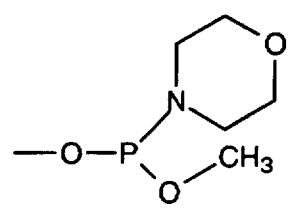
Figure 25B:
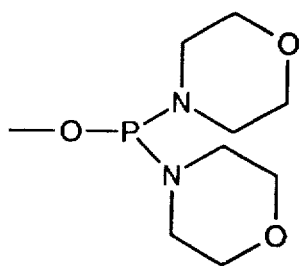
Figure 25B:
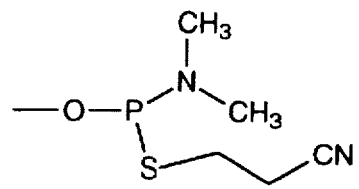
Figure 25B:
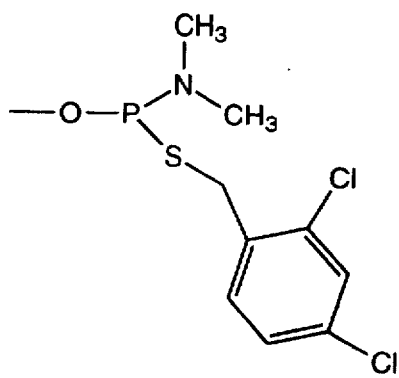
Figure 25B:
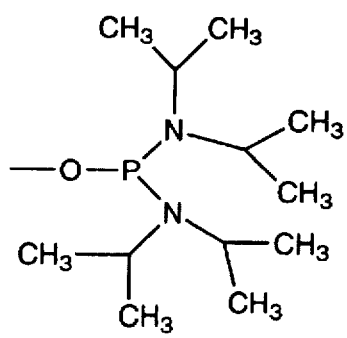
Figure 25C:
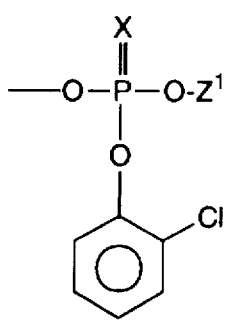
Figure 25C:
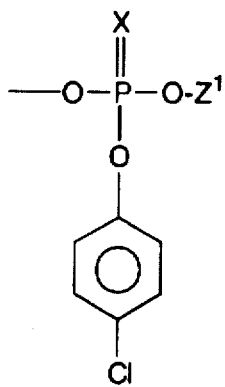
Figure 25C:
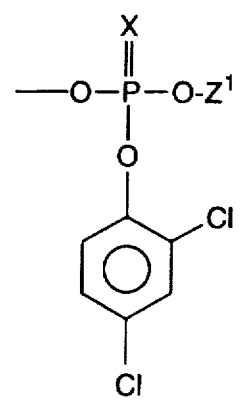
Figure 25C:
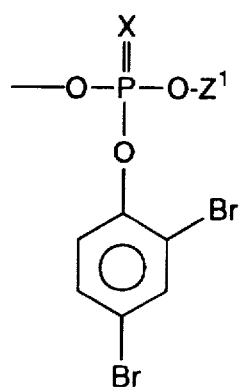
Figure 25C:
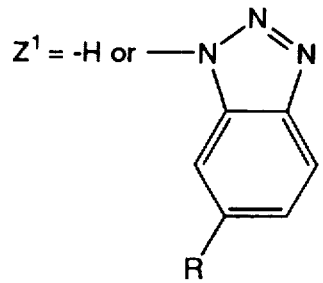
Figure 25D:
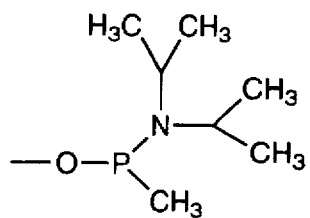
Figure 25D:
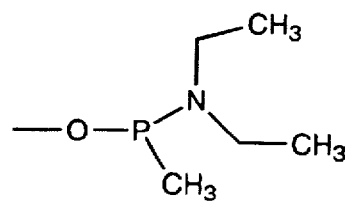

Experiments for FIG. 23

7-member ring. A solution of the diol (355 mg, 0.72 mmol), amine (235 mg, 0.72 mmol), paraformaldehyde (54 mg, 1.80 mmol), benzene (25 mL), and dichloroethane (25 mL) was heated to 80° C. for 18 h. The solution was cooled, filtered, and concentrated. The crude product was chromatographed (ME:MC 5:95) to deliver the 7-member ring compound. (Ref: Kaprand, H., Charles, G., *Tetrahedron Lett.,* (1980) 21:2949). A solution of 7-member ring compound and dioxane (25 mL) was treated with conc. $NH_4OH$ (25 mL) for 18 h. The solution was evaporated; absolute ethanol was added (2×150 mL), and the solution was again evaporated. Flash chromatography on silica gel (ME:MC 2:98 to 10:90) delivered the product.

Diol. The silyl derivative was treated with TBAF as described in FIG. 18.

5'-O-DMT T-T 7-member ring. This compound was prepared as described in FIG. 18.

5'-O-DMT T-T-7-member ring H-phosphonate. This compound was prepared as described in FIG. 18.

The instant invention is shown and described herein in what is considered to be the most practical and preferred embodiments. It is recognized, however, that departures may be made therefrom which are within the scope of the invention, and that modifications will occur to those skilled in the art upon reading this disclosure.

We claim:

1. An oligomer of the formula

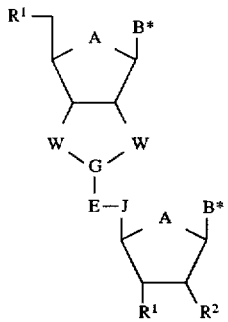

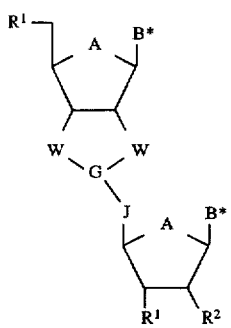

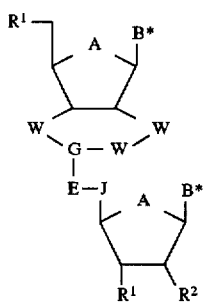

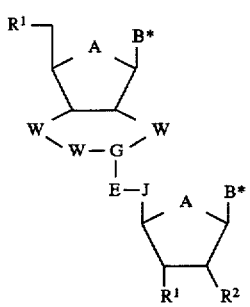

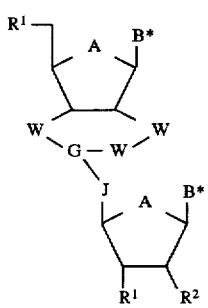

or

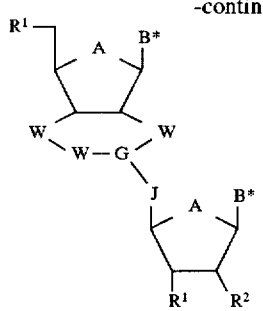

wherein each B* is independently a purine or pyrimidine base;

each $R^1$ is independently OH, $OPO_3^{-2}$, a nucleomonomer, two linked nucleomonomers, a solid support or a blocking group;

$R^2$ is H, OH, F, $OC_2H_5$, $SC_2H_5$, $OCH_3$, O-allyl, $SCH_3$, S-allyl, O-propyl or S-propyl;

$R^3$ is methyl;

$R^4$ is methyl, fluoromethyl or trifluoromethyl;

A is O, S, or $CH_2$;

E is $CH_2$, $CF_2$, NH or $NR^3$;

G is independently CH, N, or $CR^4$;

J is O, S, $SO_2$, or $CH_2$, provided that no adjacent —E—J— are —O—O—, —O—S—, —S—O—, —CF$_2$—O—, —O—CF$_2$—, —CF$_2$—S— or —S—CF$_2$—; and each W is independently O, S, $CH_2$, CO, or NH.

2. The oligomer of claim 1 wherein the oligomer is selected from the group consisting of

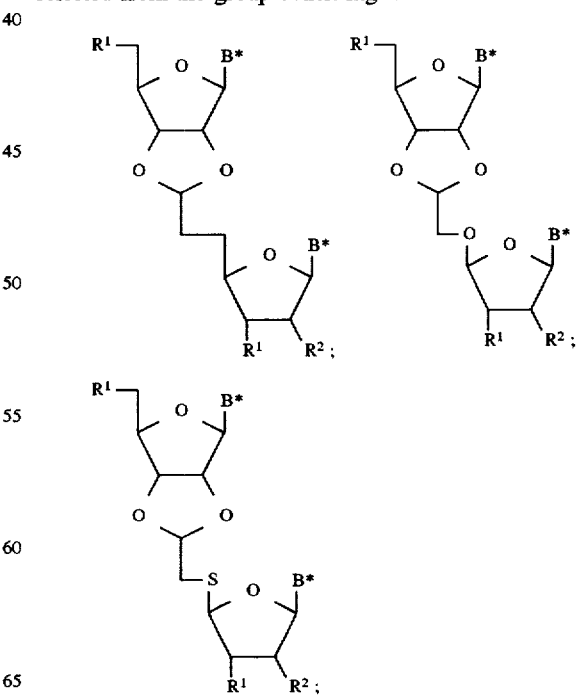

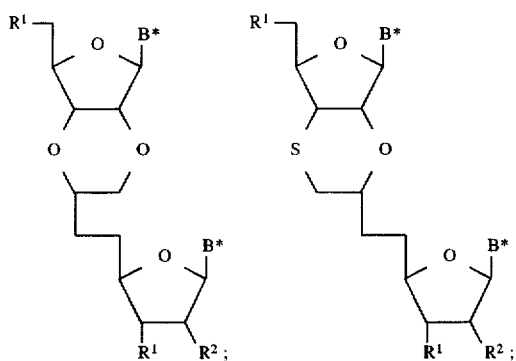

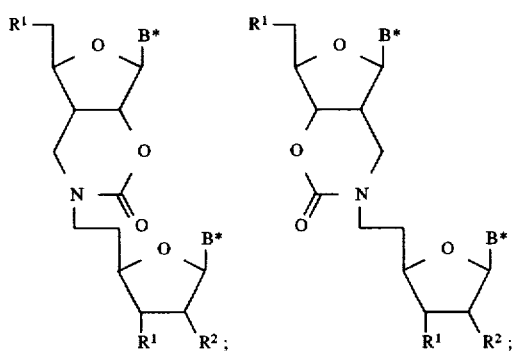

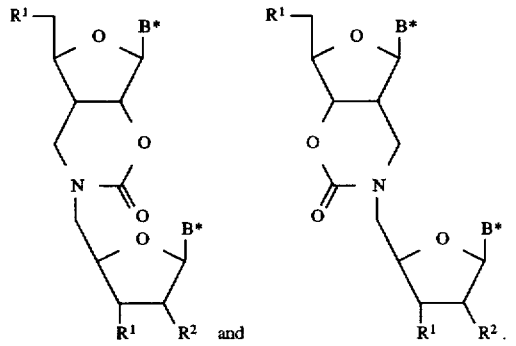

3. The oligomer of claim 2 wherein each B* independently is guanine, adenine, cytosine, thymine, uracil, 5-(1-propynyl)uracil, 5-(1-propynyl)cytosine, 5-methylcytosine or 7-deazaxanthine.

4. The oligomer of claim 2 wherein the oligomer is of the formula

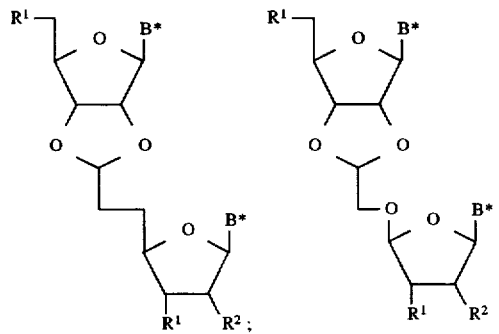

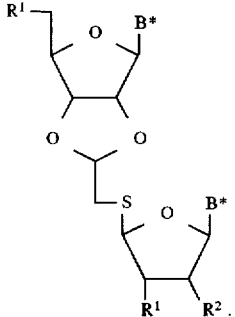

5. The oligomer of claim 4 wherein the oligomer is of the formula

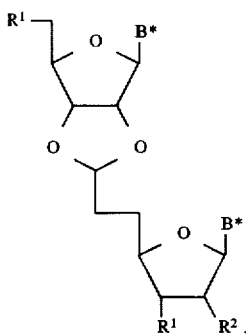

6. The oligomer of claim 2 wherein the oligomer comprises 2 or 3 nucleomonomers.

7. The oligomer of claim 1 wherein the oligomer comprises a radiolabel.

8. The oligomer of claim 7 wherein the oligomer comprises a radiolabel selected from the group consisting of $^{32}$P, $^{35}$S, $^{3}$H and $^{14}$C.

9. The oligomer of claim 1 wherein the oligomer comprises a fluorescent label.

10. The oligomer of claim 9 wherein the oligomer comprises a fluorescent label selected from the group consisting of fluorescein, resorufin, rhodamine, BODIPY and Texas red.

11. The oligomer of claim 1 wherein the oligomer comprises 2 or 3 nucleomonomers.

12. The oligomer of claim 1 wherein at least one $R^1$ is DMTO, MMTO, methylphosphonamidite, methylphosphoramidite, β-cyanoethylphosphoramidite or alkylphosphoramidite.

13. The oligomer of claim 12 which comprises two nucleomonomers.

14. The oligomer of claim 12 wherein $R^1$ at the 3' position is selected from the group consisting of N,N-diisopropylamino-β-cyanoethoxyphosphine, N,N-diisopropylaminomethoxyphosphine or H-phosphonate;

$R^1$ at the 5' position is OH, DMTO or MMTO; and
$R^2$ is H, OH, O-allyl or F.

15. An oligomer and salts thereof, comprising two nucleomonomers, wherein a first nucleomonomer and a second nucleomonomer are coupled through a substitute linkage wherein said substitute linkage comprises a 5- or 6-member ring containing C2' and C3' of said first nucleomonomer covalently linked through a bridging moiety to C4' of said second nucleomonomer.

16. The oligomer of claim 15 wherein the oligomer is of the formula

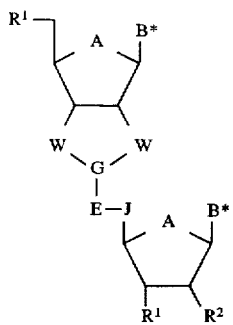

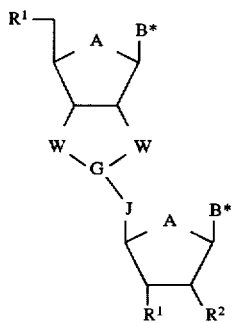

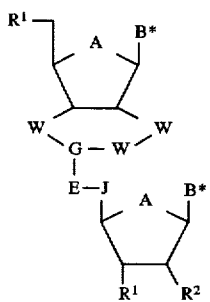

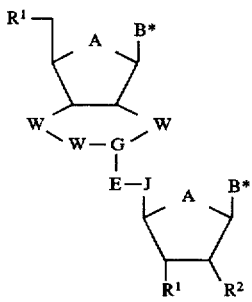

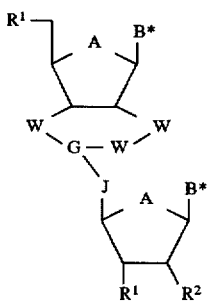

or

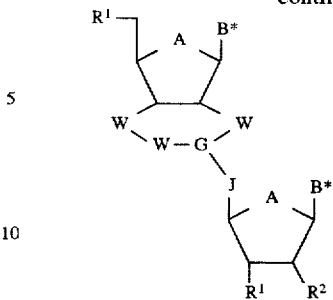

-continued wherein each B* is independently a purine or pyrimidine base;

each $R^1$ is independently OH, $OPO_3^{-2}$, a solid support or a blocking group;

$R^2$ is H, OH, F, $OC_2H_5$, $SC_2H_5$, $OCH_3$, O-allyl, $SCH_3$, S-allyl, O-propyl or S-propyl;

$R^3$ is $C_{1-4}$ alkyl;

$R^4$ is $C_{1-4}$ alkyl, $C_{1-4}$ fluoroalkyl having 1 to 6 fluorine atoms, 5-tetrazole, hydroxymethyl, CN, $CO_2H$, $CO_2R^3$, $CONH_2$, $CONHR^3$, $CON(R^3)_2$, $CH_2SR^3$, $CH_2SOR^3$, $CH_2SO_2R^3$, $CH_2CO_2H$, $CH_2CN$, $CH_2CO_2R^3$, $CH_2CONHR^3$ or $CH_2CON(R^3)_2$;

A is O, S, $CH_2$, CO, $CF_2$ or CHF;

E is O, S, SO, $SO_2$, $CH_2$, CO, $CF_2$, CS, NH or $NR^3$;

G is independently CH, N, CF, CCl or $CR^4$;

J is O, S, SO, $SO_2$, $CH_2$, CO, $CF_2$, or CS, provided that no adjacent —E—J— are —O—O—, —O—S—, —S—O—, —$CF_2$—O—, —O—$CF_2$—, —$CF_2$—S— or —S—$CF_2$—; and each W is independently O, S, SO, $SO_2$, $CH_2$, CO, $CF_2$, CS, NH or $NR^3$.

17. The oligomer of claim 16, wherein A is O, S or $CH_2$; $R^2$ is H, OH, F, $OCH_3$ or O-allyl; E is $CH_2$, $CF_2$, NH or $NR^3$; G is CH, N, NH or $CR^4$; J is O, S, $SO_2$, or $CH_2$; W is O, S, $CH_2$, CO or NH; $R^3$ is methyl; and $R^4$ is methyl, fluoromethyl or trifluoromethyl.

18. The oligomer of claim 17 having a structure selected from the group consisting of

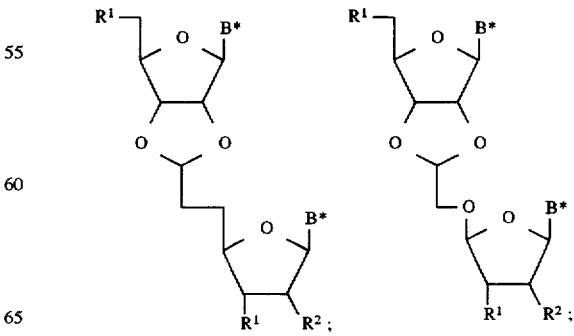

-continued

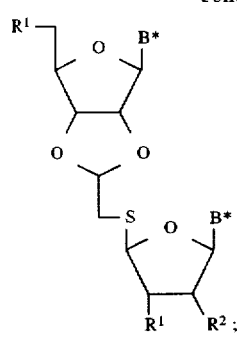

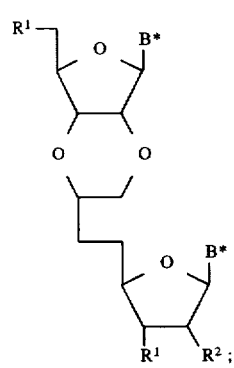

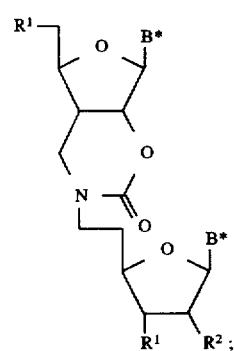

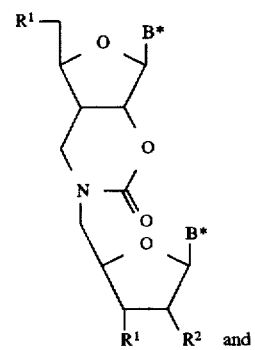

19. The oligomer of claim 18 wherein each B* independently is guanine, adenine, cytosine, thymine, uracil, 5-(1-propynyl)uracil, 5-(1-propynyl)cytosine, 5-methylcytosine or 7-deazaxanthine.

20. The oligomer of claim 18 wherein the oligomer is of the formula

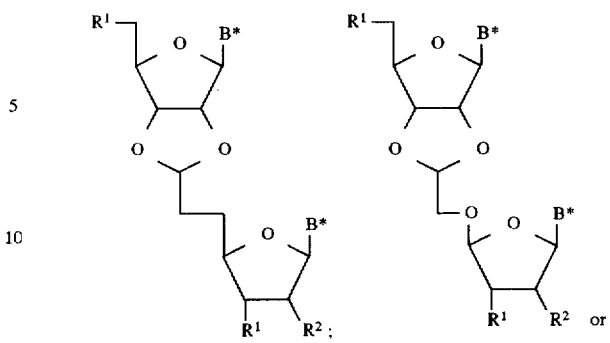

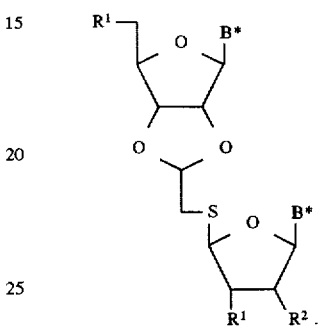

21. The oligomer of claim 20 wherein the oligomer is of the formula

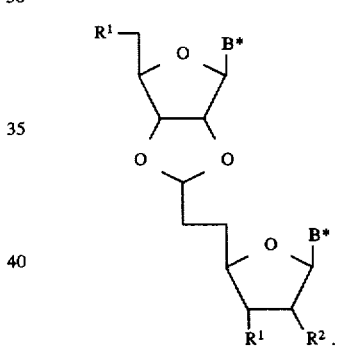

22. The oligomer of claim 15 wherein the 5-membered ring is of the formula

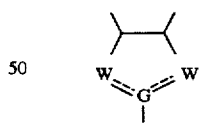

wherein each W is independently selected from the group consisting of O, S, SO, $SO_2$, $CH_2$, CH, CO, $CF_2$, CS, N, NH and $NR^3$;

G is selected from the group consisting of C, CH, N and $CR^4$;

$R^3$ is $C_{1-4}$ alkyl; and $R^4$ is $C_{1-4}$ alkyl or $C_{1-4}$, $F_{1-6}$ fluoroalkyl, provided that only one W is N or CH and when W is N or CH, W is connected to G by a double bond.

23. The oligomer of claim 22 wherein the bridging moiety is a one atom bridge of the formula —J— wherein J selected from the group consisting of O, S, SO, $SO_2$, $CH_2$, CH, CO, $CF_2$ and CS.

24. The oligomer of claim 23 wherein W is O or S, G is CH and J is $CH_2$.

25. The oligomer of claim 22 wherein the bridging moiety is a two atom bridge of the formula —E—J— wherein —J— is selected from the group consisting of O, S, SO, $SO_2$, $CH_2$, CH, CO, $CF_2$ and CS, and wherein —E— is selected from the group consisting of O, S, SO, $SO_2$, $CH_2$, CO, $CF_2$, CS, NH and $NR^3$, provided that —E—J— is not —O—O—, —O—S—, —S—O—, —$CF_2$—O—, —O—$CF_2$—, —$CF_2$—S— or —S—$CF_2$.

26. The oligomer of claim 25 wherein W is O or S, G is CH or $CR^4$, E is O, S or $CH_2$ and J is $CH_2$.

27. The oligomer of claim 26 wherein W is O, G is CH, and E and J are both $CH_2$.

28. The oligonucleotide of claim 15 wherein the 6-membered ring is of the formula

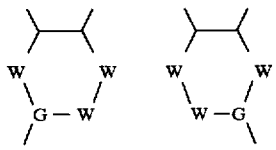

wherein
each W is independently selected from the group consisting of O, S, SO, $SO_2$, $CH_2$, CO, $CF_2$, CS, N, NH and $NR^3$;
G is selected from the group consisting of C, CH, N and $CR^4$;
$R^3$ is $C_{1-4}$ alkyl; and
$R^4$ is $C_{1-4}$ alkyl or $C_{1-4}$, $F_{1-6}$ fluoroalkyl, $CH_2OH$, 5-tetrazole, CN, $CH_2$-(5tetrazole), $CO_2H$, $CO_2R^3$, $CONH_2$, $CONHR^3$, $CON(R^3)_2$, $CH_2SR^3$, $CH_2SOR^3$, $CH_2SO_2R^3$, $CH_2CN$, $CH_2CO_2H$, $CH_2CO_2R^3$, $CH_2CONH_2$, $CH_2CONHR^3$ and $CH_2CON(R^3)_2$, provided that adjacent —W—W— are not —O—O—, —O—S—, —S—O—, —$CF_2$—O—, —O—$CF_2$—, —$CF_2$—S— or —S—$CF_2$.

29. The oligomer of claim 28 wherein the bridging moiety is a one atom bridge of the formula —J— wherein J selected from the group consisting of O, S, SO, $SO_2$, $CH_2$, CH, CO, $CF_2$ and CS.

30. The oligomer of claim 29 wherein W is O, $CH_2$ or S, G is CH or $CR^4$ and J is $CH_2$.

31. The oligomer of claim 25 wherein W is O, $CH_2$ or S, G is CH or $CR^4$, E is O, S or $CH_2$ and J is $CH_2$.

32. A method of synthesizing the oligonucleotide of claim 15 comprising:

(a) synthesizing a protected nucleomonomer synthon having a protecting group and a base and having a coupling group capable of coupling to an acceptor nucleomonomer or acceptor oligonucleotide;

(b) coupling the nucleomonomer synthon to the acceptor nucleomonomer or acceptor oligonucleotide;

(c) removing the protecting group; and (d) repeating steps (a) through (c) until the desired oligonucleotide is synthesized.

33. The method of claim 32 wherein the coupling group is a phosphite or a phosphate group.

34. The method of claim 32 wherein step (b) is accomplished using hydrogen phosphonate, phosphoramidite or phosphotriester chemistry.

35. The method of claim 34 wherein the hydrogen phosphonate, phosphoramidite or phosphotriester chemistry uses a coupling group selected from the group consisting of hydrogen phosphonate, N,N-diisopropylaminomethylphosphonamidite, N,N-diethylmethylaminophosphonamidite, N,N-diisopropylamino-β-cyanoethoxyphosphine, N,N-diisopropylaminomethoxyphosphine, N,N-diethylamino-β-cyanoethoxyphosphine, N,N-morpholino-β-cyanoethoxyphosphine, N,N-morpholinomethoxyphosphine, chlorophenyl phosphate, 4-chlorophenyl phosphate, 2,4-dichlorophenyl phosphate, 2-chlorophenyl thiophosphate, 4-chlorophenyl thiophosphate, 2,4-dichlorophenyl thiophosphate, and 2,4-dibromophenyl phosphate.

* * * * *